United States Patent [19]
Oxman et al.

[11] Patent Number: 5,596,025
[45] Date of Patent: Jan. 21, 1997

[54] DENTAL IMPRESSION MATERIAL WITH CURE-INDICATING DYE

[75] Inventors: Joel D. Oxman; Mark S. Konings, both of Minneapolis; George V. D. Tiers, St. Paul; Kim M. Vogel; Dennis E. Vogel, both of Lake Elmo, all of Minn.

[73] Assignee: Minnesota Mining and Manufacturing Company, St. Paul, Minn.

[21] Appl. No.: 496,772

[22] Filed: Jun. 29, 1995

Related U.S. Application Data

[63] Continuation-in-part of Ser. No. 269,195, Jun. 30, 1994, abandoned.

[51] Int. Cl.$^6$ .................................................... C08L 83/05
[52] U.S. Cl. ......................... 523/109; 524/714; 524/715; 524/717; 524/718; 524/720; 524/723; 524/862; 524/751
[58] Field of Search ........................... 523/109; 524/862, 524/714, 715, 717, 718, 720, 723, 751

[56] References Cited

U.S. PATENT DOCUMENTS

| | | | |
|---|---|---|---|
| 2,915,544 | 12/1959 | Holbrook et al. | 260/448.2 |
| 3,159,601 | 12/1964 | Ashby | 260/46.5 |
| 3,159,662 | 12/1964 | Ashby | 260/448.2 |
| 3,220,972 | 11/1965 | Lamoreaux | 260/46.5 |
| 3,410,886 | 11/1968 | Joy | 260/448.2 |
| 3,505,377 | 4/1970 | Morehouse | 260/448.2 |
| 3,509,081 | 4/1970 | Gignac, Jr. | 260/18 |
| 3,715,334 | 2/1973 | Karstedt | 260/46.5 |
| 3,775,452 | 11/1973 | Karstedt | 260/429 R |
| 3,814,730 | 6/1974 | Karstedt | 260/46.5 |
| 3,933,914 | 1/1976 | Coles et al. | 260/577 |
| 3,950,300 | 4/1976 | Hittmair et al. | 523/109 |
| 3,980,688 | 9/1976 | Litteral et al. | 260/448.8 R |
| 4,018,810 | 4/1977 | Skoog | 260/465 D |
| 4,160,776 | 7/1979 | Scardera et al. | 260/448.8 R |
| 4,222,983 | 9/1980 | August et al. | 264/200 |
| 4,226,794 | 10/1980 | Scardera et al. | 556/443 |
| 4,337,168 | 6/1982 | Scardera et al. | 252/312 |
| 4,357,405 | 11/1982 | Leichter et al. | 430/58 |
| 4,431,789 | 2/1984 | Okazaki et al. | 528/15 |
| 4,484,990 | 11/1984 | Bultman et al. | 204/106 |
| 4,510,094 | 4/1985 | Drahnak | 260/429 CY |
| 4,530,879 | 6/1985 | Drahnak | 428/352 |
| 4,600,731 | 7/1986 | Louis et al. | 523/109 |
| 4,657,959 | 4/1987 | Bryan et al. | 524/266 |
| 4,698,386 | 10/1987 | Fujimoto | 524/862 |
| 4,788,240 | 11/1988 | Fujimoto | 524/290 |
| 4,916,169 | 4/1990 | Boardman et al. | 522/27 |
| 5,047,444 | 9/1991 | DeVoe et al. | 522/99 |
| 5,118,559 | 6/1992 | DeVoe et al. | 428/262 |
| 5,145,886 | 9/1992 | Oxman et al. | 522/66 |
| 5,182,316 | 1/1993 | DeVoe et al. | 522/99 |

FOREIGN PATENT DOCUMENTS

| | | |
|---|---|---|
| 0225843 | 7/1986 | European Pat. Off. . |
| 0492830A2 | 1/1992 | European Pat. Off. ......... C08K 5/00 |
| 0579132 | 1/1994 | European Pat. Off. . |

OTHER PUBLICATIONS

Zhurnal Organicheskoi Khimii, vol. 15, No. 11, pp. 2416–2417 (Nov. 1979).

Fundamentals of Polymer Processing, Stanley Middleman, pp. 327 and 328.

"The Quantitative Determination of some Noble Metals by Atomic-absorption Spectroscopy", R. Lockyer and G. E. Hames, Analyst, 84, pp. 385–387 (1959).

"Indoaniline Dyes. I. Some Phenol Blue Derivatives with Substituents in the Phenol Ring", Paul W. Vittum and Gordon H. Brown, J. Am. Chem. Soc., Nov. 1946, 68, pp. 2235–2239.

"Synthesis and Structure of a rac–Tris(divinyldisiloxane)diplatinum(0) Complex and its Reaction with Maleic Anhydride", P. B. Hitchcock, M. F. Lappert and N. J. W. Warhurst, Angew. Chem., Int. Ed. Engl. 30 (1991) No. 4, pp. 438–440.

"Silicones", Kirk–Othmer Encyclopedia of Chemical Technology, 3rd Ed., 20, 922–962 (1982).

Silicon Compounds Register and Review – Silicones & Silicon–Containing Polymers, 5th Edition, edited by Roy Anderson, G. L. Larson and Craig Smith, Huls America Inc., Piscataway, NJ, p. 268.

Preparatory Example 1b and p. 13 of "Aspects of Some Divinylsiloxane Complexes of Platinum and Rhodium", PhD thesis of Nicholas John William Warhurst, University of Sussex, Mar. 1990.

UCAR–SIL EPS Silicone Hydrophilic Finish, dated Mar. 1984.

Olin Corp. product literature "Silicate Cluster Fluids".

"Surfactants and Detersive Systems", Kirk–Othmer Encyclopedia of Chemical Technology, 3rd Ed., 22, 360–377 (1983).

Adachi et al., J. Org. Chem., 1933, 58, 5238–5244.

Organomodified Oils (OMO), dated Apr. 1982.

"Thermal Decomposition of Bis(phosphine)platinum(II) Metallocycles", J. X. McDermott, J. F. White and G. M. Whitesides, J. Am.Chem. Soc., Oct. 13, 1976, 98:21, pp. 6522–6528.

"Redox Systems in Nonaqueous Solvents", M. Rumeau, The Chemistry of Nonaqueous Solvents, vol. IV (1976) pp. 75–107.

(List continued on next page.)

*Primary Examiner*—Ralph H. Dean
*Attorney, Agent, or Firm*—Gary L. Griswold; Walter N. Kirn; Dale A. Bjorkman

[57] ABSTRACT

The present invention provides novel dental impression materials, the cure of which can be monitored visually, comprising: (1) a curable silicone polymer; (2) a crosslinker compound containing silicon-bonded-hydrogen groups; (3) a hydrosilation catalyst; and (4) one or more cure-indicating dyes that exhibit a color change in the presence of a silicon-bonded-hydrogen compound and a hydrosilation catalyst. The cure-indicating dye provides the composition with an initial pre-cure color and a different post-cure color. As a result of this change in color, the state of cure of the impression material can be visually monitored.

53 Claims, 1 Drawing Sheet

OTHER PUBLICATIONS

"Electrode Potentials in Non–Aqueous Solvents", H. Strehlow, The Chemistry of Non–aqueous Solvents, vol. I (1966), pp. 129–171.

"Olefin Complexes of Platinum, J. L. Spencer, Inorganic Syntheses, vol. XIX, 49, pp. 213–218 Union Carbide Corp. product literature, Silwet Surfactants", dated Jun. 1994 (replaces Aug. 1992).

Abstract: JP 61 157 557; 17 Jul. 1986.

DENTAL IMPRESSION MATERIAL WITH CURE-INDICATING DYE

This application is a continuation-in-part application of U.S. application Ser. No. 08/269,195, filed Jun. 30, 1994, now abandoned.

FIELD OF THE INVENTION

This invention relates to cure-indicating polysiloxane compositions, which compositions are useful for preparing dental and otologic impressions, and medical and dental implants. This invention further relates to compositions and methods for visually indicating a cure point of a hydrosilation curable composition (e.g., a silicone composition) via a color change.

RELATED APPLICATIONS

Of related interest is the following U.S. patent application, filed on even date herewith by the assignee of this invention: "Cure-indicating Molding and Coating Composition", U.S. Ser. No. 496,499, filed Jun. 29, 1995, Express Mail, which is herein incorporated by reference.

BACKGROUND OF THE INVENTION

Many materials undergo a change in state as a result of a "curing reaction." For example, as a result of a curing reaction a liquid resin composition can be changed into a solid or elastomeric material. The curing reaction can be initiated in a number of different ways, including for example, heating the uncured sample, mixing two or more reactive components together, or exposing the uncured material to an activating radiation source or electron beam energy. Depending on the method of curing employed the transition time between states can vary in length. For some materials the change in state may be observed by simply probing the material and observing a change in viscosity. This technique, however, is subject to error and misinterpretation in many cases. In addition, manually probing samples may damage the sample, and may not indicate small but important changes in the extent of cure. Other techniques of observing a material's change in state include monitoring the rheological properties of the material, or analytically monitoring the material (e.g., using an instrument such as an NMR probe to observe directly a change in the functional groups of the material). Unfortunately, these direct techniques are often not practical for the routine monitoring of a cure reaction or may be invasive or destructive of the sample being monitored.

One example of a material that undergoes a curing reaction is a silicone material. "Silicones" are synthetic polymeric materials that possess an extraordinarily wide range of physical properties. They can be low- or high-viscosity liquids, solid resins, or vulcanizable gums. They display an unusual combination of organic and inorganic chemical properties that are due to their unique molecular structure of alternating silicon and oxygen atoms. One typical polysiloxane polymer is depicted below in formula F1.

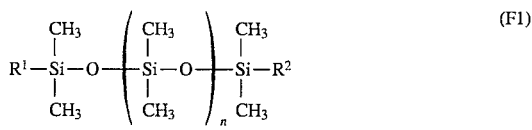

(F1)

These silicone polymers may be made by an equilibrium process from other siloxanes and typically range in viscosity from about 0.01 Pa s to 2500 Pa s. Silicone polymers can be mixed with other chemicals and fillers into an enormous variety of products that serve in a multitude of applications.

Vulcanizing silicones are a special class of silicones that have as a common attribute the development of a "crosslinked" elastomer from relatively low molecular weight polymers by means of a chemical reaction that forms these crosslinks and effectively extends chain length simultaneously. Vulcanizing silicones (e.g., addition-cure silicones) have many applications in industry including use as sealants, caulks, adhesives, coatings, potting materials, release liners, otologic impression materials, molding materials, dental impression materials and medical and dental implants. An essential ingredient in a vulcanizing silicone is a crosslinking component (hereinafter the "crosslinker") that reacts with the "functional group" or groups (e.g., $R^1$ and $R^2$ of figure F1) of the polymer chains to simultaneously lengthen them and connect them laterally to form the crosslinked network characteristic of a silicone elastomer. Usually a catalytic agent is included to facilitate the reaction of the crosslinker with the polymer's functional groups.

There are many types of vulcanizing silicones and likewise many types of crosslinking components and catalysts. Two such systems include (i) condensation-cured silicones and (ii) addition-cured, e.g., hydrosilylation cured (alternatively spelled "hydrosilation") silicones. Condensation-cured silicones characteristically, and in many instances detrimentally, release water (or alcohol) as a by-product of the crosslinking reaction. The crosslinking reaction in these systems is triggered typically by combining the silicone polymer, the crosslinker and the catalyst. A variety of catalysts initiate and accelerate condensation curing such as amines and carboxylic acid salts of tin. At low temperatures the condensation-cured silicone typically requires long times to fully cure (hours or even days). Higher catalyst concentrations and/or higher temperatures can shorten the cure time.

Addition-cured silicones (e.g., hydrosilylation cured silicones) are generally considered to be of higher quality and are dimensionally more accurate than condensation-cured silicones. Unlike condensation-cured silicones, addition-cured silicones, e.g., hydrosilation-cured silicones, do not produce detrimental byproducts during curing. Such silicones differ from condensation-cured silicones in that the hydrosilation-cured composition typically contains:

(1) a polymer which contains two or more vinyl functional groups;

(2) a "hydrosilane" crosslinker component containing two or more SiH bonds; and (3) a precious metal catalyst such as a platinum catalyst.

A particularly preferred addition-cured silicone is formed by reacting (1) a multiply-vinyl-containing organopolysiloxane with (2) an organopolysiloxane containing a multiplicity of SiH bond per molecule (hereinafter "organohydropolysiloxane"). This reaction is typically facilitated by the presence of (3) a platinum catalyst of the Karstedt type. Platinum catalysts of the Karstedt type are described in U.S. Pat. Nos. 3,715,334, 3,775,452 and 3,814,730 which are herein incorporated by reference.

When vulcanizing silicones are used as modeling compounds (e.g., dental impression materials) it is customary to provide the compound to the user as two separate mixtures (i.e., the hydrosilation catalyst is stored separately from the hydrosilane crosslinker). When the user is ready to prepare an impression or model, the two parts will be mixed together, the silicone will be placed against the surface or object to be modeled and then the user will wait until the silicone completely cures. The cured silicone is then removed from the surface or object and retains a negative impression of that surface. A positive model may then be formed by filling the impression cavity with a material such as wax or plaster of Paris. In many instances it may not be feasible to form the positive model immediately. Therefore, it is also important that the impression retains its dimensional accuracy over a long period of time (often weeks or months).

The setting reaction of a vulcanizing silicone is triggered, in general, by the mixing together of the catalyst, crosslinker and polymer. By varying the amount of catalyst and crosslinker, the rate of setting may be adjusted. The rate of setting may be further adjusted by the incorporation of well known inhibitors and/or retarders. One such inhibitor is 1,3,5,7-tetramethyl-1,3,5,7-tetravinylcyclotetrasiloxane. These retarders often operate by reacting competitively with the catalyst thereby slowing the crosslinking reaction. In general, with the slowing of the reaction both the working time and the setting time (as defined below) are affected.

As the material begins to set, its viscosity increases. Eventually, the mixture becomes "gelled" and is changed irreversibly into a crosslinked polymer or an "elastomer." At the gel-point the material no longer easily flows or adapts to new shapes. Therefore, in applications such as the taking of a dental impression this period of time defines the extent of the "working time" period.

When the reaction is complete (or "practically" complete) the material is said to be "set." This "setting time" is likewise an important parameter for a silicone impression material, as it is crucial that the material remain in contact with the surface it is to replicate until it has completely set. For dental impressions it is desirable to have a relatively short setting time (e.g., less than 10 minutes). Premature removal from the surface being replicated may result in a distorted impression which will continue to crosslink, in the distorted position, outside of the mouth. Unfortunately, this situation is often unnoticed by the dentist initially and is discovered only after an expensive, but worthless, dental appliance has been fabricated. The dentist and patient must then go through the entire lengthy impression making and appliance fabrication process again. This is a great expense and inconvenience.

For applications requiring detailed reproduction, such as dental impression materials, the setting time and the working time parameters are very important and must be carefully controlled. As previously mentioned, the working time measures the time period over which the reacting silicone material remains fluid enough to flow and change shape. After the reaction has reached the "gel point" the material's properties change drastically and resist further fluid flow. It is desirable to have sufficient working time so that the dentist may easily, and prior to gelation, (1) mix the materials and (2) place them in the mouth.

One major factor which affects both the working time and the setting time (in addition to the aforementioned use of an inhibitor or retarder) is the catalyst's "activity." Unfortunately, platinum catalysts of the Karstedt variety are somewhat sensitive to degradation and therefore are of variable activity. While the exact mechanism is presently unknown, this degradation may be advanced at high temperatures (such as might be encountered in a hot warehouse or in a truck-trailer). Over time the catalyst composition is believed to degrade and the setting time of the mixed composition becomes longer and longer. As previously mentioned even small changes in the setting time can have a detrimental effect on the accuracy of an impression if the user removes the material prior to its complete cure. Such early removal becomes more likely if the catalyst activity unexpectedly decreases upon storage. Another major factor which affects both the working time and the setting time is the ratio of catalyst to crosslinker. This ratio may be adjusted (purposely or inadvertently) by varying the amounts of each paste in the mix.

Various approaches have been attempted to provide an indication of a material's extent of cure. For example, U.S. Pat. Nos. 5,047,444; 5,118,559; and 5,182,316 describe curable compositions that can be monitored for extent of cure via detection of a UV fluorophore which is generated during the curing process. These compositions require the use of both a UV irradiation source and a UV fluorescence detector to monitor the extent of cure effectively and cannot be visualized by the naked eye. U.S. Pat. No. 3,509,081 describes the use, in a condensation silicone composition, of a dye that exhibits a visible color change at the desired degree of cure. This system is apparently limited and unpredictable, since, as the inventors state, it is "believed there is no technical relationship between the desired cure and the ultimate color change." In addition, as previously mentioned condensation silicones are limited by their dimensional instability. European Patent Application 0 492 830 A2 describes a method, for ultraviolet radiation curing compositions, of indicating a cure point by color change. Compositions of this invention comprise free-radical-curable materials, UV activated free-radical initiators, and a dye that changes color upon exposure to ultraviolet radiation in the presence of free-radical-generating photoinitiators. Preferred dyes of this invention include anthraquinone and bis-azo dyes. U.S. Pat. No. 4,788,240 discloses compositions comprising a polyorganosiloxane having two or more alkenyl radicals, a polyorganohydrogensiloxane, a platinum or platinum compound catalyst, and an anthraquinone or azo dye. The compositions are described as being useful as a molding or dental impression material. Materials exemplified in this patent require extended curing times which are undesirable for many dental procedures.

SUMMARY OF THE INVENTION

This invention relates to compositions and methods for indicating visually a cure point of a hydrosilation-curable composition (e.g., a silicone composition) via a color change.

The present invention provides novel hydrosilation-curable compositions, the cure of which can be monitored visually, comprising: (1) a multiply-ethylenic compound; (2) a compound containing a multiplicity of silicon-bonded-hydrogen groups; (3) a metal or metal complex capable of catalyzing a hydrosilation reaction; and (4) one or more cure-indicating dye compounds with light absorption or emission in the visible spectrum (i.e., 400–800 nm) that exhibit a color change in the presence of a silicon-bonded-hydrogen compound and a precious metal hydrosilation catalyst.

The present invention provides, in another aspect, compositions (e.g., silicone compositions) which are useful for preparing sealants, caulks, adhesives, coatings, impression materials, molding materials, lithographic plates, release liners, poring materials and reflective sheets. The silicone compositions of the present invention, the cure of which can be monitored visually, comprise: (a) a curable silicone polymer, e.g., vinyl-containing organopolysiloxane; (b) a crosslinker, e.g., an organopolysiloxane containing a multiplicity of SiH bonds; (c) a catalyst such as a platinum or precious metal containing hydrosilation catalyst; and (d) one or more cure-indicating dyes that exhibit a color change in the presence of a silicon-bonded hydrogen compound and a precious metal hydrosilation catalyst. Presently preferred optional ingredients of the silicone composition include fillers (e.g., pulverized metals, silica, quartz, calcium carbonate or metal oxides), appropriate polymerization initiators and inhibitors, pigments, stabilizers, surfactants, modifying agents, indicator adjuvants, and copolymerizable and non-copolymerizable cosolvents, and the like. Preferred dental impression "putties" of the present invention comprise between about 20 and 90 weight percent filler, more preferably between about 40 and 80 weight percent filler, and most preferably between about 60 and 80 weight percent filler. Preferred dental impression "washes" (or "single phase" syringeable materials) comprise between about 10 and 70 weight percent filler, more preferably between about 20 and 60 weight percent filler, and most preferably between about 30 and 60 weight percent filler.

The curable silicone composition of the present invention can be prepared by combining (e.g., mixing together) the vinyl-containing organopolysiloxane, the organohydropolysiloxane, the platinum catalyst and the cure-indicating dye or dyes. In one embodiment, the components are pre-mixed into preferably two parts prior to use. For example, part "A" may contain the vinyl-containing organopolysiloxane, the platinum catalyst and the cure-indicating dye, while part "B" may contain the organohydropolysiloxane and optionally vinyl-containing organopolysiloxane. Alternatively, the cure-indicating dye may be incorporated in part "B" and not in part "A", or may be in both parts "A" and "B". In another embodiment, the components are provided in one part and further contain an ingredient (e.g., a catalyst inhibitor) which inhibits the cure reaction. Hydrosilation inhibitors are well known in the art and include such compounds as acetylenic alcohols, certain polyolefinic siloxanes, pyridine, acrylonitrile, organic phosphines and phosphites, unsaturated amides, and alkyl maleates. For example, an acetylenic alcohol compound can inhibit certain platinum catalysts and prevent curing from occurring at low temperatures. Upon heating, the composition begins to cure. The amount of catalyst inhibitor can vary up to about 10 times or more of the amount of catalyst, depending upon the activity of the catalyst and the shelf life desired for the composition. Alternatively, one may utilize a one-part composition comprising a cure-indicating dye, a vinyl-containing organopolysiloxane, an organohydropolysiloxane, and a platinum catalyst such as disclosed in U.S. Pat. Nos. 4,530,879, 4,510,094, 4,916,169, 5,145,886 and patent application Ser. Nos. 07/626,904 and 07/627,009. Such one-part compositions are stable at room temperature and cure when the catalyst is exposed to visible radiation.

A "cure-indicating dye" is added to the curable composition to provide a visual indication of the extent of the hydrosilation reaction (e.g., extent of the crosslinking reaction). The cure-indicating dye exhibits a color change in the presence of a silicon-bonded-hydrogen compound and a precious metal hydrosilation catalyst and is characterized in a curable composition by having a first color before the cure reaction is effected and a second color after the cure reaction has been effected to the indication point. The first color and second colors are sufficiently different (or have a sufficiently different intensity) and may be readily observed in the composition using the naked eye or, optionally, a suitable instrument such as a spectrophotometer, colorimeter or fluorimeter. The term "color" is here understood to include visible fluorescence when examined using light of a shorter wavelength, including "black light".

The compositions of the present invention may find utility in a variety of applications in which the visual identification of various stages of curing (such as working-time or setting-time) provides a benefit to the end-user. This feature is particularly beneficial in uses such as the taking of a dental impression where the timing of the cure can affect the quality of the impression. For example, if the dentist removes the impression material from the mouth before it is fully set the impression will likely become distorted as it continues to cure. Similarly, if the dentist delays too long, e.g., after mixing the impression material, when placing the material against the teeth, the material will not readily flow against the teeth and therefore not take an accurate impression of them. Each or both of these situations can be avoided by utilizing visual cure indications of the present invention.

Alternatively, these compositions may be used to prepare adhesives, caulking materials, gaskets, sealants, coatings, potting materials or any other application where a cure-indicating material is required. Preferred applications of this invention include areas in which non-stick or low-energy properties of a surface are required such as impression materials, modeling materials or in release coatings for use with pressure-sensitive adhesives.

Definitions

The term "crosslinked polymer," as used herein, refers to polymers that react with the functional group or groups of the polymer chains (e.g., $R^1$ and $R^2$ of figure F1) simultaneously to lengthen them and connect them laterally, e.g., to form the crosslinked network characteristic of a silicone elastomer. In contrast to a thermoplastic polymer (i.e., a polymer that softens and flows upon heating) a crosslinked polymer, after crosslinking, is characteristically incapable of further flow.

The term "Silicone," as used herein, refers to a polymer having, for the most part, alternating silicon and oxygen atoms (i.e., a polysiloxane chemical structure) and having sufficient pendant functional groups to undergo a setting reaction in the presence of a crosslinker compound and a catalyst compound.

The term "vulcanizing," as used herein, refers to silicones that have as a common attribute the development of a crosslinked elastomer from relatively low molecular weight linear or branched polymers by means of a chemical reaction that sumultaneously forms these crosslinks and effectively extends chain length at room temperature. "Room temperature vulcanizing" ("RTV") implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or>100° C.) and are stable (i.e., the curing reaction is retarded) at room temperature for prolonged periods.

The term "compound" is a chemical substance which has a particular molecular identity or is made of a mixture of such substances, e.g., polymeric substances.

The term "hydrosilation" means the addition of an organosilicon hydride compound to a compound containing an aliphatic multiple bond (e.g., an olefinic or acetylenic unsaturation), preferably a vinyl group, —CH=CH$_2$.

The term "working time" as used herein, refers to the time between the initiation of the setting reaction (e.g., when the vinyl-containing organopolysiloxane, the organohydropolysiloxane, and the platinum catalyst are mixed) and the time the setting reaction has proceeded to the point at which it is no longer practical to perform further physical work upon the system, e.g., reform it, for its intended purpose. When the reaction has proceeded to this later point the material is said to have reached its "gel point." The working time preferably provides enough time to mix and place the composition into its desired form. For many dental impression compositions and applications the working time under conditions of use is preferably greater than 30 seconds, more preferably greater than 1 minute and most preferably greater than 2 minutes.

The terms "set time" or "setting time" as used herein, refer to the time at which sufficient curing has occurred so that essentially the material's final cured-state properties are obtained. For a silicone impression material the set time is that time at which one may remove the material from the surface being replicated without causing permanent deformation of the silicone material. The setting time may be approximated, for example, by measuring the torque of the reacting composition on a oscillatory rheometer. When the torque value reaches a maximum value the material is said to be fully set. An arbitrary torque value which is less than the typical maximum value (e.g. 90% of the maximum value) may alternatively be used as a practical approximation of the set time. In general, shorter setting times are preferred over longer setting times. For dental impression compositions the setting time occurs at a time preferably less than 10 minutes after initiation of the reaction. More preferably the setting time is less than the sum of 5 minutes plus the working time. Most preferably the setting time is just longer than the desired working time.

As used herein, "solubility" means the capability of a substance to form a solution, i.e., either a true solution or a colloidal solution. A true solution is a uniformly dispersed mixture at the molecular or ionic level of one or more substances (the solute) in one or more substances (the solvent). A colloidal dispersion is often called a solution. Since colloidal particles are larger than molecules it is strictly incorrect to call such dispersions solutions; however this term is widely used in the literature, especially when the mixture is only slightly milky. As used herein, "dispersibility" means the capability of a substance to form a dispersion, i.e., a two-phase system where one phase consists of finely divided particles (often in the colloidal size range) distributed throughout a bulk substance, the particles being the disperse or internal phase and the bulk substance the continuous or external phase.

DETAILED DESCRIPTION OF THE INVENTION

The present invention provides novel hydrosilation-curable compositions, the cure of which can be monitored visually, comprising: (1) a multiply-ethylenic compound; (2) a compound containing a multiplicity of silicon-bonded-hydrogen groups; (3) a metal or metal complex capable of catalyzing a hydrosilation reaction; and (4) one or more cure-indicating dye compounds with light absorption or emission in the visible spectrum (i.e., 400–800 nm) that exhibit a color (including fluorescence) change in the presence of a silicon-bonded-hydrogen compound and a precious metal hydrosilation catalyst. The cure-indicating dye provides the composition with an initial pre-cure color (which color optionally can be mixed with a colored non-cure-indicating dye or pigment) and a different post-cure color. As a result of this change in color, the setting reaction or curing of the composition can be monitored visually. For example, this cure indication prompts the user to avoid exceeding the working time of the composition or to avoid prematurely removing or stressing the composition prior to its being fully set.

In the practice of the present invention, the curable composition can be a multiple-part composition cured by combining crosslinking agents and catalysts or a single-part composition cured by heating and/or exposure to actinic radiation or electron beam energy. Presently most preferred for dental applications are two-part addition-cure compositions of the room temperature vulcanizing ("RTV") variety. The composition contains a "curable silicone polymer," that is, a polysiloxane having two or more functional groups, e.g., vinyl groups, which enable the polymer to be polymerized or cured to a state of higher molecular weight. Suitable silicone polymers are well-known in the art and are described, for example, in "Silicones," *Kirk-Othmer Encyclopedia of Chemical Technology*, 3rd Ed., 20, 922–962 (1982).

Suitable ethylenic compounds for use in the present invention include those compounds which undergo a crosslinking reaction with a silicon-bonded-hydrogen compound (alternatively referred to as the "SiH compound" or "crosslinker") in the presence of a hydrosilation catalyst. Typically, the crosslinking reaction is facilitated by a catalyst compound and may be affected by temperature (e.g., the reaction may proceed at a somewhat greater rate at an elevated temperature or alternatively may be initiated at an elevated temperature). Preferred ethylenic compounds include monomers, oligomers or polymers which comprise pendant or terminal ethylenic "functional" groups (i.e., groups which "function" by reacting with the aforementioned SiH compound in the presence of a catalyst) such as vinyl, alkenyl or cycloalkenyl groups. Alternatively, the functional group may be situated along the polymer chain (i.e., along the backbone) and not be in a pendant position. Of these, vinyl groups are more preferred, and terminal vinyl groups are most preferred. It is understood that, in general, the cured composition's backbone "network" or "structure" comprises both the formerly ethylenic compound and the compound which contained the SiH group. It is understood that either compound could be employed in greater or lesser proportion or have greater or lesser initial molecular weight. Furthermore, depending on the combination of ethylenic compound and SiH compound, one could utilize a broad variety of "backbones" in these compounds and thereby achieve a broad variety of cured compositions having a range of physical properties.

Compounds containing aliphatic unsaturation which are useful in the present invention have olefinic or acetylenic unsaturation. These compounds are well-known in the art of hydrosilation and are disclosed in such patents as U.S. Pat. No. 3,159,662 (Ashby), U.S. Pat. No. 3,220,972 (Lamoreaux), and U.S. Pat. No. 3,410,886 (Joy). In instances where these unsaturated compounds contain elements other than carbon and hydrogen, it is preferred that these elements be either oxygen, nitrogen, silicon, halogen, or a combination thereof. The unsaturated aliphatic compound must contain two or more carbon-to-carbon multiple bonds. Representative examples of the aliphatically unsaturated hydrocarbons which can be employed include diolefins, for example, divinylbenzene, and 1,5-hexadiene. The unsaturated aliphatic compounds can have up to 20 to 30 carbon atoms, or more.

Oxygen-containing unsaturated aliphatic compounds can also be used, especially where the unsaturation is ethylenic, such as divinylether, diallyl ether of ethylene glycol, diallyl ether, diallyl adipate, resorcinol, diallyl ether ω-undecenyl, ω-undecylenate (10-undecenoate), allyl acrylate, allyl methacrylate, and linolenic acid methyl ester.

Halogenated derivatives of the previously mentioned unsaturated aliphatic compounds can be employed, including acyl chlorides as well as compounds containing a halogen substituent on a carbon atom other than a carbonyl carbon atom. Unsaturated compounds containing nitrogen substituents are also useful in the practice of the present invention.

Other unsaturated compounds useful in the practice of the present invention include polymers containing aliphatic unsaturation, such as the polyester resins prepared from polybasic saturated or unsaturated acids with polyhydric unsaturated alcohols, and the polyester resins prepared by reacting unsaturated polybasic acids with saturated polyhydric alcohols.

As previously mentioned, one presently preferred class of compounds for use in the present invention comprises a silicone backbone and two or more functional groups. One typical silicone composition is the polysiloxane referred to earlier and as depicted in formula F1.

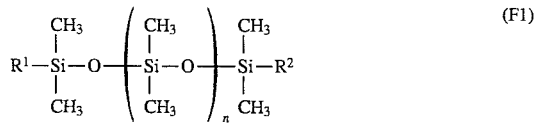

(F1)

Usually these polymers are made by an equilibrium process from other siloxanes and typically range in viscosity from about 0.01 Pa s to 2500 Pa s. Additional particularly useful unsaturated compounds which contain silicon are disclosed in U.S. Pat. No. 4,916,169 (Boardman et al.) which is herein incorporated by reference. The preferred molecular weight of the polysiloxane often depends upon the desired viscosity of the composition prior to crosslinking. In general, as the molecular weight is increased the viscosity of the uncrosslinked composition increases correspondingly. For uses as molding compositions, the average value of n preferably is between 10 and 6000. More preferably the average value of n is between 50 and 2000, and most preferably the average value of n is between 100 and 1000. Mixtures of more than one molecular weight may likewise be utilized.

The groups $R^1$ and $R^2$ of formula (F1) represent the "terminal" portions of the polymer chain and are often the sites for the attachment of functional groups, i.e., groups which participate in the crosslinking reaction. It is also contemplated that one or more sites depicted in formula (F1) as having non-functional methyl groups might instead contain a functional group and that $R^1$ and/or $R^2$ then may comprise a non-functional group such as a methyl group or another monovalent hydrocarbyl or halogenated monovalent hydrocarbyl group as listed below. Therefore, formula (F1) is intended merely to illustrate a "typical" polysiloxane polymer with terminal functional groups. The site of attachment of the two or more functional groups may be varied as desired and is not believed presently to be of essential importance to the practice of the present invention. The two or more functional groups are in general unsaturated aliphatic groups having 2 to 20 carbon atoms, such as alkenyl groups including vinyl, allyl, butenyl, propenyl, isopropenyl, and hexenyl groups or cycloalkenyl groups including cyclohexenyl, cyclopentenyl, cycloheptenyl and cyclooctenyl groups. A preferred unsaturated aliphatic group is vinyl. Most preferably, both $R^1$ and $R^2$ are vinyl groups and are located in terminal positions as depicted in (F1).

When special properties are needed, other non-functional monovalent hydrocarbyl and halogenated monovalent hydrocarbyl groups may be substituted for the methyl groups of formula (F1). For example, alkyl groups having 1 to 18 carbon atoms, e.g., methyl, ethyl, propyl, butyl, hexyl, dodecyl, octyl, and octadecyl; cycloalkyl groups having 5 to 7 ring carbon atoms, e.g., cyclohexyl and cycloheptyl; aryl groups having 6 to 18 carbon atoms, e.g., phenyl, naphthyl, tolyl, xylyl; aralkyl groups including benzyl, β-phenylpropyl, β-phenylethyl, and naphthylmethyl; alkoxy groups having 0 to 18 carbon atoms such as hydroxy, methoxy, ethoxy, and dodecyloxy; and halo-substituted hydrocarbon groups such as dibromophenyl, chloromethyl, 3,3,3-trifluoropropyl and chlorophenyl may be employed in place of all or some of the methyl groups of formula (F1).

Another compound useful in this invention is a branched polysiloxane having the general formula:

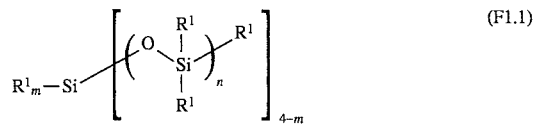

(F1.1)

wherein each $R^1$ is a functional group or a nonfunctional group as defined above and wherein at least two but preferably not more than one-half of all the $R^1$ groups in the siloxane are functional groups, m represents 0, 1, 2, or 3, and n represents a number having an average value from 1 to about 10,000. It is understood that compounds containing more than one branch point as depicted in (F1.1) may be employed.

A particularly interesting class of siloxane polymers useful as suitable ethylenic compounds in this invention and which contain the functionality described in F1.1. are the MQ resins. These polymers contain tetrafunctional $SiO_{4/2}$ (Q units) and $R^aR^bR^cSiO_{1/2}$ (M units) where the $R^a$, $R^b$, and $R^c$ are vinyl, methyl, phenyl, ethyl, hydroxy, or hydrogen. MQ resins where $R^a$ and $R^b$ are methyl and Rc is vinyl are most suitable for use as ethylenic compounds in this invention. Typically these would not be used as the only ethylenic compound in the formulation, but rather in combination with other ethylenic compounds, especially the vinyl terminated polydimethylsiloxane polymers shown in F1 where $R^1$ and $R^2$ are vinyl. The use of certain of these polymers in dental impression materials is disclosed in U.S. Pat. No. 5,403,885 and in the international patent application WO 93/17654.

The preferred amount of the polysiloxane component will vary depending upon the desired physical properties of the silicone composition (such as the desired uncured viscosity, cured hardness, etc.). In part due to the wide range of acceptable molecular weights for the polymer component and the many types of adjuvants which may be added to the polymer this amount will vary widely. The presently preferred amount of polymer component is between 5% and 99% by weight. More preferably the polymer component is between 20% and 90% by weight. Most preferably the polymer component is between 20% and 80% by weight.

The crosslinker component contains at least two silicon-hydrogen linkages and can be a polymeric compound or a compound that is not polymeric. These compounds are well known in the art and are disclosed, for example in U.S. Pat. Nos. 3,159,662 to Ashby; 3,220,972 to Lamoreaux; and 3,410,886 to Joy which are herein incorporated by reference.

Some classes of compounds having at least two silicon-bonded hydrogen atoms which can be used in the invention are:

(a) organohydrosilanes having the empirical formula,

(F2)

wherein each $R^3$ can be the same or different and represents an organic group, preferably selected from the group consisting of monovalent hydrocarbyl groups, monovalent alkoxy hydrocarbyl groups and halogenated monovalent hydrocarbyl groups, c represents an integer having a value at least 1, a represents an integer having a value at least 2, and the sum of a and b equals the sum of 2 and two times c;

(b) organohydrocyclopolysiloxanes having the empirical formula,

$$H_d R^3_e (SiO)_f \tag{F3}$$

wherein $R^3$ is as defined above, f represents an integer having a value from 3 to 18, d represents an integer having a value at least 2 and preferably less than or equal to f, and the sum of d and e equals two times f; and (c) organohydropolysiloxane polymers or copolymers having the empirical formula,

$$(H)_g (R^3)_h Si_j O_{(j-1)} \tag{F4}$$

wherein $R^3$ is as defined above, j represents an integer having a value from 2 to 10,000, g represents an integer having a value at least 2 and less than or equal to j, and the sum of g and h equals the sum of 2 and two times j.

Among the groups represented by $R^3$ include, for example, straight-chain and branched alkyl groups having 1 to 18 carbon atoms, e.g., methyl, ethyl, propyl, butyl, hexyl, dodecyl, octyl, and octadecyl, cycloalkyl groups having 5 to 8 ring carbon atoms, e.g., cyclohexyl and cyclooctyl, aryl, aralkyl, and alkaryl groups having 6 to 18 carbon atoms, e.g., phenyl, naphthyl, tolyl, xylyl, benzyl and phenylethyl, and halo-substituted groups thereof, e.g., chloromethyl, chlorophenyl, and dibromophenyl. Preferably, the $R^3$ group includes methyl and phenyl. The $R^3$ group can also be an unsaturated aliphatic group having 2 to 20 carbon atoms, such as alkenyl or cycloalkenyl, e.g., vinyl, allyl and cyclohexenyl. When the $R^3$ group is a group with aliphatic unsaturation, the silicon compound containing silicon-hydrogen linkages can be reacted with itself to form a polymer.

Another compound having silicon-bonded hydrogen useful in this invention is a branched organohydropolysiloxane having the general formula:

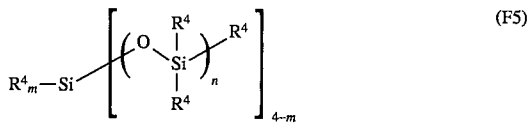

$$R^4_m-Si\left[\left(O-\underset{\underset{R^4}{|}}{\overset{\overset{R^4}{|}}{Si}}-R^4\right)_n\right]_{4-m} \tag{F5}$$

wherein each $R^4$ is as defined above for $R^3$ and wherein at least two but preferably not more than one-half of all the $R^4$ groups in the siloxane being hydrogen, m represents 0,1,2, or 3, and n represents a number having an average value from 1 to about 10,000. It is understood that compounds containing more than one branch point as depicted in (F5) may be employed.

Also useful in the present invention as compounds containing a multiplicity of silicon-bonded-hydrogen groups and which contain the functionality described in (F5) are the MQ resins. These polymers contain tetrafunctional $SiO_{4/2}$ (Q units) and $R^d R^e R^f SiO_{1/2}$ (M units) where the $R^d$, $R^e$, and $R^f$ are vinyl, methyl, phenyl, ethyl, hydroxy, or hydrogen. MQ resins where $R^d$ and $R^e$ are methyl and $R^f$ is hydrogen are most suitable for use as ethylenic compounds in this invention. Typically these would not be used as the only crosslinker component in the formulation, but rather in combination with other crosslinker components, especially the organohydropolysiloxane copolymers shown in (F4).

The amount of the crosslinker component should be sufficient to provide the desired degree of crosslinking of the silicone composition. In part due to the wide range of acceptable molecular weights for the polymer component and/or the crosslinker component, it is presently believed that this amount is best described in terms of the ratio of SiH groups to functional (e.g., vinyl) groups in the composition. The presently preferred ratio of SiH groups to functional groups ("SiH:F") is between 1:1 and 20:1. More preferably the SiH:F ratio is between 1:1 and 10:1. Most preferably the SiH:F ratio is between 1.3:1 and 4:1. The presently preferred amount of crosslinker component is between 0.2% and 90% by weight. More preferably the crosslinker component is between 0.2% and 20% by weight. Most preferably the crosslinker component is between 0.2% and 10% by weight.

Suitable hydrosilation catalysts for use in the present invention include those compounds which promote or facilitate the addition reaction between the ethylenic groups and the silicon-bonded-hydrogen groups. Examples of suitable catalysts include platinum or platinum compound catalysts exemplified by chloroplatinic acid, a complex of chloroplatinic acid and an alcohol, a complex of platinum and an olefin, a complex of platinum and a ketone, a complex of platinum and a vinylsiloxane, colloidal platinum, a complex of colloidal platinum and a vinylsiloxane etc., palladium or palladium compound catalysts exemplified by tetrakis (triphenylphosphine) palladium, a mixture of palladium black and triphenylphosphine, etc.; or rhodium or rhodium compound catalysts. Also suitable for use in the present invention are radiation activated hydrosilation catalysts. For example, one may employ: ($\eta^4$-cyclooctadiene)diarylplatinum complexes (as described in U.S. Pat. No. 4,530,879, Drahnak, which is herein incorporated by reference); ($\eta^5$-cyclopentadienyl)trialkylplatinum complexes (as described in U.S. Pat. No. 4,510,094, Drahnak, which is herein incorporated by reference); or ($\eta^5$-cyclopentadienyl)tri($\sigma$-aliphatic)-platinum complexes and a sensitizer that is capable of absorbing visible light (as described in U.S. Pat. No. 4,916,169, Boardman et al., which is herein incorporated by reference) with traditional vinylsiloxane polymers and crosslinkers. Platinum or platinum compound catalysts are presently preferred. Alternatively, Pt(II) beta-diketonate complexes as disclosed in U.S. Pat. No. 5,145,886 or the photohydrosilation catalyst systems described in U.S. patent application Ser. Nos. 07/626,904 and 07/627,009 are suitable for use in the present invention, both pending.

For dental molding compositions, "Karstedt" type catalysts as described below are presently most preferred. Karstedt platinum catalysts are described in U.S. Pat. Nos. 3,715,334, 3,775,452 and 3,814,730 which are herein incorporated by reference. In general, to produce a Karstedt catalyst, there must be utilized (A) platinum halide, and (B) a complexing material in the form of an unsaturated organosilicon material selected from:

(a) unsaturated silanes having the empirical formula,

$$R_a R'_b Si_c X_z \tag{F6}$$

where R is free of aliphatic unsaturation and selected from monovalent hydrocarbon radicals, R' is selected from monovalent aliphatically unsaturated hydrocarbon radicals, X is a hydrolyzable radical, c is an integer having an average value of at least 1, b is an integer having an average value greater than or equal to 2, and the sum of a plus b plus z equals the sum of 2 and two times c for a linear or branched silane and the sum of a plus b plus z equals two times c for a cyclic silane;

(b) unsaturated linear or branched siloxanes of the empirical formula, $$R_dR'_eSi_fO_{(f-1)} \tag{F7}$$

where R and R' are as defined above, f is an integer having an average value of between 2 and 10,000, e is an integer having an average value greater than or equal to 2 and the sum of d and e equals the sum of 2 and two times f; and (c) unsaturated cyclic siloxanes of the empirical formula, $$R_dR'_eSi_fO_f \tag{F8}$$

where R and R' are as defined above, e is an integer having an average value greater than or equal to 2, f is an integer having an average value from 3 to 18, and the sum of d and e equals two times f.

A Karstedt catalyst can be made by (1) effecting contact between an unsaturated organosilicon material as defined by formula (F6), (F7) or (F8) above, and a platinum halide to provide for the production of a mixture having a concentration of available inorganic halogen, (2) treating the resulting mixture of (1) to effect the removal of available inorganic halogen, and (3) recovering from (2), a platinum-siloxane complex having available inorganic halogen of less than about 0.1 gram atoms of halogen per gram atom of platinum. Preferably the complex is substantially halogen free. As used herein, the term "available inorganic halogen," will designate halogen that can be detected by a modification of ASTM designation D-1821-63 for "Inorganic Chloride." The procedure is substantially as described, except there is utilized in place of acetone a mixture of glacial acetic acid and acetone. The procedure employed for determining gram atoms of platinum in the platinum-siloxane complexes was Atomic Absorption Spectroscopy. For example, the method of R. Dockyer and G. F. Hames, Analyst, 84, 385 (1959).

Radicals included by R in formulas F6, F7, and F8 are, for example, alkyl radicals such as methyl, ethyl, propyl, isobutyl, 2-ethylhexyl, dodecyl, etc.; cycloalkyl radicals such as cyclohexyl, cycloheptyl, etc.; aryl and alkaryl radicals such as phenyl, naphthyl, tolyl, xylyl, and the like; aralkyl radicals such as benzyl, tolylethyl, phenylpropyl, etc. Radicals included by R' in formulas F6, F7 and F8 are, for example, aliphatically unsaturated radicals such as ethynyl, 2-propynyl, etc.; vinyl, allyl, 10-undecenyl, and cycloalkenyl radicals, such as cyclopentenyl, cyclohexenyl, cycloheptenyl, cyclooctenyl, and the like.

Unsaturated silanes included by formula (F6) are, for example, tetravinylsilane, triallylmethylsilane, divinyldimethylsilane, trivinylphenylsilane, divinylmethylphenylsilane, divinylmethylethoxysilane, divinylmethylacetoxysilane, and the like.

Included by the unsaturated siloxanes of formula (F7) are, for example, disiloxanes of the formula, $$R_gR'_hSiOSiR'_{h'}R_{g'} \tag{F9}$$

where R, R', are as defined above, the sum of h and h' is an integer with a value of at least two; the sum of g and h is equal to 3; and the sum of g' and h' is equal to 3. For example, there are included as disiloxanes of formula (F9), 1,1-divinyltetramethyldisiloxane, 1,3-divinyltetramethyldisiloxane, hexavinyldisiloxane, 1,1,3-trivinyltriethyldisiloxane, 1,1,3,3-tetravinyldimethyldisiloxane, 1,3-divinyl,-1,3-dimethyl,-1,3-diphenyldisiloxane, etc.

There are also included by the unsaturated siloxanes of formula (F8), cyclopolysiloxanes. For example, there is included 1,3,5-trivinyl-1,3,5-trimethylcyclotrisiloxane, 1,3,5,7-tetraallyl-1,3,5,7-tetraphenylcyclotetrasiloxane, 1,3-divinyloctamethylcyclopentasiloxane, etc.

Preferably the above-described platinum-siloxane complexes of platinum and organosiloxanes of formula (F7) and (F8), are made in accordance with the practice of the invention, as previously described, utilizing a platinum halide, and an unsaturated linear, branched or cyclic siloxane of formula (F7) or (F8) having at least one structural unit of the formula,

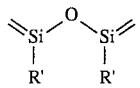 (F10)

where the unsatisfied valences ("Si≡") of the above structural unit can be satisfied by R, R' and oxygen radicals and where R and R' are as previously defined. Most preferably R' is a vinyl group.

The platinum halides which can be employed in the practice of the invention are, for example, $H_2PtCl_6 \cdot nH_2O$ and metal salts such as $NaHPtCl_6 \cdot nH_2O$, $KHPtCl_6 \cdot nH_2O$, $Na_2PtCl_6 \cdot nH_2O$, $K_2PtCl_6 \cdot nH_2O$. In addition, $PtCl_4 \cdot nH_2O$ and platinous type halides such as $PtCl_2$, $Na_2PtCl_4 \cdot nH_2O$, $H_2PtCl_4 \cdot nH_2O$, $NaHPtCl_4 \cdot nH_2O$, $KHPtCl_4 \cdot nH_2O$, $K_2PtBr_4$ and platinum halide complexes with aliphatic hydrocarbon as taught in Ashby U.S. Pat. Nos. 3,159,601 and 3,159,662, for example $[(CH_2=CH_2)PtCl_2]_2$; $(PtCl_2C_3H_6)_2$, etc. may be employed. Other platinum halides which can be utilized are shown by Lamoreaux U.S. Pat. No. 3,220,972, such as the reaction product of chloroplatinic acid hexahydrate and octyl alcohol, etc.

The amount of the platinum complex component should be sufficient to provide the desired degree of crosslinking of the silicone composition within a reasonable time. In part due to the wide range of acceptable molecular weights for the polymer component, it is presently believed that this amount is best described in terms of the ratio of Pt atoms to functional groups in the composition. The presently preferred ratio of Pt atoms to functional groups ("Pt:V") is between 1:2 and 1:2000. More preferably the Pt:V ratio is between 1:10 and 1:1000. Most preferably the Pt:V ratio is between 1:30 and 1:500. Preferably, the catalyst is present in an amount from about 5 to about 1000 parts by weight per 1,000,000 parts by weight of the total composition, more preferably from about 20 to 500 parts by weight per 1,000, 000 parts by weight of the total composition.

A "cure-indicating dye" is added to the curable composition to provide a visual indication of the extent of the hydrosilation reaction (e.g., extent of the crosslinking reaction). The cure-indicating dye exhibits a color change in the presence of a silicon-bonded-hydrogen compound and a precious metal hydrosilation catalyst and is characterized in a curable composition by having a first color before the cure reaction is effected and a second color after the cure reaction has been effected. Here "color" is taken to include visible fluorescence. The first color and second color are different and may be observed readily in the composition using the naked eye or a suitable instrument such as a spectrophotometer, colorimeter, or fluorimeter. Preferably, the difference in color may be observed readily using the naked eye by comparing the composition's second color to a reference color standard (e.g., a printed card, printed label or colored plastic part such as a colored plastic dental impression tray) that approximates either the composition's first color (i.e., a color mis-match is observed) or, more preferably, the composition's second color (i.e., a color match is observed). Similarly, the composition's second color may be compared to another composition that approximates the first composition's second color. For example, a commonly employed dental impression technique involves a "two-phase" system comprising a "putty" material and a separate "wash" material. In the present invention, one may choose to add a cure-indicating dye to either or both materials. For example, one of these materials (e.g., the wash) could contain a cure-indicating dye and change color upon curing to match the unchanging color of the other material (e.g., the putty). Alternatively, the putty and wash could each contain a different cure-indicating dye (thus having different initial colors) and change color upon curing to "match" each other. More preferably, the color change is pronounced such that the color change may be readily "recognized" by an observer even without the need for a reference color standard.

The dye's first color (e.g., before the cure reaction is effected) is typically fairly intense and may occupy virtually any visibly observable chroma. The dye's second color (i.e., after the cure reaction is effected) may be either a different color or be no color at all (i.e., the cure-indicating dye has been "bleached" to a colorless state and the natural color of the composition without the dye is observed). It is also expected that a suitable cure-indicating dye for use in the present invention may change from a visibly colorless state to a colored dye as a result of the curing reaction. For example, a colorless dye having strong near-infrared absorption may change to a visibly light absorbing dye, etc. Change of fluorescence color or intensity is another option.

The color change of this invention is correlatable with the extent of the hydrosilation reaction (e.g., correlatable with the extent of cure of the curable composition). The rate of color change can be adjusted depending on the particular cure-indicating dye employed, the amount of cure-indicating dye employed (relative to the other active components of the composition), and/or whether other indicator adjuvants are present in the composition. Similarly, the time at which the color change occurs relative to the crosslinking reaction can be adjusted. As will be demonstrated below this makes it possible to provide compositions which reproducibly exhibit a color change at virtually any desired point in the cure reaction.

Two-part curable compositions typically are formulated to be "shelf stable" (i.e., storage stable) for relatively long periods of time prior to being combined into one part. This may be accomplished, for example, by separating the catalyst component from the crosslinker component. The curing reaction is begun by mixing the two parts together. This may be done manually (e.g., by hand mixing or kneading the two pastes together until one homogeneous paste is formed) or by employing a static mixer or other mechanical mixer.

The working time of a two-part material refers to the time between the initiation of the setting reaction, e.g., when the vinyl-containing organopolysiloxane, the organohydropolysiloxane, and the platinum catalyst are mixed together, and the time the setting reaction has proceeded to the point at which it is no longer practical to perform further physical work upon the system, e.g., reform it, for its intended purpose. When the reaction has proceeded to this later point the material is said to have reached its gel point. The working time preferably provides enough time comfortably to mix and place the composition into its desired form but not so much time that the setting time is delayed unreasonably. For dental impression compositions the working time under conditions of use is preferably greater than 30 seconds, more preferably greater than 1 minute and most preferably greater than 2 minutes. Longer working times may also be acceptable. An indication of the end of the working time may be accomplished by adjusting the timing of the color change to coincide with or just precede the onset of the gel point of the material. This indication is very useful as it serves to warn the user visually of the onset of the gel and the finish of the working time. If desired, this color change can be adjusted to occur a few moments before this gel point, thus providing a longer warning period and allowing the user time to hurry, if need be, to finish the procedure or operation.

The setting time of an impression material refers to the time at which sufficient curing has occurred to allow removal of the silicone impression material from the surface being replicated without causing permanent deformation of said silicone material. The setting time of a coating refers to the time at which sufficient curing has occurred to allow the coating to be further processed or otherwise used for its intended purpose without physical damage to the coating. For an impression material, the setting time may be approximated by measuring the torque of the reacting composition by means of an oscillatory rheometer held at the desired temperature (e.g., held at the same temperature as would be encountered in use). As the material cures the torque value rises. When the torque reaches a maximum value the material is said to be fully set. For practical use of dental impression compositions, and for purposes of this invention, the point in time where the torque reaches 90 percent of its maximal value is defined as the setting time (this time is also referred to as "T90"). In general, shorter setting times are preferred over longer setting times. For dental impression compositions the setting time is preferably less than 10 minutes. More preferably the setting time is less than the sum of 5 minutes plus the working time. Most preferably the setting time is just longer than the desired working time. An indication of the arrival of the set time may be accomplished by adjusting the timing of the color change to coincide with or come just after the set time of the material. This visual indication is very useful as it serves to prompt the user of the achievement of the set and prevents undesirable and inadvertent removal or distortion of the material prior to its being completely set. If desired, this color change can be adjusted to occur a few moments after the set time, thus providing a safety margin.

For dental impression materials a cast of the dental tissue is often fabricated by pouring a liquid plaster, wax, or other hardenable material (e.g., a curable liquid epoxy material) into the set impression. Unfortunately, the surface of the cast can be marred if the impression material evolves gas during the time that the casting material is in contact with the impression and is itself hardening. The evolved gas can form bubbles on the surface of the casting material and displace the casting material from the surface being replicated forming a permanent defect in the cast. To avoid this problem it is customary to delay the pouring of the cast until well after the impression material is considered fully set This allows the impression material to completely de-gas before the casting material is poured into the impression. An indication of the arrival of this desired "pour time" might be accomplished by adjusting the timing of the color change to coincide with or come just after the end of deleterious gas evolution. This visual indication would be very useful as it would serve to prompt the user when the impression is safe to "pour up" and would prevent undesirable and inadvertent pouring of the casting material prior to complete gas evolution from the impression material.

In addition to monitoring the over-all cure reaction of a curable composition, the cure-indicating dye can also be used to indicate smaller localized regions on a curable composition where incomplete curing may have taken place. A recurring problem in dental impression making involves localized "poisioning" of the impression material which can delay or prevent curing of the material. This can occur, for example, when a "poison" is transferred from the surface being replicated to the impression material. This can happen when the dentist or assistant touches the surface of the tooth being impressioned with a contaminant and the contaminant then contacts the impression material. A common source of contaminant is a latex glove worn by the health care provider. The contaminants found on many latex gloves can delay or inhibit the cure of the silicone impression material. Another common source of contaminant includes acrylate-based and methacrylate-based dental composites and adhesives. Unfortunately, the transfer of a contaminant to the tooth surface cannot always be observed readily by the dentist. Likewise, localized defects caused by such contaminants may not be observed readily by looking at impressions made from traditional impression materials. However, if this localized delay occurs at a critical area the impression may be ruined, i.e., by not accurately representing the tooth being impressed, thereby causing a defective appliance (e.g., crown) to be produced. By using the cure-indicating dye of the present invention the health care provider can observe immediately any areas of the impression material that were contaminated. This can be accomplished visually by observing the surface of the impression material after it has been taken out of the mouth. If any areas exhibit unchanged color (or not completely changed color within about 30 seconds) then the impression may be bad and should be retaken. This saves the expense of making a crown or appliance that does not fit properly. In addition, the dentist thereby can detect recurring problems in his or her technique and adjust accordingly. Notably, certain regions of the impression may, even under optimal conditions, change color later than other regions. For example, the surface of a tooth is somewhat cooler than the surrounding gum tissue. This can cause the impression material adjacent to the tooth to set more slowly than the impression material adjacent to the gum tissue. This time delay is normally very short.

For coating compositions the cure-indicating dye may be employed to monitor (on-line or off-line) the coating process. Extent of cure, uniformity of cure, or overall coating quality may be monitored effectively by observing the composition's color. Preferably, a bleaching reaction will be employed in order to permit more thorough inspection and/or be inconspicuous for the intended use. For example, if one or more regions of the coating are not adequately cured (e.g., after being exposed to heat or visible or UV radiation) the color of the cure-indicating dye will remain unchanged. In addition, incomplete coatings may be similarly detected.

As previously mentioned, the cure-indicating dye provides a visual indication of the extent of cure of a curable composition. The color change of a dye may be observed using a suitable detection device such as an instrument (e.g., a spectrophotometer, fluorimeter or colorimeter) or the human eye. Depending on the intended use of the curable composition one or another detection device might be preferred. For example, for dental impression materials it is believed that observation of the color change will ordinarily be made by the naked eye (or optionally with assistance of corrective eyewear). For coating compositions (e.g., coatings on films used as release liners) it is believed that an off-line or on-line instrument can be utilized effectively to monitor the color change, and thus the cure, of the coating.

The amount of color change exhibited by the dye in a given composition need be only that amount of change that can be accurately measured or recognized by the detection device. It is understood that an instrument such as a spectrophotometer can detect fairly small color changes reproducibly. In contrast, the human eye may not notice or "remember" small color changes, especially when lighting is variable, although the human eye can detect very small color differences when two colors are compared directly (e.g., side by side comparison using a reference standard color). For dental impression materials the amount of color change is preferably sufficient that when one compares two colors side-by-side using the human eye a color difference is observable. More preferably, the color difference is readily observable, i.e., the difference is recognized after just a short observation time. Most preferably, the color change is observable without reference to a side-by-side comparison. That is, the observer can detect and recognize a difference between the second color and the "remembered" first color of the composition.

If desired, the recognition of a color change can be facilitated by providing a conveniently-located reference first or second color standard. The observer can compare the composition's color with the reference first or second color standard. This allows the observer to detect the color change more easily. If the reference standard matches the first color of the composition, the observer will detect a small change in color of the composition away from the reference first color standard. This first observation of a color difference can be used as the indication point of interest. If the reference standard matches the second color of the composition, the observer will be presented initially with a contrast in color between the reference standard and the curable composition (i.e., a color mismatch). This difference will become smaller, and preferably eventually disappear, as the composition cures. When the two colors eventually match the dye will have reached its second color and the indication point will have been obtained.

The reference standard may be provided, for example, as a separate color "chip" or printed card. This chip or card may be held against the curing composition for side-by-side comparison. Alternatively, for convenience when using dental impression materials, the reference standard may be applied directly to an impression tray (e.g., as a paint or label or as the natural color of the molded impression tray).

If desired the curable composition may also comprise an additional cure-indicating dye or dyes (i.e., the composition may comprise two or more different cure-indicating dyes). The additional cure-indicating dye or dyes may be used to provide additional indication points or to enhance one indication point. For example, a second cure-indicating dye and the first cure-indicating dye can together provide a first color to the curable composition (i.e., before curing has occurred). The first cure-indicating dye can be tailored to monitor one point in the cure reaction (e.g., the extent of working time) and the second cure-indicating dye can be tailored to monitor a different point in the cure reaction (e.g., the setting time). When the composition reaches the gel point (i.e., the extent of the working time) the first cure-indicating dye changes color or is bleached. This is observable as a color change in the composition (the composition retains the color of the second cure-indicating dye and any remaining color from the first cure-indicating dye). As the reaction proceeds and the set time is reached, the second cure-indicating dye changes color causing the composition to exhibit a third and final color.

In addition, if desired the curable composition may also comprise an additional non-cure-indicating dye or pigment. The non-cure-indicating dye or pigment modifies the color of the composition from its natural state and may combine with the first color of the cure-indicating dye to provide a first composition color that differs from both the first cure-indicating dye color and the natural composition color. For example, it is well known that a blue dye and a yellow dye will provide a green color. If the blue dye is a cure-indicating dye (e.g., a dye that changes from blue to colorless when the indication point is reached) and the yellow dye is a non-cure-indicating dye, the composition will have a green color initially and at the point of interest change to a yellow color. Other combinations of colors can be employed, depending on the desired color change and/or desired initial or final color.

The cure-indicating dye should be present in an amount sufficient to provide a visual indication of the extent of the hydrosilation reaction. The amount of cure-indicating dye needed will depend on a number of factors including the natural color of the composition and the desired amount of color change (e.g., less color change may be needed when the detector is more sensitive, more color change may be needed when the color change is poorly visible). In addition, the amount of dye needed will also depend on the dye's tinctorial strength. The cure-indicating dye should have enough tinctorial strength to color the composition effectively and provide for the necessary color change. A common measure of tinctorial strength is the dye's "extinction coefficient." In general, higher extinction coefficient dyes are preferred due to their greater contribution per molecule to color. Lower extinction coefficient dyes, while not preferred, may nevertheless be employed, usually at somewhat higher concentration. Preferred cure-indicating dyes for use in the present invention have a molar extinction coefficient in the visible spectrum of at least 1,000 $M^{-1} \times cm^{-1}$, more preferably at least 10,000 $M^{-1} \times cm^{-1}$, and most preferably at least 30,000 $M^{-1} \times cm^{-1}$. For use in dental impression materials, the mount of dye preferably should be a sufficient amount such that the dye's contribution to the composition's color can be easily observed using the naked eye. Preferred impression materials comprise between 0.0001 and 0.1 weight % cure-indicating dye (based on the total weight of the curable composition and when normalized to a dye having a molar extinction coefficient of 32,000 $M^{-1} \times cm^{-1}$), more preferably between 0.0003 and 0.03 weight % cure-indicating dye, and most preferably between 0.001 and 0.015 weight % cure-indicating dye. Those skilled in the art of dye chemistry will understand that for dyes with a lower molar extinction coefficient correspondingly greater amounts of cure-indicating dye will be required to achieve the same color intensity as a cure-indicating dye with a higher molar extinction coefficient. Preferred coating compositions comprise between 0.0002 and 0.2 weight % cure-indicating dye (based on the total weight of the coating composition but not including the weight of any volatile solvents that are not present when the coating's color is to be observed and when normalized to a dye having a molar extinction coefficient of 32,000 $M^{-1} \times cm^{-1}$), more preferably between 0.0006 and 0.06 weight % cure-indicating dye, and most preferably between 0.002 and 0.03 weight % cure-indicating dye. A maximum effective amount of a cure-indicating dye is an amount sufficient to allow visible (or, optionally, near-infrared) radiation to penetrate the coating to its full depth and provide a maximal signal consistent with there being a measurable signal from the entire working depth of the coating. Amounts in excess of an effective amount will tend to absorb all of the visible radiation in the upper portion of the coating and may provide no useful signal from the lower portion to indicate its thickness or extent of cure. When color is bleached upon cure, it becomes possible to monitor at greater depths. Amounts less than the maximum effective amount may be highly satisfactory or even preferred if it is desired that the coating weight be directly proportional to the initially measured or the final signal.

Preferred cure-indicating dyes change color very rapidly when the indication time (e.g., the working time, setting time, etc.) has been reached. The time between the onset of color change and the completion of the color change is referred to as the "transition time". For dental impression materials a "typical" working time is measured in minutes (e.g., 0.5 to 2 minutes). Based on this time frame preferred cure-indicating dyes used to monitor working time change color within a one minute period, more preferably within a 30 second period. Similarly, typical dental impression materials have a set time of 3 to 7 minutes. Based on this time frame preferred cure-indicating dyes used to monitor set time change color within a three minute period, more preferably within a two minute period, most preferably within a one minute period. When longer indication times are being monitored, a longer transition time (i.e., the time over which the cure indicating dye exhibits a change of color) can be tolerated. For coating compositions, preferred cure-indication dyes change color rapidly and most preferably exhibit a complete color change prior to the winding of the coated article. In this manner an inspection of the coated article may be made "on-line."

In addition to the above-mentioned requirements, the cure-indicating dye (which may be a liquid or solid) should be, and preferably is, soluble or dispersible in the composition being colored. A "soluble" cure-indicating dye, as used herein, is a cure-indicating dye that when mixed with the initial or uncured composition (including any optional solubilizing agents, e.g., cosolvents or surfactants, that are present in the composition) under the desired conditions of use dissolves to form a homogeneous colored mixture. Such conditions of use include temperature (e.g., over the temperature range encountered during use and cure of the composition), time (e.g., the amount of time the composition is in the uncured state), and concentration (e.g., the concentration of cure-indicating dye in the composition). A "dispersible" cure-indicating dye, as used herein, is a cure-indicating dye that when mixed with the composition (including any optional solubilizing agents, e.g., cosolvents or surfactants, that are present in the composition) under the desired conditions of use forms a macroscopically homogeneous colored mixture. The dye may be in the form of very small particles suspended in the composition, i.e., form a two-phase system where one phase consists of finely divided particles (often in the colloidal size range) distributed throughout a bulk substance, the particles being the disperse or internal phase and the bulk substance the continuous or external phase. The dye particle should be small enough that the dye colors the mixture and is capable of interacting with the composition to change color as desired. An "insoluble" or "nondispersible" dye proposed for cure-indication purposes, as used herein, is a potentially-cure-indicating dye that when mixed with the composition (including any optional cosolvents that are present in the composition) under the desired conditions of use forms a macroscopically heterogeneous mixture. A macroscopically heterogeneous mixture, as used herein, includes phase-separated liquid/liquid systems (e.g., oil and water); two-phase systems comprising a granular or powdery solid phase in a liquid; and two-phase systems comprising a suspension of large particles in a liquid, wherein the large particles do not color the composition or do not interact with the composition to change color as desired.

As previously mentioned the composition containing the cure-indicating dye may optionally comprise one or more suitable cosolvents. The cosolvents may be employed to facilitate the dissolution or suspension of the cure-indicating dye and/or other adjuvants in the composition, to facilitate uniform mixing of the reactants, or to adjust the composition's viscosity or flow. Suitable cosolvents for use with silicone compositions include aromatic hydrocarbons, such as xylene and toluene, aliphatic hydrocarbons, such as hexane and mineral spirits, and halogenated hydrocarbons, such as chlorobenzene and trichloroethane. It is desirable that the solvent be transmissive to visible light. The composition preferably contains less than about 70 weight percent cosolvent, more preferably less than 40 weight percent cosolvent, and most preferably less than about 10 weight percent cosolvent.

Preferred cure-indicating dyes are soluble or dispersible, more preferably soluble, in the curable composition without the presence of a cosolvent. The solubility or dispersibility of a dye can be adjusted, if needed or desired, by several means. For example, an otherwise insoluble or nondispersible dye may be "tethered" to another compound that has the necessary or desired solubility or dispersibility in the composition. Preferably, the tethered dye molecule will have characteristics of both compounds (i.e., the cure-indicating properties of the dye and the solubility characteristics of the other compound). The attachment or tethering may be covalent or ionic. For example, if ionic tethering is employed one may associate an otherwise insoluble cationic or anionic dye to a suitably soluble anion or cation, respectively. The tethering ion may be itself attached to the curable polymer. Alternatively, an otherwise insoluble neutral dye may be covalently attached to another component to render the resulting larger molecule soluble or dispersible in the composition. Typically this may be done by attaching the insoluble dye to the molecules of the composition, e.g., attaching the dye to the curable silicone polymer. Of course, one may also attach a soluble dye to the molecules of the composition. This may be desired in a situation where it is important that the dye not "leach out" or "bloom" from the cured composition (e.g., where toxicity or environmental issues are of concern).

Suitable cure-indicating dyes are soluble or dispersible, more preferably soluble, in the curable composition (including any optional solubilizing agents, e.g., cosolvents or surfactants, that are present in the composition) at a concentration sufficient to color the composition effectively. Preferably, the cure-indicating dye is soluble or dispersible in the composition at a concentration sufficient to color the composition effectively without the need to employ a cosolvent. More preferably, the cure-indicating dye is soluble or dispersible at a sufficient concentration such that the dye's contribution to the composition's color can be observed readily using the naked eye (or for a coating compositions using a suitable detection device).

As previously mentioned, suitable cure-indicating dyes for use in the present invention exhibit a color change in the presence of a multiply-silicon-bonded-hydrogen compound, a multiply-ethylenic compound, and a precious metal hydrosilation catalyst when the aformentioned compounds are allowed to react under the desired conditions of use (i.e., time, temperature, concentration in the composition, etc.). A simple and effective method of testing whether a particular dye is potentially suitable for use in the present invention (i.e., not yet considering solubility/dispersibility issues) involves mixing the dye with the following model compounds and observing whether or not the dye exhibits a color change. This model system differs substantially from the conditions that occur in a curable composition, since this model system does not undergo a "curing" reaction. Furthermore, and notably, a solvent system is used instead of the polymer composition of a curable composition. Dyes are evaluated according to the following test method (hereinafter referred to as the "pentamethyldisiloxane test"). First, 500 μg (micrograms) of dye is transferred to a 6 μl clear-glass, screw cap vial. Five hundred μl (microliters) of dichloromethane is then pipetted to the vial, followed by 100 μl of pentamethyldisiloxane. The dye, dichloromethane and pentamethyldisiloxane are mixed until homogeneous. To this solution is added an effective amount of a "hydrosilation catalyst solution." Suitable hydrosilation catalyst solutions and suitable effective amounts of such catalyst solutions for use in this test include the following catalyst solutions: (A) 25 μl of a catalyst solution comprising 25% by weight of a commercially available catalyst (PC075, available from United Chemical Technology, Inc., Bristol, Pa.) in dichloromethane; (B) 10 μl of a commercially available catalyst solution (PC072, available from United Chemical Technology, Inc., Bristol, Pa.); or (C) 10 μl of a Karstedt-type catalyst solution in toluene, wherein said catalyst comprises a complex of Pt° and 1.5 equivalents (1.5 g mols per g atom Pt) of divinyltetramethyldisiloxane and wherein said solution has between about 2 and 3 weight percent platinum. The United Chemical Technology catalyst solutions are further described at page 268 in *Silicon Compounds Register and Review—Silicones & Silicon-Containing Polymers—5th Edition*, edited by Roy Anderson, G. L. Larson and Craig Smith, Huls America Inc., Piscataway, N.J., which is herein incorporated by reference. The Karstedt-type catalyst solution in toluene is further described in Preparatory Example 1b and on page 13 of "Aspects of Some Divinylsiloxane Complexes of Platinum and Rhodium," PhD thesis by Nicholas John William Warhurst, University of Sussex, March 1990, which is herein incorporated by reference. The vial is capped, agitated for approximately 5 seconds at room temperature (25° C.) and the solution observed for color change (e.g., bleaching). Those dyes that exhibited a significant color change (e.g., bleaching) within 24 hours and preferably within less than about 10 minutes under these conditions are believed to be suitable candidates for use in the present invention (subject to their having the desired solubility or dispersibility in the composition as discussed above). To verify that the above test is being performed correctly (e.g., that the selected catalyst solution is active), one may repeat the above test using a dye which has been demonstrated to bleach under these conditions. For example, dye #2 of Table 1a is known to bleach in less than about 10 minutes under these conditions and is a suitable dye for use in this invention. In the event that the dye is not soluble in 500 μl of dichloromethane, then one may either utilize additional dichloromethane (i.e., sufficient to dissolve the dye) or utilize a different solvent which is capable of dissolving the dye, and which is verified to not interfere with the bleaching of dye #2 as indicated above.

The amount of color change exhibited by a particular cure-indicating dye may be measured using a visible light spectrophotometer in conjunction with the above test. A small-volume short-path-length cuvette containing 500 mg of dye, 500 ml of dichloromethane, and 100 μl of pentamethyldisiloxane is positioned in the spectrophotometer and measured for its absorptivity to visible, near-UV and near IR light. The path length (or if necessary the amount of dye) is chosen to provide absorbance less than 4.0 at $\lambda_{max}$. The absorbance is compared to that of a similar solution, but that contains 10 or 25 μl, as appropriate, of the previously mentioned catalyst solutions and has been allowed to "bleach" for about 10 minutes as described above). Preferred cure-indicating dyes for use in the present invention exhibit a 10-fold decrease in absorbance (as measured at $\lambda_{max}$) when tested in this manner (i.e., a loss of 90% in absorbance). More preferred cure-indicating dyes for use in the present invention exhibit a 100-fold decrease in absorbance when tested in this manner (i.e., a loss of 99% in absorbance). Most preferred cure-indicating dyes exhibit a 10-fold or 100-fold decrease in absorbance in less than about 5 minutes when tested in this manner.

A simple and effective method of establishing approximate timing signaled by a cure-indicating dye involves mixing the dye with the following model curable composition and observing whether or not the dye exhibits a color change at or near the time when the model curable composition sets, as determined by laboratory testing such as oscillatory rheometry. The model curable composition contains compounds selected to perform the function of the catalyst, the SiH compound, and the polymer compound. Dyes are evaluated according to the following test method. First, approximately 500 μg of dye is transferred to a 6 ml clear-glass, screw cap vial. One ml of stock composition B1 from Preparatory Example 2 is transferred to the vial via pipette or dropper, the solution is mixed with a spatula for 3 minutes and the mixture is examined visually for coloration of the resin and general solubility of the dye. If necessary, 1–2 drops (approximately 0.015 to 0.03 gms) of dichloromethane may be added to promote the solubility of less soluble dyes. One ml of stock composition C2 from Preparatory Example 2 is transferred to the vial and mixed with a small stick. The composition is placed against a white background and examined visually and manually for the time at which gelation occurs (as evidenced by an increase in viscosity and minimal flow when the vial is inverted) and the time at which the color changes. Those dyes that exhibit color change (e.g., bleaching) within 2 times the gel time are believed to be candidates for use in the present invention. This procedure may be repeated with various types and amounts of additives to adjust the time of color change for the intended use.

While not intending to be bound by theory, it is believed presently that suitable cure-indicating dyes include those dyes that are reduced (e.g., catalytically hydrogenated) in the presence of a silicon-bonded-hydrogen compound and a precious metal hydrosilation catalyst when the aformentioned compounds are allowed to react under the desired conditions of use (i.e., considering time, temperature, concentration in the composition, etc.). These reactions are exceedingly difficult to study in detail. It is presently believed that the reduction of the cure-indicating dye affects the chromophore of the dye, interrupting conjugation and thereby altering its apparent color. For example, it is known to the inventors that 2-Chloro-4-[[2-methyl-4-(diethylamino)phenyl]imino]-2,5-cyclohexadien-1-one is reduced to 2-Chloro-4-[[2-methyl-4-(diethylamino)phenyl]amino]-1-phenol in the presence of the silicon-bonded-hydrogen compound acting as a source of hydrogen, and a precious metal hydrosilation catalyst.

For dyes capable of cure-indication, it is believed that there is a competition for different reaction pathways involving the organohydropolysiloxane crosslinker. In a first pathway the SiH groups on the crosslinker react with the unsaturated groups on the organosiloxane, catalyzed by the Pt catalyst, to effect hydrosilation. In a second pathway the SiH groups on the crosslinker react with other SiH groups (or with sources of protons such as acids), also catalyzed by the Pt catalyst, to generate hydrogen gas. In general the first pathway is dominant when the three ingredients (e.g., vinyl polymer, organohydropolysiloxane crosslinker, and Pt catalyst) are first mixed. As the reaction proceeds the concentration of unsaturated groups falls dramatically relative to the generally more abundant SiH groups and the reaction pathway begins to favor hydrogen gas production. The hydrogen gas, in the presence of Pt catalyst, is believed to reduce (by catalytic hydrogenation) certain (and perhaps all) of the cure-indicating dyes of the present invention, resulting in a change in color of the dye. It is also believed that the propensity of the dye to be reduced has a strong impact on the timing of the color change (i.e., in relation to the timing of the hydrosilation cure reaction). Dyes that are very easily reduced (e.g., as indicated by cyclic voltammetry) will generally react and change color sooner than dyes which are less easily reduced. Other factors such as the ratio between SiH groups and unsaturated groups and/or the presence of adjuvants affect the relative rates of hydrosilation and hydrogen production. In this way the color change may be adjusted to coincide with the desired point in the curing reaction.

Suitable dyes for use in the present invention may be classified by their reducible chromophore into several generic groups. Representative of these groups include indoaniline dyes, indophenol dyes, quinone monoimine dyes, quinone diimine dyes, cyanine dyes, merocyanine dyes (a hybrid of a true cyanine dye and a true oxonol dye), cyclohexadienone dyes, iminocyclohexadienone dyes, imidazolylidinecyclohexadienone dyes, dihydronaphthalenone dyes, iminodihydronaphthalenone dyes, imidazolylidinedihydronaphthalenone dyes, cyclohexadienimine dyes, sulfone dyes including: aryl substituted bis trifluoromethylsulfonylhexatrienyl dyes, aryl substituted bis (trifluoromethylsulfonyl)butadienyl dyes, aryl substituted bis (fluorosulfonyl)hexatrienyl dyes, and aryl substituted bis (fluorosulfonyl)butadienyl dyes, oxazolone dyes, and ionic dyes including cationic dyes, anionic (e.g., oxonol) dyes, and betaine dyes. By "cationic dye" is meant an ionic dye having a cationic chromophore. By "anionic dye" is meant an ionic dye having an anionic chromophore. Neutral azo dyes and anthraquinone dyes, which do not pass the pentamethyldisiloxane test previously described, are not now believed to be suitable for use in the present invention.

As is well understood in this area, substitution is not only tolerated, but is often advisable. As a means of simplifying the discussion and recitation of certain terminology used throughout this document, the terms "group" and "moiety" are used to differentiate between chemical species that allow for substitution, or which may be substituted ("group"), and those which do not so allow or may not be so substituted. Thus when the term "group" is used to describe a chemical substituent, the described chemical material includes the basic group and that group with conventional substitution. Where the term "moiety" is used to describe a chemical compound or substituent, only an unsubstituted chemical material is intended to be included. For example, the phrase "alkyl group" is intended to include not only pure open-chain, branched, and cyclic hydrocarbon alkyl substituents, such as methyl, ethyl, propyl, isopropyl, tert-butyl, cyclohexyl, adamantyl, octadecyl, and the like, but also alkyl substituents bearing further substituents known in the art (e.g., silicon substituted, oxygen substituted, etc.). On the other hand, the phrase "alkyl moiety" is limited to the inclusion of only pure open-chain, branched and cyclic hydrocarbon alkyl substituents, such as methyl, ethyl, propyl, isopropyl, tertbutyl, cyclohexyl, adamantyl, octadecyl, and the like. As used herein, a "hydrocarbyl-containing group" is intended to include not only pure open-chain, branched, and cyclic hydrocarbyl substituents but also hydrocarbyl substituents which bear further substituents known in the art (e.g., silicon substituted, oxygen substituted, etc.) and/or which are linked to the basic compound by means of a heteroatom other than carbon (e.g., sulfur, oxygen, nitrogen and silicon).

One class of particularly suitable dyes may be represented by the following general formula (F11):

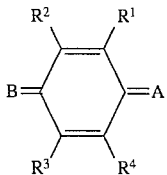

wherein:
each $R^1$, $R^2$, $R^3$, and $R^4$ group is independently hydrogen, halogen, a hydrocarbyl-containing group, or a heterocyclic group, preferably each $R^1$, $R^2$, $R^3$, and $R^4$ group is independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, carboxamide (—C(O)NR$^1$R$^2$), and wherein $R^1$ and $R^2$ or $R^3$ and $R^4$ may be connected to form a saturated or unsaturated ring, for example, $R^3$ and $R^4$ may be joined by or be a —$C_4H_4$—, —$(CH_2)_3$—, or —$C_3H_3N$— moiety; more preferably each $R^1$, $R^2$, $R^3$, and $R^4$ group is independently selected from the group consisting of: hydrogen, halogen, a $C_1$-$C_{10}$ alkyl, a $C_1$-$C_{10}$ alkoxy, a $C_5$-$C_8$ cycloalkyl, a $C_6$-$C_{10}$ aryl, a $C_2$-$C_{10}$ alkenyl, and a $C_1$-$C_{10}$ alkylamino, and wherein $R^1$ and $R^2$ or $R^3$ and $R^4$ groups may be connected to form a saturated or unsaturated 5 to 8 member ring, for example, $R^3$ and $R^4$ may be joined by a —$C_4H_4$— or —$C_3H_3N$— moiety; most preferably each $R^1$, $R^2$, $R^3$, and $R^4$ group is independently selected from the group consisting of: hydrogen, methyl, ethyl, propyl, tert.-butyl, methoxy, ethoxy, isopropoxy, tert.-butoxy, a $C_5$-$C_8$ cycloalkyl, a $C_6$-$C_{10}$ aryl, a $C_2$-$C_{10}$ alkenyl, a $C_1$-$C_{10}$ alkylamino, chlorine, and bromine, and wherein $R^3$ and $R^4$ may be joined by a —$C_4H_4$— or —$C_3H_3N$— moiety;

A is O, S, or NR$^{22}$, wherein $R^{22}$ is hydrogen, a hydrocarbyl-containing group, or a heterocyclic group, preferably $R^{22}$ is a group selected from the group consisting of: hydrogen, a $C_1$-$C_{20}$ alkyl, a $C_3$-$C_{18}$ cycloalkyl, a $C_6$-$C_{18}$ aryl, a $C_2$-$C_{18}$ alkenyl, a $C_6$-$C_{18}$ arylamino, and substituted sulfonyl; more preferably $R^{22}$ is selected from the group consisting of hydrogen and —$SO_2C_6H_5$; and B is any group capable of providing extended conjugation thereby rendering the dye capable of absorbing visible, near-UV, or near-infrared radiation including groups of formula D, E, F, H, or J, wherein D is represented by formula (F12):

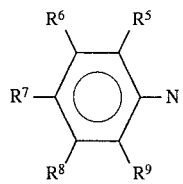

wherein:
each $R^5$, $R^6$, $R^7$, $R^8$, and $R^9$ group is independently hydrogen, halogen, a hydrocarbyl-containing group, or a heterocyclic group, preferably each $R^5$, $R^6$, $R^7$, $R^8$, and $R^9$ group is independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ is alkenyl, a $C_1$-$C_{20}$ alkylamino, a $C_6$-$C_{18}$ is arylamino, a $C_6$-$C_{18}$ aminoaryl, a $C_2$-$C_{20}$ di(hydrocarbyl)amino, morpholino, and alkylamido and wherein any two adjacent $R^5$, $R^6$, $R^7$, $R^8$, and $R^9$ groups may be connected to form a saturated or unsaturated ring, for example, $R^5$ and $R^6$ or $R^6$ and $R^7$ may be joined by or be a —$C_4H_4$— or —$C_3H_3N$— moiety; more preferably each $R^5$, $R^6$, $R^7$, $R^8$ and $R^9$ group is independently selected from the group consisting of: hydrogen, halogen, a $C_1$-$C_{10}$ alkyl, a $C_1$-$C_{10}$ alkoxy, a $C_5$-$C_8$ cycloalkyl, a $C_6$-$C_{10}$ aryl, a $C_6$-$C_{18}$ aryloxy, a $C_2$-$C_{10}$ alkenyl, a $C_1$-$C_{10}$ alkylamino, a $C_6$-$C_{18}$ arylamino, a $C_2$-$C_{20}$ di(hydrocarbyl)amino, morpholino, and alkylamido and wherein any two adjacent $R^5$, $R^6$, $R^7$, $R^8$, and $R^9$ groups may be connected to form a saturated or unsaturated 5 or 6 member ring; most preferably each $R^5$, $R^6$, $R^7$, $R^8$ and $R^9$ group is independently selected from the group consisting of: hydrogen, methyl, ethyl, propyl, butyl, methoxy, ethoxy, propoxy, a $C_5$-$C_8$ cycloalkyl, a $C_6$-$C_{10}$ aryl, benzyloxy, naphthyloxy, a $C_2$-$C_{10}$ alkenyl, N,N-dialkylamino, N-alkyl-N-arylamino, —N(Et)[((CH$_3$)$_3$C)$_2$(CH$_3$)$_1$SiOCH$_2$CH$_2$], chlorine, bromine, morpholino, and alkylamido and wherein $R^5$ and $R^6$ or $R^6$ and $R^7$ may be joined by or be a —$C_4H_4$—, —$(CH_2)_3$—, or —$C_3H_3N$— moiety;

E is represented by formula (F13):

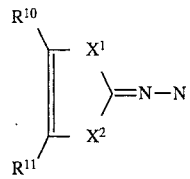

wherein:
$X^1$ is C(R$^{12}$)$_2$, S, NR$^{12}$, or O, more preferably $X^1$ is S or O, most preferably $X^1$ is S;

$X^2$ is C(R$^{12}$)$_2$, S, NR$^{12}$, or O, more preferably $X^2$ is C(R$^{12}$)$_2$ or NR$^{12}$, most preferably $X^2$ is NR$^{12}$; and each $R^{10}$, $R^{11}$ and $R^{12}$ group is independently hydrogen, a hydrocarbyl-containing group, or a heterocyclic group, preferably each $R^{10}$, $R^{11}$ and $R^{12}$ group is independently selected from the group consisting of: hydrogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, and wherein $R^{10}$ and $R^{11}$ may be connected to form or be a ring; more preferably each $R^{10}$, $R^{11}$ and $R^{12}$ group is independently selected from the group consisting of: hydrogen, a $C_1$-$C_{10}$ alkyl, a $C_1$-$C_{10}$ alkoxy, a $C_5$-$C_8$ cycloalkyl, a $C_6$-$C_{10}$ aryl, a $C_2$-$C_{10}$ alkenyl, and a $C_1$-$C_{10}$ alkylamino, and wherein $R^{10}$ and $R^{11}$ may be connected to form or be a ring; and most preferably each $R^{10}$, $R^{11}$ and $R^{12}$ group is independently selected from the group consisting of: hydrogen, methyl, ethyl, propyl, butyl, methoxy, ethoxy, propoxy, a $C_5$-$C_8$ cycloalkyl, a $C_6$-$C_{10}$ aryl, a $C_2$-$C_{10}$ alkenyl, a $C_1$-$C_{10}$ alkylamino, chlorine, and bromine, and wherein any two adjacent $R^{10}$, $R^{11}$, and $R^{12}$ groups may be joined by or be a —$C_4H_4$—, —$(CH_2)_3$—, or —$C_3H_3N$— moiety;

F is represented by formula (F14):

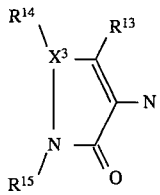

wherein:

$X^3$ is N or $CR^{16}$; and each $R^{13}$, $R^{14}$, $R^{15}$, and $R^{16}$ group is independently hydrogen, halogen, a hydrocarbyl-containing group, or a heterocyclic group and wherein any two adjacent $R^{13}$, $R^{14}$, $R^{15}$, and $R^{16}$ groups may be connected to form a ring, preferably each $R^{13}$, $R^{14}$, $R^{15}$, and $R^{16}$ group is independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino and wherein any two adjacent $R^{13}$, $R^{14}$, $R^{15}$, and $R^{16}$ groups may be connected to form a ring; more preferably each $R^{13}$, $R^{14}$, $R^{15}$ and $R^{16}$ group is independently selected from the group consisting of: hydrogen, halogen, a $C_1$-$C_{10}$ alkyl, a $C_1$-$C_{10}$ alkoxy, a $C_5$-$C_8$ cycloalkyl, a $C_6$-$C_{10}$ aryl, and a $C_2$-$C_{10}$ alkenyl; and most preferably each $R^{13}$, $R^{14}$, $R^{15}$, and $R^{16}$ group is independently selected from the group consisting of: hydrogen, methyl, ethyl, propyl, butyl, methoxy, ethoxy, propoxy, a $C_5$-$C_8$ cycloalkyl, and phenyl;

H is represented by formula (F16):

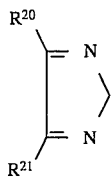

wherein:

each $R^{20}$ and $R^{21}$ group is independently hydrogen, halogen, a hydrocarbyl-containing group, or a heterocyclic group and wherein $R^{20}$ and $R^{21}$ may be connected to form a ring, preferably each $R^{20}$ and $R^{21}$ group is independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, morpholino, and furyl and wherein $R^{20}$ and $R^{21}$ may be connected to form or be a saturated or unsaturated ring; more preferably each $R^{20}$ and $R^{21}$ group is independently selected from the group consisting of: hydrogen, halogen, a $C_1$-$C_{10}$ alkyl, a $C_1$-$C_{10}$ alkoxy, a $C_5$-$C_8$ cycloalkyl, a $C_6$-$C_{10}$ aryl, a $C_6$-$C_{10}$ aryloxy, a $C_2$-$C_{10}$ alkenyl, a $C_1$-$C_{10}$ alkylamino, a $C_6$-$C_{18}$ arylamino, and 2-furyl; and most preferably each $R^{20}$ and $R^{21}$ group is independently selected from the group consisting of: hydrogen, methyl, ethyl, propyl, butyl, methoxy, ethoxy, propoxy, a $C_5$-$C_8$ cycloalkyl, a $C_6$-$C_{10}$ aryl, benzyloxy, naphthyloxy, a $C_2$-$C_{10}$ alkenyl, diethylamino, dimethylamino, chlorine, bromine, morpholino, acetamido, and 2-furyl; and J is represented by formula (F17):

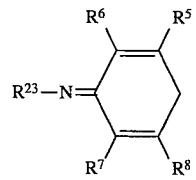

wherein:

each $R^5$, $R^6$, $R^7$ and $R^8$ group is independently hydrogen, halogen, a hydrocarbyl-containing group, or a heterocyclic group and wherein any two adjacent $R^5$, $R^6$, $R^7$ and $R^8$ groups may be connected to form a ring, preferably each $R^5$, $R^6$, $R^7$ and $R^8$ group is independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, morpholino, alkylamido and wherein $R^5$ and $R^6$ or $R^7$ and $R^8$ may be connected to form a ring, for example, $R^5$ and $R^6$ or $R^7$ and $R^8$ may be joined by or be a —$C_4H_4$—, —$(CH_2)_3$—, or —$C_3H_3N$— moiety; more preferably each $R^5$, $R^6$, $R^7$ and $R^8$ group is independently selected from the group consisting of: hydrogen, halogen, a $C_1$-$C_{10}$ alkyl, a $C_1$-$C_{10}$ alkoxy, a $C_5$-$C_8$ cycloalkyl, a $C_6$-$C_{10}$ aryl, a $C_6$-$C_{18}$ aryloxy, a $C_2$-$C_{10}$ alkenyl, a $C_1$-$C_{10}$ alkylamino, a $C_6$-$C_{18}$ arylamino, morpholino, acetamido and wherein $R^5$ and $R^6$ or $R^7$ and $R^8$ may be connected to form a 5 or 6 member ring; most preferably each $R^5$, $R^6$, $R^7$ and $R^8$ group is independently selected from the group consisting of: hydrogen, methyl, ethyl, propyl, butyl, methoxy, ethoxy, propoxy, a $C_5$-$C_8$ cycloalkyl, a $C_6$-$C_{10}$ aryl, benzyloxy, naphthyloxy, a $C_2$-$C_{10}$ alkenyl, N,N-dialkylamino, N-alkyl-N-arylamino, chlorine, bromine, morpholino, acetamido and wherein $R^5$ and $R^6$ or $R^7$ and $R^8$ may be joined by or be a —$C_4H_4$—, —$(CH_2)_3$—, or —$C_3H_3N$— moiety; and $R^{23}$ is hydrogen, halogen, a hydrocarbyl-containing group, or a heterocyclic group, preferably $R^{23}$ is a group selected from the group consisting of: hydrogen, a $C_1$-$C_{20}$ alkyl, a $C_3$-$C_{18}$ cycloalkyl, a $C_6$-$C_{18}$ aryl, a $C_2$-$C_{18}$ alkenyl, a $C_6$-$C_{18}$ arylamino, and substituted sulfonyl, more preferably $R^{23}$ is selected from the group consisting of hydrogen and —$SO_2C_6H_5$.

A particularly preferred dye is represented by the formula

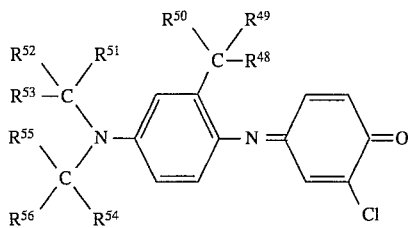

wherein each of $R^{48}$, $R^{49}$, and $R^{50}$, is independently selected from the group consisting of: hydrogen, halogen and an acyclic, alicyclic or aromatic hydrocarbyl group optionally interrupted with one or more heteroatoms.

Each of $R^{51}$, $R^{52}$, $R^{53}$, $R^{54}$, $R^{55}$, and $R^{56}$ is independently selected from the group consisting of hydrogen and an acyclic, alicyclic or aromatic hydrocarbyl group optionally interrupted with one or more heteroatoms. Optionally, any two of $R^{51}$, $R^{52}$, $R^{53}$, $R^{54}$, $R^{55}$, and $R^{56}$ may together to form an alicyclic or aromatic ring.

Preferably, at least four of $R^{48}$, $R^{49}$, $R^{50}$, $R^{51}$, $R^{52}$, $R^{53}$, $R^{54}$, $R^{55}$, and $R^{56}$ are hydrogen, and more preferably at least six are hydrogen.

More preferably, each of $R^{48}$, $R^{49}$, and $R^{50}$ is independently selected from the group consisting of hydrogen, alkyl and halogen; and each of $R^{51}$, $R^{52}$, $R^{53}$, $R^{54}$, $R^{55}$, and $R^{56}$ is independently selected from the group consisting of hydrogen and alkyl that is optionally substituted by one or more cyano, alkoxy, hydroxy, alkylsiloxy, alkylsilyl, acyl, aryl, halo, arylsiloxy, arylsilyl, amino, and mono or dialkyl amino groups.

Most preferably, at least one of $R^{51}$, $R^{52}$, $R^{53}$, $R^{54}$, $R^{55}$, and $R^{56}$ is
—$CH_2$ $OSi(CH_3)_2$ $C(CH_3)_3$
—$CH_2$ $OC(O)CH_2CH(CH_3)CH_2C(CH_3)_3$
—$CH_2$ $OC(O)C(CH_3)_3$
—$CH_2$ $OCH_2$ $OCH_2CH_2Si(CH_3)_3$
—$CH_2Cl$
—$CH_2OC(O)NHCH_2CH_2CH_2CH_3$
—$CH_2OC(O)NHCH_2CH_2CH_2Si(OCH_2CH_3)_3$ Another particularly preferred dye is represented by the formula

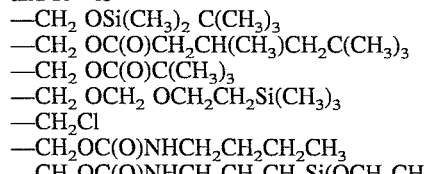

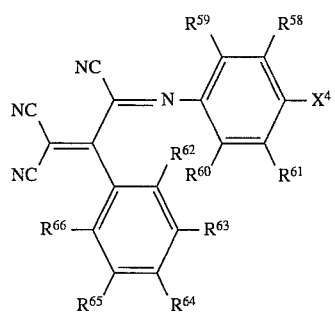

wherein $X^4$ is N—$R^{67}$ $R^{68}$, O—$R^{69}$, S—$R^{70}$ or $CR^{71}$ $R^{72}$ $R^{73}$ wherein each of $R^{58}$, $R^{59}$, $R^{60}$, $R^{61}$, $R^{62}$, $R^{63}$, $R^{64}$, $R^{65}$, $R^{66}$, is independently selected from the group consisting of hydrogen, halogen, a hydrocarbyl group optionally interrupted with one or more heteroatoms and an acyclic, alicyclic or aromatic heterocyclic group, and each of $R^{67}$, $R^{68}$, $R^{69}$, $R^{70}$, $R^{71}$, $R^{72}$, and $R^{73}$ is independently selected from the group consisting of hydrogen, a hydrocarbyl group optionally interrupted with one or more heteroatoms and an acyclic, alicyclic or aromatic heterocyclic group.

Preferably, at least four of $R^{58}$, $R^{59}$, $R^{60}$, $R^{61}$, $R^{62}$, $R^{63}$, $R^{64}$, $R^{65}$, and $R^{66}$ are hydrogen, and more preferably at least six are hydrogen.

More preferably, each of $R^{67}$, $R^{68}$, $R^{69}$, $R^{70}$, $R^{71}$, $R^{72}$, and $R^{73}$ is independently selected from the group consisting of hydrogen and alkyl that is optionally substituted by one or more cyano, alkoxy, hydroxy, alkylsiloxy, alkylsilyl, acyl, aryl, halo, arylsiloxy, arylsilyl, amino, and mono or dialkyl amino groups.

Most preferably, at least one of $R^{67}$, $R^{68}$, $R^{69}$, $R^{70}$, $R^{71}$, $R^{72}$, and $R^{73}$ is
—$CH_2CH_2$ $OSi(CH_3)_2$ $C(CH_3)_3$
—$CH_2CH_2$ $OC(O)CH_2CH(CH_3)CH_2C(CH_3)_3$
—$CH_2CH_2$ $OC(O)C(CH_3)_3$
—$CH_2CH_2$ $OCH_2$ $OCH_2CH_2Si(CH_3)_3$
—$CH_2CH_2Cl$
—$CH_2CH_2OC(O)NHCH_2CH_2CH_2CH_3$
—$CH_2CH_2OC(O)NHCH_2CH_2CH_2Si(OCH_2CH_3)_3$ Particularly preferred compounds of this formula have the structure

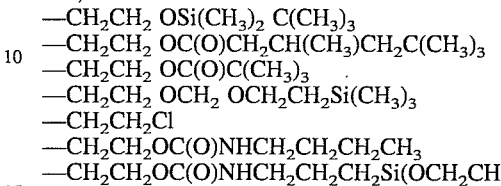

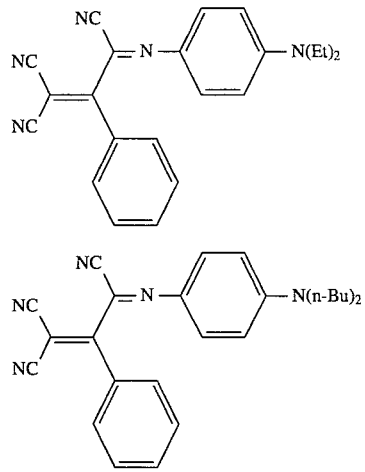

Another particularly preferred dye is represented by the formula

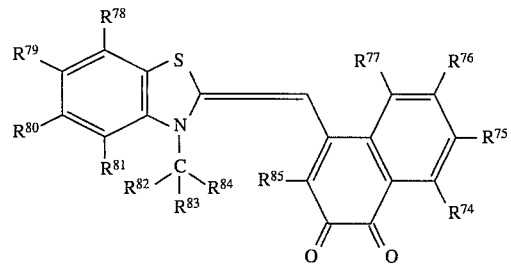

wherein each of $R^{74}$, $R^{75}$, $R^{76}$, $R^{77}$, $R^{78}$, $R^{79}$, $R^{80}$, $R^{81}$, and $R^{85}$ is independently selected from the group consisting of hydrogen, halogen, a hydrocarbyl group optionally interrupted with one or more heteroatoms and an acyclic, alicyclic or aromatic heterocyclic group, and each of $R^{82}$, $R^{83}$, and $R^{84}$ is independently selected from the group consisting of hydrogen, a hydrocarbyl group optionally interrupted with one or more heteroatoms and an acyclic, alicyclic or aromatic heterocyclic group.

Preferably, at least four of $R^{74}$, $R^{75}$, $R^{76}$, $R^{77}$, $R^{78}$, $R^{79}$, $R^{80}$, $R^{81}$, and $R^{85}$ are hydrogen, and more preferably at least six are hydrogen.

More preferably, each of $R^{82}$, $R^{83}$, $R^{84}$ is independently selected from the group consisting of hydrogen and alkyl that is optionally substituted by one or more cyano, alkoxy, hydroxy, alkylsiloxy, alkylsilyl, acyl, aryl, halo, arylsiloxy, arylsilyl, amino, and mono or dialkyl amino.

Most preferably, at least one of $R^{82}$, $R^{83}$, $R^{84}$ is

—$CH_2OSi(CH_3)_2C(CH_3)_3$
—$CH_2OC(O)CH_2CH(CH_3)CH_2C(CH_3)_3$
—$CH_2OC(O)C(CH_3)_3$
—$CH_2OCH_2OCH_2CH_2Si(CH_2)_2C(CH_3)_3$
—$CH_2Cl$
—$CH_2OC(O)NHCH_2CH_2CH_2CH_3$
—$CH_2OC(O)NHCH_2CH_2CH_2Si(OCH_2CH_3)_3$

It will be apparent to those of ordinary skill in the art that further substitution of alkyl groups not involved in the conjugated electronic portion of the molecule are logical points for changing or enhancing physical properties of the molecule, such as crystallinity, solubility, melting point, toxicology or biological activity, etc. Such substitution may be made without losing the essential characteristics of the molecule as a dye, i.e., it will still exhibit color and bleaching propensity that is the same or somewhat modified from the color and bleaching characteristics of the core dye structure.

Another class of particularly suitable dyes may be represented by the following general formula (F18):

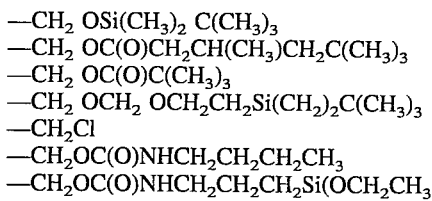

wherein:

each $R^{24}$ and $R^{25}$ group is independently hydrogen, a hydrocarbyl-containing group, or a heterocyclic group with the proviso that at least one of $R^{24}$ and $R^{25}$ is or contains a substituted aryl, aminoaryl or heterocyclic group, preferably each $R^{24}$ and $R^{25}$ group is independently selected from the group consisting of: hydrogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino; more preferably each $R^{24}$ and $R^{25}$ group is a $C_6$-$C_{18}$ aminoaryl group;

each $R^{26}$ and $R^{27}$ group is independently a —$(CF_2)_mF$ group wherein m is a number between 0 and 20, more preferably m is a number between 0 and 10, most preferably m is 0 or 1; and n is an integer preferably less than 5, more preferably n is 1 or 2.

Another class of particularly suitable dyes may be represented by the following general formula (F19):

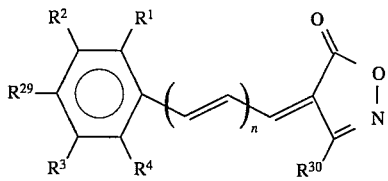

wherein:

each $R^1$, $R^2$, $R^3$, $R^4$, and $R^{29}$ group is independently hydrogen, halogen, a hydrocarbyl-containing group, or a heterocyclic group, preferably each $R^1$, $R^2$, $R^3$, $R^4$ and $R^{29}$ group is independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, carboxamide (—$C(O)NR^1R^2$), and wherein any two adjacent $R^1$, $R^2$, $R^3$, $R^4$ or $R^{29}$ group may be connected to form a ring; more preferably, each $R^1$, $R^2$, $R^3$, $R^4$ and $R^{29}$ group is independently selected from the group consisting of: hydrogen, halogen, a $C_1$-$C_{10}$ alkyl, a $C_1$-$C_{10}$ alkoxy, a $C_5$-$C_8$ cycloalkyl, a $C_6$-$C_{10}$ aryl, a $C_2$-$C_{10}$ alkenyl, and a $C_1$-$C_{10}$ alkylamino, and wherein any two adjacent $R^1$, $R^2$, $R^3$, $R^4$ or $R^{29}$ groups may be connected to form a saturated or unsaturated 5 to 8 member ring; most preferably each $R^1$, $R^2$, $R^4$ and $R^{29}$ group is independently selected from the group consisting of: hydrogen, methyl, ethyl, propyl, butyl, methoxy, ethoxy, propoxy, a $C_5$-$C_8$ cycloalkyl, a $C_6$-$C_{10}$ aryl, a $C_2$-$C_{10}$ alkenyl, a $C_1$-$C_{10}$ alkylamino, chlorine, bromine;

$R^{30}$ is independently hydrogen, halogen, a hydrocarbyl-containing group, or a heterocyclic group, preferably $R^{30}$ is a group independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino; more preferably $R^{30}$ is a group independently selected from the group consisting of: hydrogen, halogen, a $C_1$-$C_{10}$ alkyl, a $C_1$-$C_{10}$ alkoxy, a $C_5$-$C_8$ cycloalkyl, a $C_6$-$C_{10}$ aryl, a $C_2$-$C_{10}$ alkenyl, and a $C_1$-$C_{10}$ alkylamino; and most preferably $R^{30}$ is selected from the group consisting of: hydrogen, methyl, ethyl, propyl, butyl, methoxy, ethoxy, propoxy, a $C_5$-$C_8$ cycloalkyl, and a $C_6$-$C_{10}$ aryl;

n is an integer preferably less than 5, more preferably n is 1 or 2.

Another class of particularly suitable dyes includes anionic oxonol dyes having the following general formula (F20):

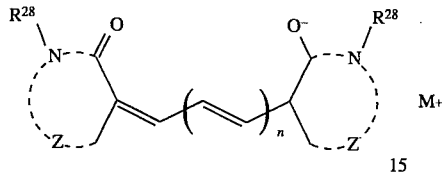

wherein:

Z represents the non-metallic atoms necessary to complete a substituted or unsubstituted nitrogen-containing heterocyclic ring, preferably the non-metallic atoms are selected from the group consisting of O, N, C and S, each $R^{28}$ is independently hydrogen, a hydrocarbyl-containing group, or a heterocyclic group, preferably each $R^{28}$ is independently selected from the group consisting of: hydrogen, a $C_1$-$C_{20}$ alkyl, a $C_3$-$C_{18}$ cycloalkyl, a $C_6$-$C_{18}$ aryl, a $C_6$-$C_{18}$ hydroxyaryl, a $C_6$-$C_{18}$ carboxyaryl, a $C_2$-$C_{18}$ alkenyl, a $C_6$-$C_{18}$ aminoaryl; more preferably each $R^{28}$ is independently selected from the group consisting of: hydrogen, a $C_1$-$C_{10}$ alkyl, a $C_5$-$C_8$ cycloalkyl, a $C_6$-$C_{10}$ aryl, and a $C_2$-$C_{10}$ alkenyl;

n is an integer preferably less than 5, more preferably 1 or 2; and wherein

M+ is selected from any suitable cation including sodium, triethylammonium and the like.

Another class of particularly suitable dyes includes cationic dyes having the following general formula (F30):

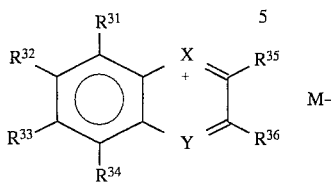

wherein:
each $R^{31}$, $R^{32}$, $R^{33}$, and $R^{34}$ group is independently hydrogen, halogen, a hydrocarbyl-containing group, or a heterocyclic group; preferably each $R^{31}$, $R^{32}$, $R^{33}$, and $R^{34}$ group is independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, carboxamide (—$C(O)NR^1R^2$), and wherein any two adjacent $R^{31}$, $R^{32}$, $R^{33}$, or $R^{34}$ groups may be connected to form a ring; more preferably each $R^{31}$, $R^{32}$, $R^{33}$, and $R^{34}$ group is independently selected from the group consisting of: hydrogen, halogen, a $C_1$-$C_{10}$ alkyl, a $C_1$-$C_{10}$ alkoxy, a $C_5$-$C_8$ cycloalkyl, a $C_6$-$C_{10}$ aryl, a $C_2$-$C_{10}$ alkenyl, and a $C_1$-$C_{10}$ alkylamino, and wherein any two adjacent $R^{31}$, $R^{32}$, $R^{33}$, or $R^{34}$ groups may be connected to form a 5 to 8 member ring; and most preferably each $R^{31}$, $R^{32}$, $R^{33}$, and $R^{34}$ group is independently selected from the group consisting of: hydrogen, methyl, ethyl, propyl, butyl, methoxy, ethoxy, propoxy, a $C_5$-$C_8$ cycloalkyl, a $C_6$-$C_{10}$ aryl, a $C_2$-$C_{10}$ alkenyl, a $C_1$-$C_{10}$ alkylamino, chlorine, bromine, and wherein $R^{33}$ and $R^{34}$ may be joined by a —$C_4H_4$—, —$(CH_2)_3$—, or —$C_3H_3N$— moiety;

$R^{35}$ and $R^{36}$ are as defined above for $R^{33}$ and $R^{34}$;

X is O, S, or $NR^{37}$;

Y is N or $CR^{38}$;

$R^{37}$ and $R^{38}$ are as defined above for $R^{33}$; and wherein

M— is any suitable anion.

Another class of particularly suitable dyes includes cationic dyes having the following general formula (F31):

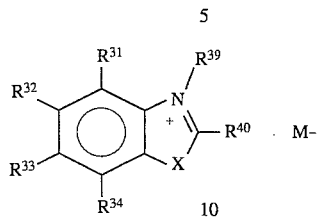

wherein:
each $R^{31}$, $R^{32}$, $R^{33}$, and $R^{34}$ group is independently hydrogen, halogen, a hydrocarbyl-containing group, or a heterocyclic group, preferably each $R^{31}$, $R^{32}$, $R^{33}$, and $R^{34}$ group is independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, carboxamide (—$C(O)NR^1R^2$), and wherein any two adjacent $R^{31}$, $R^{32}$, $R^{33}$, or $R^{34}$ groups may be connected to form a ring; more preferably each $R^{31}$, $R^{32}$, $R^{33}$, and $R^{34}$ group is independently selected from the group consisting of: hydrogen, halogen, a $C_1$-$C_{10}$ alkyl, a $C_1$-$C_{10}$ alkoxy, a $C_5$-$C_8$ cycloalkyl, a $C_6$-$C_{10}$ aryl, a $C_2$-$C_{10}$ alkenyl, and a $C_1$-$C_{10}$ alkylamino, and wherein any two adjacent $R^{31}$, $R^{32}$, $R^{33}$, or $R^{34}$ groups may be connected to form a 5 to 8 member ring; and most preferably each $R^{31}$, $R^{32}$, $R^{33}$, and $R^{34}$ group is independently selected from the group consisting of: hydrogen, methyl, ethyl, propyl, butyl, methoxy, ethoxy, propoxy, a $C_5$-$C_8$ cycloalkyl, a $C_6$-$C_{10}$ aryl, a $C_2$-$C_{10}$ alkenyl, a $C_1$-$C_{10}$ alkylamino, chlorine, bromine, and wherein $R^{33}$ and $R^{34}$ may be joined by a —$C_4H_4$—, —$(CH_2)_3$—, or —$C_3H_3N$— moiety;

$R^{39}$ is independently hydrogen, a hydrocarbyl-containing group or a heterocyclic group, preferably $R^{39}$ is a group selected from the group consisting of: hydrogen, a $C_1$-$C_{20}$ alkyl, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino;

$R^{40}$ is independently hydrogen, halogen, a hydrocarbyl-containing group, or a heterocyclic group, preferably $R^{40}$ is a group selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, and carboxamide;

X is C=$R^{48}$, $C(R^{38})_2$, O, S, or $NR^{37}$, more preferably X is C=$R^{48}$, $C(R^{38})_2$ or S, wherein $R^{37}$ is as defined above for $R^{39}$, $R^{38}$ is as defined above for $R^{40}$, $R^{48}$ is all oxo group, a divalent hydrocarbyl-containing group, or a divalent heterocyclic group, wherein $R^{48}$ and $R^{34}$ may be connected to form an unsaturated ring, for example, $R^{48}$ and $R^{34}$ may be joined by a —$C_3H_3$— moiety, and wherein $R^{37}$ and $R^{34}$ may be connected to form a saturated or unsaturated ring; and wherein M— is any suitable anion.

Another class of particularly suitable dyes includes cationic dyes having the following general formula (F32):

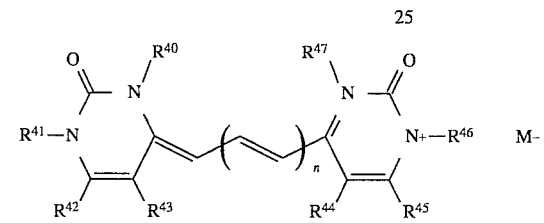

wherein:
each $R^{42}$ to $R^{45}$ group is independently hydrogen, halogen, a hydrocarbyl-containing group, or a heterocyclic group, preferably each $R^{42}$ to $R^{45}$ group is independently selected from the group consisting of: hydrogen, halogen, a $C_1$-$C_{20}$ alkyl, a $C_1$-$C_{20}$ alkoxy, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, each $R^{40}$, $R^{41}$, $R^{46}$ and $R^{47}$ group is independently hydrogen, halogen, a hydrocarbyl-containing group, or a heterocyclic group, preferably each $R^{40}$, $R^{41}$, $R^{46}$ and $R^{47}$ group is independently selected from the group consisting of: hydrogen, a $C_1$-$C_{20}$ alkyl, a $C_3$-$C_{18}$ cycloalkyl, a $C_6$-$C_{18}$ aryl, a $C_6$-$C_{18}$ aryloxy, a $C_6$-$C_{18}$ hydroxyaryl, a $C_6$-$C_{18}$ arylcarboxy, a $C_6$-$C_{18}$ carboxyaryl, a $C_2$-$C_{18}$ alkenyl, a $C_1$-$C_{20}$ alkylamino, a $C_6$-$C_{18}$ arylamino, a $C_6$-$C_{18}$ aminoaryl, a $C_2$-$C_{20}$ di(hydrocarbyl)amino, wherein any two adjacent $R^{41}$ to $R^{43}$ groups may be connected to form a ring and wherein $R^{44}$ and $R^{45}$ may be connected to form a ring; more preferably $R^{40}$, $R^{41}$, $R^{46}$ and $R^{47}$ are methyl and $R^{42}$ to $R^{45}$ are hydrogen;

n is an integer preferably less than 5, more preferably 1, 2 or 3; and wherein

M– is any suitable anion.

Suitable cure-indicator dyes for use in the present invention include neutral dyes such as: 4-[[4-(Dimethylamino)phenyl]imino]-2,5-cyclohexadien-1-one; 2-Chloro-4-[[2-methyl-4-(diethylamino)phenyl]imino]-2,5-cyclohexadien-1-one; 4-[[4-(Diethylamino)phenyl]imino]-1,4-dihydronaphthalen-1-one; 4-[[4(Dimethylamino)phenyl]imino]-1,4-dihydronaphthalen-1-one; 4-[[2-methyl-4-(diethylamino)phenyl]imino]-1,4-dihydronaphthalen-1-one; 3-Methoxy-4-[[2-methyl-4-(diethylamino)phenyl]imino]-2,5-cyclohexadien-1-one; 3-Chloro-4-[[2-methyl-4-(diethylamino)phenyl]imino]-2,5-cyclohexadien-1-one; 2-Methyl-4-[[4-(4-morpholinyl)phenyl]-imino]-2,5-cyclohexadien-1-one; 2,6-Dichloro-4-[[4-(4-morpholinyl)-phenyl]imino]-2,5-cyclohexadien-1-one; 2,6-Dimethyl-4-[[4-(4-morpholinyl)-phenyl]imino]-2,5-cyclohexadien-1-one; 2,5-Dichloro-4-[[4-(diethylamino)-phenyl]imino]-2,5-cyclohexadien-1-one; 3-Methoxy-4-[[3-methoxy-4-(diethylamino)phenyl]imino]-2,5-cyclohexadien-1-one; 2,6-Dichloro-4-[[2-methyl-4-(diethylamino)phenyl]imino]-2,5-cyclohexadien-1-one; 3-[[4-(Diethylamino)-2-methylphenyl]imino]-6-oxo-N-phenyl-1,4-cyclohexadiene-1-carboxamide; 5-[[4-(Diethylamino)-2-methylphenyl]imino]-8-(5H)-quinolinone; 2,5-Dichloro-4-[[2-methyl-4-(diethylamino)-phenyl]imino]-2,5-cyclohexadien-1-one; 2,6-Dichloro-4-[[4-(acetamido)phenyl]imino]-2,5-cyclohexadien-1-one; 2,6-Dichloro-4-[4-ethoxy phenyl)imino]-2,5-cyclohexadien-1-one; 2,6-Dichloro-4-[(2-methyl-4-ethoxy phenyl)imino]-2,5-cyclohexadien-1-one; 2,6-Dimethyl-4-[4-hydroxy phenyl)imino]-2,5-cyclohexadien-1-one; 2,6-Dichloro-4-[(4-methoxy-1-naphthyl)imino]-2,5-cyclohexadien-1-one; 2,6-Dichloro-4-[[4-(benzyloxy)phenyl]imino]-2,5-cyclohexadien-1-one; 2,6-Dichloro-4-[(2,4-dimethoxyphenyl)imino]-2,5-cyclohexadien-1-one; 2,6-Dichloro-4-[(4-methoxyphenyl)imino]-2,5-cyclohexadien-1-one; 4-(phenylimino)-2,5-cyclohexadien-1-one; 4-(1-naphthylimino)-2,5-cyclohexadien-1-one; 4-(2-naphthylimino)-2,5-cyclohexadien-1-one; 2,5-Bis(phenylamino)-4-(phenylimino)-2,5-cyclohexadien-1-one; 2,5-Dibromo-4-[(2,4-dibromophenyl)imino]-2,5-cyclohexadien-1-one; 2,3,5-Trichloro-4-[(2,4,6-trichlorophenyl)imino]-2,5-cyclohexadien-1-one; 2,6-Dichloro-4-[4-[4-(dimethylamino)phenyl]-5-phenyl-(2H)-imidazol-2-ylidine]-2,5-cyclohexadien-1-one; 2,6-Dichloro-4-[4,5-bis(4-hydroxyphenyl)-(2H)-imidazol-2-ylidine]-2,5-cyclohexadien-1-one; 2,6-Dimethoxy-4-[4,5-bis(2-furyl)-(2H)-imidazol-2-ylidine]-2,5-cyclohexadien-1-one; 2,6-Bis[1,1-(dimethyl)ethyl]-4-[4,5-bis(2-furyl)-(2H)-imidazol-2-ylidene]-2,5-cyclohexadien-1-one; 4-(phenylimino)-2,5-cyclohexadien-1-imine; Mono[(3-methyl-2-(3H)-benzothiazolylidene)hydrazono]2,5-cyclohexadiene-1,4-dione; 4-[(3-Chloro-4-oxo-2,5-cyclohexadien-1-ylidine)amino]-1,2-dihydro-1,5-dimethyl-2-phenyl-(3H)-pyrazol-3-one; 4-[(3,5-Dichloro-4-oxo-2,5-cyclohexadien-1-ylidine)amino]-1,2-dihydro-1,5-dimethyl-2-phenyl-(3H)-pyrazol-3-one; 3-[(3,5-Dichloro-4-oxo-2,5-cyclohexadien-1-ylidine)amino]-2,5-dihydro-4,5-dimethyl-1-phenylpyrrol-2-one; 4-(Phenylsulfonyl)imino-1-[4-[(phenylsulfonyl)imino]-2,5-cyclohexadien-1-ylidenyl]-2,5-cyclohexadiene; 4-[6,6-Bis[(trifluoromethyl)sulfonyl]-1,3,5-hexatrienyl]-N,N-dimethylbenzenamine; 4-[4,4-Bis[(trifluoromethyl)sulfonyl]-1,3-butadienyl]-2-ethoxy-N,N-dimethylbenzenamine; 4-[4,4-Bis[(trifluoromethyl)sulfonyl]-1,3-butadienyl]-2,5-dimethoxy-N,N-dimethylbenzenamine; 9-[4,4-Bis[(trifluoromethyl)sulfonyl]-1,3-butadienyl]-2,3,6,7-tetrahydro-(1H,5H)-benzo[ij]quinolizine; 4-[4,4-Bis[(trifluoromethyl)sulfonyl]-1,3-butadienyl]-2,6-N,N-tetramethyl-benzenamine; 4-[5,5-Bis[(trifluoromethyl)sulfonyl]-2,4-pentadienylidene]-1,4-dihydro-1-methylquinoline; 6,6-Bis[4-(dimethylamino)phenyl]1,3,5-hexatriene-1,1-bis(sulfonylfluoride); 4-[4,4-Bis[(trifluoromethyl)sulfonyl]-1,3-butadienyl]-N,N-dimethylbenzenamine; and 4-[3-[4-(Dimethylamino)phenyl]-2-propenylidene]-2-phenyl-5(4H)-oxazolone; anionic dyes having the following anions: 5-[5-(1,3-Diethylhexahydro-2,4,6-trioxo-5-pyrimidinyl)-2,4-pentadienylidene]-1,3-diethyl-2,4,6(1H,3H,5H)-pyrimidenetrione; and cationic dyes having the following cations or having the cations of the following cationic dyes: 3H-Indolium, 3-[3-[4-(dimethylamino)phenyl]-2-propenylidene]-1-methyl-2-phenyl; Benzothiazolium, 3-(3-amino-3-oxopropyl)-2-[[4-[bis(2-chloroethyl)amino]phenyl]azo]-6-methoxy-; Benzothiazolium, 3-(3-amino-3-oxopropyl)-2-[[4-(diethylamino)phenyl]azo]-6-ethoxy-; Benzothiazolium, 3-(3-amino-3-oxopropyl)-2-[[4-(diethylamino)-2-methylphenyl]azo]-6-ethoxy-; CAS 12221-40-8; CAS 12270-14-3; CAS 12221-31-7; CAS 12221-34-0; Benzo[a]phenoxazin-7-ium, 9-(dimethylamino)-; 2-[4,4,-bis[4-dimethylamino)phenyl]-1,3-butadienyl]-1-ethyl quinolinium; 4-[4,4,-bis[4-(dimethylamino)phenyl]-1,3-butadienyl]1-ethyl quinolinium; Naphtho[2,1-d]thiazolium, 2-[4,4-bis[4-(dimethylamino)phenyl]-1,3-butadienyl]-3-ethyl-; 2-[2-[4-(dimethylamino)phenyl]ethenyl]-1-phenyl-3-methyl quinoxalinium; Quinolinium, 2-[3-(5-chloro-1,3-dihydro-1,3,3-trimethyl-(2H)-indol-2-ylidene)-1-propenyl]-1-methyl-; Benzothiazolium, 2-[[4-(dimethylamino)phenyl]azo]-6-methoxy-3-methyl-; Benz[cd]indolium, 2-[4-(diethylamino)-2-ethoxyphenyl]-1-ethyl-; 2-[p-(Dimethylamino)styryl]-1,3-dimethylquinoxalinium; 2-[3-(5-chloro-1,3-dihydro-1,3,3-trimethyl-(2H)-indol-2-ylidene)-1-propenyl]-1-methylquinoxalinium; C. I. Basic Blue 40; Benzothiazolium, 2-[[4-[ethyl(2-hydroxyethyl)amino]phenyl]azo]-6-methoxy-3-methyl-; Benzothiazolium, 2-[[4-[ethyl(2-hydroxyethyl)amino]phenyl]azo]-6-methoxy-3-methyl-; C I. Basic Blue 42; C. I. Basic Blue 53; 3H-Indolium, 5-chloro-2-[5-(5-chloro-1,3-dihydro-1,3,3-trimethyl-2H-indol-2-ylidene)-1,3-pentadienyl]-1,3,3-trimethyl-; Basic Blue 142; Benz[cd]indolium, 2-[2-(9-ethyl-(9H)-carbazol-3-yl)ethenyl]-1-methyl-; Benz[cd]indolium, 2-[2-[4-(dimethylamino)phenyl]-2-phenylethenyl]-1-methyl-; Benz[cd]indolium, 2-[2,2-bis[4-(dimethylamino)phenyl]ethenyl]-1-methyl-; Benz[cd]indolium, 2-[2-(2,3-dihydro-1-methyl-2-phenyl-1H-indol-3-yl)-2-(2-methylphenyl)ethenyl]-1-methyl-; Pyrimidinium, 4-[5-(2,3-dihydro-1,3-dimethyl-2-oxo-4(1H)-pyrimidinylidene)-1,3-pentadienyl]-2,3-dihydro-1,3-dimethyl-2-oxo-; 3H-Indolium, 2-[[3-[(1,3-dihydro-1,3,3-trimethyl-2H-indol-2-ylidene)methyl]-5,5-dimethyl-2-cyclohexen-1-ylidene]

methyl]-1,3,3-trimethyl-; Benz[cd]indolium, 2-[2-[4-(diethylamino)-2-methylphenyl]ethenyl]-1-methyl-; 3H-Indolium, 3-[3-[4-[(dimethylamino)phenyl]-2-propenylidene]-1-methyl-2-(4-methoxyphenyl)-; 3H-Indolium, 3-[(2,5-dimethyl-1-phenyl-(1H)-pyrrol-3-yl)methylene]-1, 2-dimethyl-; 3H-Indolium, 3-[2,5-dimethyl-1-phenyl-(1H)-pyrrol-3-yl)methylene]-1-methyl-2-phenyl-; 2-[2-[2-chloro-4-(dimethylamino)phenyl]ethenyl]-1-methylbenz[cd] indolium; C. I. Basic Violet 22; C. I. Basic Red 15; Benz [cd]indolium, 2-[2-[4-(dimethylamino)phenyl]ethenyl]-1-methyl-; Benz[cd]indolium,2-[2-[4-(dimethylamino)-2-ethoxyphenyl]ethenyl]-1-methyl-; and 3H-Indolium, 2-[1-cyano-4,4-bis[4-(dimethylamino)phenyl]-1,3-butadienyl]-1, 3,3-trimethyl-.

Presently particularly preferred dyes for use in the present invention include: 4-[[4-(Dimethylamino)phenyl]imino]-2, 5-cyclohexadien-1-one; 2-Chloro-4-[[2-methyl-4-(diethylamino)phenyl]imino]-2,5-cyclohexadien-1-one; 4-[[4-(Diethylamino)phenyl]imino]-1,4-dihydronaphthalen-1-one; 4-[[4-(Dimethylamino)phenyl]imino]-1,4-dihydronaphthalen-1-one; 4-[[2-methyl-4-(diethylamino)phenyl]imino]-1, 4-dihydronaphthalen-1-one; 3-Methoxy-4-[[2-methyl-4-(diethylamino)phenyl]imino]-2,5-cyclohexadien-1-one; 2-Methyl-4-[[4-(4-morpholinyl)phenyl]imino]-2,5-cyclohexadien-1-one; 2,5-Dichloro-4-[[4-(diethylamino)phenyl] imino]-2,5-cyclohexadien-1-one; 3-[[4-(Diethylamino)-2-methylphenyl]imino]-6-oxo-N-phenyl-1,4-cyclohexadiene-1-carboxamide; 5-[[4-(Diethylamino)-2-methylphenyl] imino]-8-(5H)-quinolinone; 2,6-Dichloro-4-[[4-(acetamido)phenyl]imino]-2,5-cyclohexadien-1-one; 4-(1-naphthylimino)-2,5-cyclohexadien-1-one; 4-(2-naphthylimino)-2,5-cyclohexadien-1-one; 2,5 -Bis(phenylamino)-4(phenylimino)-2,5-cyclohexadien-1-one; 4-[5,5-Bis[(trifluoromethyl)sulfonyl]-2,4-pentadienylidene]-1,4-dihydro-1-methylquinoline; 6,6-Bis[4-(dimethylamino)phenyl]1,3,5-hexatriene-1,1-bis(sulfonylfluoride); 4-[4,4-Bis[(trifluoromethyl)sulfonyl]-1,3-butadienyl]-N,N-dimethylbenzenamine; and 4-[3-[4-(Dimethylamino)phenyl]-2-propenylidene]-2-phenyl-5(4H)-oxazolone.

A variety of adjuvants may be utilized to modify the relationship between the color change and the extent of cure. These adjuvants are generally added to the primary compositions of this invention in an amount suitable to obtain the desired interactions. Several suitable classes of indicator adjuvants include active proton sources such as alcohols, acids, and water. Alternatively, a variety of hydrosilation inhibitors well known in the art may also serve as adjuvants such as acetylenic alcohols, certain polyolefinic siloxanes, pyridine, acrylonitrile, organic phosphines and phosphites, unsaturated amides, alkyl fumarates, alkyl maleates and the like.

As previously mentioned the composition containing the cure-indicating dye optionally may comprise one or more suitable solubilizing agents (e.g., surfactants). The surfactants may be employed to facilitate or maintain the dissolution or dispersion of the cure-indicating dye and/or other ingredients in the composition, to facilitate uniform mixing of the reactants, or to adjust the composition's viscosity or flow. The surfactant may also be employed to modify the surface wetting characteristics of the composition. In particular, the surfactant may be desired when the composition comprises a filler. Suitable surfactants for use with silicone compositions include surfactants selected from the group consisting of ethoxylated nonionic surface active agents and cationic or amphoteric fluorochemical surface active agents such as those disclosed in U.S. Pat. No. 4,657,959 (Bryan et al.) which is herein incorporated by reference. Preferred surfactants contain one or more solubilizing groups (e.g., one or more siloxane groups, hydrocarbyl-containing groups or perfluoroalkyl groups) which render the surfactant soluble or dispersible in the silicone composition.

A preferred class of ethoxylated surfactants containing a siloxane solubilizing group has the average formula

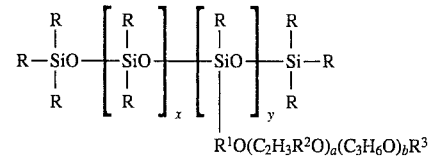

where each R is independently a monovalent hydrocarbyl radical, $R^1$ is a divalent hydrocarbylene radical, each $R^2$ is independently hydrogen or a lower hydroxyalkyl radical, $R^3$ is hydrogen or a monovalent hydrocarbyl radical; x, a, and b are independently greater than or equal to zero; and y is independently greater than or equal to one. Preferably in compounds of Formula I, R is methyl, $R^1$ is methylene (—$CH_2$—), ethylene (—$CH_2CH_2$—), propylene (—$CH_2CH_2CH_2$—) or butylene (—$CH_2CH_2CH_2CH_2$—), $R^2$ is hydrogen, $R^3$ is hydrogen, methyl, ethyl, propyl, or butyl, x is a number from zero to 100, y is a number from one to five, a is a number from 5 to 300, and b is a number from zero to 300; more preferably R is methyl, $R^1$ is ethylene or propylene, $R^2$ is hydrogen, $R^3$ is hydrogen, methyl, or butyl, x is a number from zero to 80, y is a number from one to five, a is a number from 5 to 200, and b is a number from zero to 200; most preferably R is methyl, $R^1$ is propylene, $R^2$ is hydrogen, $R^3$ is hydrogen, methyl, or butyl, x is a number from zero to 60, y is a number from one to five, a is a number such that the product of y times a is zero to 200, and b is a number such that the product of y times b is zero to 200, and the sum of the product of a times y and b times y is five to 200.

Another preferred class of ethoxylated surfactants has the average formula

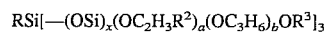

$$RSi[-(OSi)_x(OC_2H_3R^2)_a(OC_3H_6)_bOR^3]_3 \quad \text{II}$$

where R, $R^2$, $R^3$, x, a and b are as defined above for formula I. Preferably in compounds of Formula II, R and $R^3$ are —$CH_3$, $R^2$ is hydrogen, a is five to 20 and b is zero.

Ethoxylated surfactants of Formulas I and II above are described in Union Carbide Corp. product literature ("Silwet Surfactants," dated August, 1992; "Organomodified Oils [OMO]," dated April, 1982; "UCAR-SIL EPS Silicone Hydrophilic Finish," dated March 1984 and available from OSi Specialties, Inc., Danbury, Conn.) and in U.S. Pat. Nos. 3,505,377, 3,980,688, and 4,431,789, the disclosures of which are incorporated herein by reference. Several of such ethoxylated surfactants are available from OSi Specialties, Inc. as "SILWET" surface active copolymers. Preferred SILWET surface active copolymers include SILWET L-77, L-7607, L-7630, L-7002 and L-7200.

An additional preferred class of ethoxylated surfactants has the average formula

where $R^2$ and $R^3$ are as defined above for Formula I, each $R^4$ group is independently a monovalent hydrocarbyl radical with the proviso that at least a majority of the $R^4$ groups are sterically hindered alkyl radicals having at least three carbon atoms, c is at least four, d is greater than or equal to zero, and T is hydrogen, a monovalent alkyl or alkenyl radical, or a group of the formula $Si(R^3)_2[OSi(OR^4)_3]_2$. Preferably in compounds of Formula III, $R^2$ is hydrogen, $R^3$ and T are —$CH_3$, $R^4$ is sec-butyl, c is five or more and d is zero. Representative ethoxylated surfactants of Formula III are described in Olin Corp. product literature ("Silicate ClusterÔ Fluids") and in U.S. Pat. Nos. 4,160,776, 4,226,794, and 4,337,168, the disclosures of which are incorporated herein by reference. At least one such surfactant is experimentally available from Olin Corp. as a "SILFAC" polyethoxylated silicate cluster compound bearing the experimental designation "SILFAC 12M".

An additional preferred class of ethoxylated surfactants has the average formula $$(R^4O)_3Si(OC_2H_3R^2)_e(OC_3H_6)_fOT^1 \quad \text{IV}$$

where $R^2$ and $R^4$ are as defined above for Formula III, e is at least four, f is greater than or equal to zero, and $T^1$ is hydrogen, a monovalent alkyl or alkenyl radical, or a group of the formula —$Si(OR^4)_3$. The preparation of these ethoxylated surfactants is described in U.S. Pat. No. 4,657,959. Preferably in compounds of Formula IV, $R^2$ is hydrogen, $R^4$ is sec-butyl, e is ten to 20, f is zero and $T^1$ is —Si(sec-butoxy)$_3$.

Suitable ethoxylated surfactants containing hydrocarbyl solubilizing groups are shown in "Surfactants and Detersive Systems", *Kirk-Othmer Encyclopedia of Chemical Technology*, 3rd Ed., 22, 360–377 (1983), the disclosure of which is incorporated herein by reference. A preferred class of such ethoxylated surfactants has the average formula $$R^5[(OC_2H_3R^2)_g(OC_3H_6)_lOR^3]_{1 \text{ to } 3} \quad \text{V}$$

where $R^2$ and $R^3$ are as defined above for Formula I, $R^5$ is a saturated or unsaturated alkyl or alkylphenyl radical having at least seven carbon atoms, g is a number from zero to 100, 1 is a number from zero to 100, and the sum of g and 1 is at least three.

Suitable ethoxylated surfactants containing perfluoroalkyl solubilizing groups are described in U.S. Pat. No. 2,915,544, the disclosure of which is incorporated herein by reference. A preferred class of such ethoxylated surfactants has the average formula $$Rf—[Q(C_2H_3R^2O)_h(C_3H_6O)_iR^3]_{1 \text{ or } 2} \quad \text{VI}$$

where $R^2$ and $R^3$ are as defined above for Formula I, Rf is a fluorinated, monovalent or divalent, aliphatic, preferably saturated organic radical containing at least four carbon atoms and preferably a terminal perfluoromethyl group, Q is a polyvalent (e.g., divalent) hydrocarbylene linking group (e.g., —$C_2H_4$—, or —$SO_2NR$— where R is as defined above), h is greater than or equal to one, and i is greater than or equal to zero.

The surfactant used in the present invention can also be a cationic or amphoteric fluorosurfactant. Such fluorosurfactants contain at least one perfluoroalkyl solubilizing group Rf where Rf is as defined above for Formula VI. The cationic fluorosurfactants contain at least one cationogenic group which is the radical of a base having an ionization constant in water at 25° C. of at least about $10^{-6}$. The amphoteric fluorosurfactants contain at least one such cationogenic group and at least one anionogenic group which is the radical of an acid having an ionization constant in water at 25° C. of at least about $10^{-6}$. Suitable fluorosurfactants are described, for example, in U.S. Pat. No. 4,484,990, the disclosure of which is incorporated herein by reference.

Other suitable solubilizing or wetting agents include substances such as poly(ethylene oxide), poly(propylene oxide), and copolymers of ethylene oxide and propylene oxide. Suitable such substances have the average formula $$R^1O(C_2H_3R^2O)_j(C_3H_6O)_kR^3 \quad \text{VII}$$

where $R^2$ is as defined above for Formula I, each $R^1$ and $R^3$ group is independently hydrogen, a hydrocarbyl-containing group, or a heterocyclic group, preferably $R^2$ is hydrogen and each $R^1$ and $R^3$ is selected from the group consisting of hydrogen, a $C_1$-$C_{20}$ alkyl, and a $C_1$-$C_{20}$ alkylphenyl group, more preferably each $R^1$ and $R^2$ is hydrogen;

j is a number having an average value between 0 and 25, more preferably j is a number having an average value between 5 and 15;

k is a number having an average value between 0 and 100, more preferably k is a number having an average value of 0; and wherein the sum of j and k is at least 3.

Preferred wetting agents of this class include hydroxy terminated poly(ethylene oxide), hydroxy terminated poly(propylene oxide), and hydroxy terminated copolymers of ethylene oxide and propylene oxide (also known as polyethylene glycols, polypropylene glycols, and copolymers thereof).

The following examples are offered to aid in the understanding of the present invention and are not to be construed as limiting the scope thereof. Unless otherwise indicated, all parts and percentages are by weight

EXAMPLES

Preparatory Example 1a

Preparation of a Karstedt Catalyst

A three neck flask was fired with a mechanical stirrer, reflux condenser, thermometer, and nitrogen purge and placed in a water bath. The flask was charged with 3,000 parts ethanol and 1,200 parts 1,1,3,3-tetramethyl-1,3-divinyldisiloxane and then purged with nitrogen for 5 minutes. Six hundred parts hexachloroplatinic acid was added to the solution and the mixture stirred until the acid was substantially dissolved. Eighteen hundred parts sodium bicarbonate was then added over a 5 minute period. The water bath was heated to 60° C. and then stirred for 2.5 hours. After it had cooled, the solution was filtered, washed with 150 parts ethanol and transferred to a flask containing 6,000 parts dimethylvinylsiloxy terminated polydimethylsiloxane with a viscosity of 0.3 Pa s and a molecular weight of about 10,000 g/mol. The flask was placed on a rotary evaporator and stripped at 45° C. until the vacuum reaches 0.5–1.0 Torr to produce a Karstedt type catalyst solution with a platinum concentration of approximately 2.3–3.0%.

Preparatory Example 1b

Preparation of a Catalyst Complex of Pt° and Divinyltetramethyldisiloxane

Preparation of: Bis(1,5-cyclooctadiene)platinum(0):

To a suspension of lithium ribbon (0.7 g, 100 mmol) in diethyl ether (80 ml) at 0° C. under argon was added freshly distilled 1,3,5,7-cyclooctatetraene, ("COT"), (2.5 g, 24 mmol), and the resultant mixture was allowed to come slowly to room temperature and was stirred overnight. A 2.0 ml aliquot of the dark orange solution was hydrolyzed in approximately 2 ml of water, approximately 1 mg of phenolphthalein was added, and titration with 1.00N HCl required 1.05 ml to reach the endpoint, indicating a 0.25M solution of (COT)Li$_2$. A substantial amount of white solids settled from the solution.

A 250-ml three-necked round-bottomed flask equipped with a magnetic stir bar and fitted with a 60-ml addition funnel was flushed with argon and charged with 3.7 g, 10 mmol finely ground (COD)PtCl$_2$ (as described by McDermott, White, and Whitesides, in *J. Am. Chem. Soc.* 1976, 98, 6521) and 1,5-cyclooctadiene, ("COD"), (15 ml). The mixture was cooled to minus 40° C., and the addition funnel was charged with the 0.25M solution of (COT)Li$_2$ in diethyl ether, prepared above, (41 ml, 10 mmol), which was added dropwise to the rapidly stirred slurry over a period of 45 min. After the addition was complete, the orange mixture was allowed to warm to 0° C. over the course of 1 hour. Volatile materials were separated at reduced pressure until the residue was quite dry. Argon was readmitted to the flask, and the orange residue was extracted at room temperature with five 50 ml portions of toluene. The combined extracts were filtered through a short column of alumina (8×2.5 cm, neutral Brockman activity II). The column was washed with an additional 50-ml portion of toluene, and the volume of the filtrate and washings was reduced by approximately one-half under reduced pressure. The reddish-brown solution was cooled to minus 20° C. and allowed to stand for approximately 60 hours during which time white crystals formed. The mother liquor was separated, and the crystals were washed with four 5 ml portions of diethyl ether and dried under vacuum to yield a first crop of 1.09 g product. The mother liquor was concentrated to dryness under reduced pressure, and the brown residue was washed with five 5 ml portions of diethyl ether and dried under vacuum to give a second crop of 0.58 g. The $^1$H NMR spectra of the first and second crop were identical, consistent for the desired complex and in agreement with published data by Spencer (Spencer, J. L. *Inorg. Synth.* 1979, 19, 213).

Preparation of: Tris(1,3-divinyl-1,1,3,3-tetramethyldisiloxane)diplatinum(0):

Bis(1,5-cyclooctadiene)platinum(0) (600 mg, 1.46 mmol) was added in small portions to a rapidly stirred solution of 1,3-divinyl-1,1,3,3-tetramethyldisiloxane (405 mg, 2.17 mmol) in diethyl ether (15 ml) at room temperature under argon. The mixture was stirred overnight, and concentration under reduced pressure afforded a colorless oil. The crude product was purified by first eluting from Florisil with diethyl ether followed, after concentration, by flash chromatography on silica gel with 98:2 hexanes-diethyl ether. The product was obtained as a colorless oil, homogeneous by TLC, which crystallized on standing. $^1$H, $^{13}$C, $^{29}$Si, and $^{195}$Pt NMR analyses were consistent for the desired complex and in agreement with published data by Hitchcock et al. (Hitchcock, P. B.; Lappert, M. F.; Warhurst, N. J. W. *Angew. Chem., Int. Ed. Engl.* 1991, 30, 438).

The above complex (with the theoretical structure of F25) was dissolved in toluene to provide a catalyst solution having between about 2 and 3 weight percent platinum.

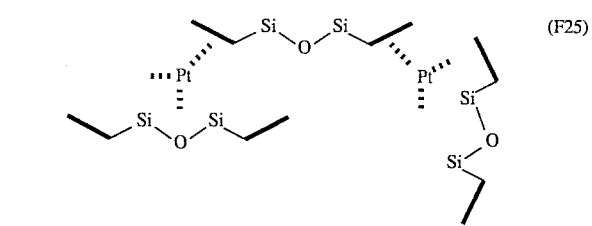 (F25)

Preparatory Example 2

Stock "catalyst" compositions and stock "base" compositions were prepared by combining the following ingredients as listed in Table P2:

TABLE P2

| | | Stock Composition | | | |
|---|---|---|---|---|---|
| Ingredient | Structure | B1 | C1 | B2 | C2 |
| Vinyl terminated polydimethylsiloxane[1] | F21 | 78.35 | 97.95 | 78.35 | 97.95 |
| Crosslinker[2] | F22 | 21.97 | — | 21.97 | — |
| Inhibitor[3] | F23 | 0.06 | — | 0.06 | — |
| Catalyst[4] | F24 | — | 2.05 | — | 2.05 |
| Dichloromethane | | — | — | 100.3 | 100.0 |

[1]"Vinyl terminated polydimiethylsiloxane" = (vinyldimethylsiloxy)-terminated polydimethylsiloxane with a viscosity of approximately 2 Pa s ("LMWP") and available as Y-7942 from OSi Specialties, Inc., Danbury, CT.

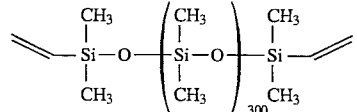

[2]"Crosslinker" = organohydropolysiloxane having a viscosity of approximately 24 to 38 mPa s and approximately 0.2% hydride ("XL1") and available from OSi Specialties, Inc., Danbury, CT.

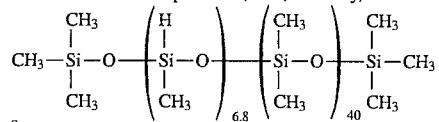

[3]"Inhibitor" = 1,3-divinyltetramethyldisiloxane ("DVTMDS") and available from United Chemical Technology, Inc., Bristol, PA.

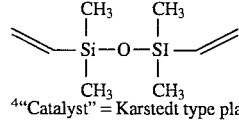

[4]"Catalyst" = Karstedt type platinum catalyst comprising 2.55 wt % platinum catalyst in vinyl terminated polydimethylsiloxane (as described in Preparatory Example 1a and as shown with the approximate formula of structure F24).

(F24) 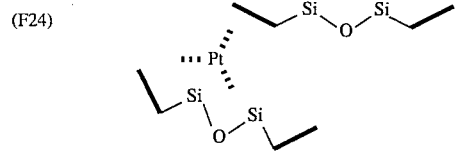

Preparatory Example 3

Preparation of Various Dyes

Preparation of: 2-Chloro-4-[[2-methyl-4-(diethylamino)phenyl]imino]-2,5-cyclohexadien-1-one:

1450 parts K$_3$Fe(CN)$_6$, 595 parts Na$_2$CO$_3$, and 4150 parts water were added to a 12-liter round bottom flask equipped with a mechanical stirrer, thermometer, and addition funnel. The mixture was heated to 55° C. with stirring. A solution of 227 parts 4-(N,N-diethylamino)-2-methylaniline monohydrochloride, 128 parts o-chlorophenol, 1960 parts ethanol, and 2500 parts water was charged to the addition funnel and added dropwise to the stirred, heated solution. After the addition was complete the reaction mixture was maintained at 55° C. with stirring for 20 minutes. The warm mixture was filtered with vacuum and the resulting filter cake was placed in a solution of 296 parts ethanol and 1125 parts water to form a slurry. The dye was isolated by vacuum filtration. This process was repeated two times, first with 296 parts ethanol and 1125 parts water, then with 608 parts methanol. After the final vacuum filtration the filter cake was dried at 40° C. under vacuum for 48 hours. Yield was ~90%. The final product can be recrystallized from ethyl acetate or ethanol.

The preparation of other indoaniline dyes is described by Masafumi Adachi et al. in the *Journal of Organic Chemistry* (*J. Org. Chem.* 1993, 58, 5238–5244) which is herein incorporated by reference. This paper describes a procedure of preparing dyes by oxidative condensation of suitable p-phenylenediamines and phenols using ammonium persulfate as the oxidant (following the procedure outlined in by Vittum et al. in the *J. Am. Chem. Soc.* 1946, 68, 2235).

The preparation of various sulfone dyes is described in U.S. Pat. Nos. 3,933,914, 4,018,810, and 4,357,405; U.S. patent application Ser. No. 07/730,225 now U.S. Pat. No. 5,360,582, and in *Zhurnal Organicheskoi Khimii*, Vol. 15, No. 11, pages 2416 and 2417 (November 1979), which are herein incorporated by reference.

Example 1

A variety of dyes were evaluated as cure indicators by the following procedure. Approximately 0.0005 grams (500 μg) of a dye, as listed in Table 1a, was transferred to a 1.5 dram (6 ml) clear glass vial containing two drops (~200 mg) of dichloromethane. Approximately 1 ml of stock composition B2 was transferred to the vial and the solution mixed with a spatula until homogeneous. Approximately 1 ml of stock composition C2 was transferred to the colored solution, a timer started and the composition was mixed thoroughly for 30 seconds. The composition was placed against a white background and visually examined for the time at which "gelation" and visual color change occurred. Gel times ("GT") were recorded and it was determined if a color change occurred before the gel point, within two times the gel point and/or following 24 hrs at room temperature. Set out in Table 1b are the results observed for these dyes.

TABLE 1a

| Dye # | Identification[1,4] | Further Identification and/or Comments |
|---|---|---|
| 1 | 4-[[4-(Dimethylamino)phenyl]imino]-2,5-cyclohexadien-1-one | Phenol Blue |
| 2 | 2-Chloro-4-[[2-methyl-4-(diethylamino)phenyl]imino]-2,5-cyclohexadien-1-one | CAS 68155-95-3 |
| 3 | 4-[[4-(Diethylamino)phenyl]imino]-1,4-dihydronaphthalen-1-one | Colour Index 49705; C.I. Solvent Blue 22 |
| 4 | 4-[[4-(Dimethylamino)phenyl]imino]-1,4-dihydronaphthalen-1-one | Colour Index 49700 |
| 5 | 4-[[2-methyl-4-(diethylamino)phenyl]imino]-1,4-dihydronaphthalen-1-one | |
| 6 | 3-Methoxy-4-[[2-methyl-4-(diethylamino)phenyl]imino]-2,5-cyclohexadien-1-one | |
| 7 | 3-Chloro-4-[[2-methyl-4-(diethylamino)phenyl]imino]-2,5-cyclohexadien-1-one | |
| 8 | 2-Methyl-4-[[4-(4-morpholinyl)phenyl]imino]-2,5-cyclohexadien-1-one | |

TABLE 1a-continued

| Dye # | Identification[1,4] | Further Identification and/or Comments |
|---|---|---|
| 9 | same as #8 | |
| 10 | 2,6-Dichloro-4-[[4-(4-morpholinyl)phenyl]imino]-2,5-cyclohexadien-1-one | |
| 11 | 2,6-Dimethyl-4-[[4-(4-morpholinyl)phenyl]imino]-2,5-cyclohexadien-1-one | |
| 12 | 2,5-Dichloro-4-[[4-(diethylainino)phenyl]imino]-2,5-cyclohexadien-1-one | |
| 13 | 3-Methoxy-4-[[3-methoxy-4-(diethylamino)phenyl]imino]-2,5-cyclohexadien-1-one | |
| 14 | 2,6-Dichloro-4-[[2-methyl-4-(diethylamino)phenyl]imino]-2,5-cyclohexadien-1-one | |
| 15 | 3-[[4-(Diethylamino)-2-methylphenyl]imino]-oxo-N-phenyl-1,4-cyclohexadiene-1-carboxamide | CAS 102187-32-6 |
| 16 | 5-[[4-(Diethylamino)-2-methylphenyl]imino]-8-(5H)-quinolinone | CAS 54033-12-4 |
| 17 | 2,5-Dichloro-4-[[2-methyl-4-(diethylamino)phenyl]imino]-2,5-cyclohexadien-1-one | |
| 18 | 2,6-Dichloro-4-[4-ethoxyphenyl)imino]-2,5-cyclohexadien-1-one | |
| 19 | 2,6-Dichloro-4-[(2-methyl-4-ethoxy phenyl)imino]-2,5-cyclohexadien-1-one | |
| 20 | 2,6-Dimethyl4-[4-hydroxy phenyl)imino]-2,5-cyclohexadien-1-one | |
| 21 | 2,6-Dichloro-4-[(4-methoxy-1-naphthyl)imino]-2,5-cyclohexadien-1-one | |
| 22 | 2,6-Dichloro-4-[[4-(benzyloxy)phenyl]imino]-2,5-cyclohexadien-1-one | |
| 23 | 2,6-Dichloro-4-[(2,4-dimethoxyphenyl)imino]-2,5-cyclohexadien-1-one | |
| 24 | same as #18 | |
| 25 | same as #21 | |
| 26 | 2,6-Dichloro-4-[(4-methoxyphenyl)imino]-2,5-cyclohexadien-1-one | |
| 27 | same as #23 | |
| 28 | same as #23 | |
| 29 | 4-(phenylimino)-2,5-cyclohexadien-1-one | |
| 30 | 4-(1-naphthylimino)-2,5-cyclohexadien-1-one | |
| 31 | 4-(2-naphthylimino)-2,5-cyclohexadien-1-one | |
| 32 | same as #31 | |
| 33 | same as #29 | |
| 34 | 2,5-Bis(phenylamino)-4(phenylimino)-2,5-cyclohexadien-1-one | |
| 35 | same as #30 | |
| 36 | same as #30 | |
| 37 | 2,5-Dibromo-4-[(2,4-dibromophenyl)imino]-2,5-cyclohexadien-1-one | |
| 38 | same as #37 | |
| 39 | 2,3,5-Trichloro-4-[(2,4,6-trichlorophenyl)imino]-2,5-cyclohexadien-1-one | |
| 40 | 2,6-Dichloro-4-[4-[4-(dimethylamino)phenyl]-5-phenyl-(2H)-imidazol-2-ylidine]-2,5-cyclohexadien-1-one | |
| 41 | 2,6-Dichloro-4-[4,5-bis(4-hydroxyphenyl)-(2H)-imidazol-2-ylidine]-2,5-cyclohexadien-1-one | |
| 42 | 2,6-Dimethoxy-4-[4,5-bis(2-furyl)-(2H)-imidazol-2-ylidine]-2,5-cyclohexadien-1-one | |
| 43 | 2,6-Bis[1,1-(dimethyl)ethyl]4-[4,5-bis(2-furyl)-(2H)-imidazol-2-ylidene]-2,5-cyclohexadien-1-one | |
| 44 | 4-(phenylimino)-2,5-cyclohexadien-1-imine | |
| 45 | same as #44 | |
| 46 | Mono[(3-methyl-2-(3H)-benzothiazolylidene)hydrazono]2,5-cyclohexadiene-1,4-dione | CAS 38901-87-0 |
| 47 | 4-[(3-Chloro-4-oxo-2,5-cyclohexadien-1- | |

TABLE 1a-continued

| Dye # | Identification[1,4] | Further Identification and/or Comments |
|---|---|---|
| | ylidine]amino]-1,2-dihydro-1,5-dimethyl-2-phenyl-(3H)-pyrazol-3-one | |
| 48 | 4-[(3,5-Dichloro-4-oxo-2,5-cyclohexadien-1-ylidine)amino]-1,2-dihydro-1,5-dimethyl-2-phenyl-(3H)-pyrazol-3-one | CAS 51090-28-9 |
| 49 | 3-[(3,5-Dichloro-4-oxo-2,5-cyclohexadien-1-ylidine)amino]-2,5-dihydro-4,5-dimethyl-1-phenylpyrrol-2-one | |
| 50 | 4-(Phenylsulfonyl)imino-1-[4-[(phenylsulfonyl)imino]-2,5-cyclohexadien-1-ylidenyl]-2,5-cyclohexadiene | |
| 51 | 5-[5-(1,3-Diethylhexahydro-2,4,6-trioxo-5-pyrimidinyl)-2,4-pentadienylidene]-1,3-diethyl-2,4,6(1H,3H,5H)-pyrimidenetrione(triethylammonium salt) | CAS 54444-01-8 |
| 52 | 4-[6,6-Bis[(trifluoromethyl)sulfonyl]-1,3,5-hexatrienyl]-N,N-dimethylbenzenamine | CAS 58558-78-4 |
| 53 | 4-[4,4-Bis[(trifluoromethyl)sulfonyl]-1,3-butadienyl]-2-ethoxy-N,N-dimethylbenzenamine | |
| 54 | 4-[4,4-Bis[(trifluoromethyl)sulfonyl]-1,3-butadienyl]-2,5-dimethoxy-N,N-dimethylbenzenamine | |
| 55 | 9-[4,4-Bis[(trifluoromethyl)sulfonyl]-1,3-butadienyl]-2,3,6,7-tetrahydro-(1H,5H)-benzo[ij]quinolizine | CAS 149679-65-2 |
| 56 | 4-[4,4-Bis[(trifluoromethyl)sulfonyl]-1,3-butadienyl]-2,6-N,N-tetramethylbenzenamine | |
| 57 | 4-[5,5-Bis[(trifluoromethyl)sulfonyl]-2,4-pentadienylidene]-1,4-dihydro-1-methylquinoline | |
| 58 | 6,6-Bis[4-(dimethylamino)phenyl]1,3,5-hexatriene-1,1-bis(sulfonylfluoride) | CAS 149679-82-3 |
| 59 | 4-[4,4-Bis[(trifluoromethyl)sulfonyl]-1,3-butedienyl]-N,N-dimethylbenzenamine | CAS 58559-02-7; |
| 60 | 4-[3-[4-(Dimethylamino)phenyl-2-propenylidene]-2-phenyl-5(4H)-oxazolone | |
| 61 | 2,6-Dichloro-4-[[4-(acetainido)phenyl]imino]-2,5-cyclohexadien-1-one | |
| A | C.I. Disperse Yellow 4; Colour Index 12770 | azo dye |
| B | C.I. Solvent Yellow 14; Colour Index 12055; Sudan Orange R | azo dye |
| C | C.I. Solvent Red 24; Colour Index 26105 | bis azo dye |
| D | C.I. Solvent Orange 7; Colour Index 12140 | azo dye |
| E | C.I. Solvent Red 27; Orient Oil Red 5B | bis azo dye |
| F | C.I. Solvent Red 23; Colour Index 26100 | bis azo dye |
| G | C.I. Solvent Red 24; Colour Index 26105; Sudan Red 380 | bis azo dye |
| H | C.I. Solvent Red 182; Kayaset Red 802 | bis azo dye |
| I | C.I. Solvent Blue 35; Colour Index 61554; Sudan Blue 670 | anthraquinone |
| J | C.I. Solvent Blue 104; Nitrofast Blue 2B | anthraquinone |
| K | C.I. Solvent Blue 36; Colour Index 61551; Sumiplast Blue OA | anthraquinone |
| L | C.I. Solvent Violet 13; Colour Index 60725; Oplas Violet 730 | anthraquinone |
| M | C.I. Solvent Blue 111; Kayaset Blue 814 | anthraquinone |
| N | C.I. Acid Orange 52; Colour Index 13025; Methyl Orange | azo dye |
| O | C.I. Acid Red 88; Colour Index 15620; Fast Red A | azo dye |
| P | C.I. Acid Yellow 36; Colour Index 13065; Metanil Yellow | azo dye |
| Q | C.I. Acid Violet 3; Colour Index 16580; Victoria Violet | azo dye |
| 77 | 3H-Indolium, 3-[3-[4-(dimethylamino)phenyl]-2-propenylidene]-1-methyl-2-phenyl, 1,2,2,3,3,4,5,5,6,6-decafluoro-4-(pentafluoroethyl)-cyclohexanesulfonate salt | |
| 78 | Benzothiazolium, 3-(3-amino-3-oxopropyl)-2-[[4-[bis(2-chloroethyl)amino]phenyl]azo]-6-methoxy-, 1,2,2,3,3,4,5,5,6,6-decafluoro-4-(pentafluoroethyl)cyclohexanesulfonate salt | CAS 57230-19-0; C.I. Basic Blue 65; Colour Index 11076 |
| 79 | Benzothiazolium, 3-(3-amino-3-oxopropyl)-2-[[4-(diethylamino)phenyl]azo]-6-ethoxy-, chloride | CAS 12221-38-4; C.I. Basic Blue 67; Colour Index 11075 |
| 80 | Benzothiazolium, 3-(3-amino-3-oxopropyl)-2-[[4-(diethylamino)-2-methylphenyl]azo]-6-ethoxy-, 1,2,2,3,3,4,5,5,6,6-decafluoro-4-(pentafluoroethyl)cyclohexanesulfonate salt | CAS 12221-39-5; Basic blue 87; Colour Index 11185 |
| 81 | CAS 12221-40-8 | C. I. Basic Blue 68 |
| 82 | CAS 12270-14-3 | C.I. Basic Blue 76; Calcozing Blue 2B |
| 83 | CAS 12221-31-7 | C.I. Basic Blue 57 |
| 84 | CAS 12221-34-0 | C.I. Basic Blue 60 |
| 85 | Benzo[a]phenoxazin-7-ium, 9-(dimethlamino)-, 1,2,2,3,3,4,5,5,6,7-decafluoro-4-(pentafluoroethyl)-cyclohexanesulfonate salt | C.I. Basic Blue 6; Meldola Blue |
| 86 | 2-[4,4-bis[4-dimethylamino)phenyl]-1,3-butadienyl]-1-ethyl quinolinium, 1,2,2,3,3,4,5,5,6,6,-decafluoro-4-(pentafluoroethyl)cyclohexanesulfonate salt | |
| 87 | 4-[4,4-bis[4-dimetylamino)phenyl]-1,3-butadienyl]-1-ethyl quinolinium, 1,2,2,3,3,4,5,5,6,6-decafluoro-4-(pentafluoroethyl)cyclohexanesulfonate salt | CAS 80989-42-0 (cation) |
| 88 | Naphthol[2,1-d]thiazolium, 2-[4,4-bis[4-(dimethylamino)phenyl]-1,3-butadienyl]-3-ethyl-, 1,2,2,3,3,4,5,5,6,6-decafluoro-4-(pentafluoroethyl)cyclohexanesulfonate salt | |
| 89 | 2-[2-[4-(dimethylamino)phenyl]ethenyl]-1-phenyl-3-methyl quinoxalinium chloride | |
| 90 | Quinolinium, 2-[3-(5-chloro-1,3-dihydro-1,3,3-trimethyl-(2H)-indol-2-ylidene)-1-propenyl]-1-methyl-, 1,2,2,3,3,4,5,5,6,6-decafluoro-4-(pentafluoroethyl)cyclohexanesulfonate salt | |
| 91 | Benzothiazolium, 2-[[4-(dimethylamino)phenyl]azo]-6-methoxy-3-methyl-, 1,2,2,3,3,4,5,5,6,6-decafluoro-4-(pentafluoroethyl)cyclohexanesulfonate salt | C.I. Basic Blue 54 |
| 92 | Benz[cd]indolium, 2-[4-(diethylamino)-2-ethoxyphenyl]-1-ethyl-, 1,2,2,3,3,4,5,5,6,6-decafluoro-4-(pentafluoroethyl)-cyclohexanesulfonate salt | |
| 93 | 2-[p-(Dimethylamino)styryl]-1,3-dimethylquinoxalinium methylsulfate salt | |
| 94 | 2-[3-(5-chloro-1,3-dihydro-1,3,3-trimethyl-(2H)-indol-2-ylidene)-1-propenyl]-1-methylquinoxalinium, 1,2,2,3,3,4,5,5,6,6-decafluoro-4-(pentafluoroethyl)cyclohexanesulfonate salt | |
| 95 | C.I. Basic Blue 40 (tested as PECH Sulfonate salt) | Maxilon Blue RL |
| 96 | Benzothiazolium, 2-[[4-[ethyl(2-hydroxyethyl)amino]phenyl]azo]-6-methoxy-3-methyl-, methylsulfate salt | C.I. Basic Blue 41; Colour Index 11105; Deorlene Fast Blue RL; Basacryl Blue X-3GL |

TABLE 1a-continued

| Dye # | Identification[1,4] | Further Identification and/or Comments |
|---|---|---|
| 97 | Benzothiazolium, 2-[[4-[ethyl(2-hydroxyethyl)amino]phenyl]azo]-6-methoxy-3-methyl-, 1,2,2,3,3,4,5,5,6,6-decafluoro-4-(pentafluoroethyl)cyclohexanesulfonate salt | C.I. Basic Blue 41; Colour Index 11105, Deorlene Fast Blue RL; Basacryl Blue X-3GL |
| 98 | C.I. Basic Blue 42 (tested as PECH Sulfonate salt) | |
| 99 | C.I. Basic Blue 53 | Basacryl Blue 3RL |
| 100 | 3H-Indolium, 5-chloro-2-[5-(5-chloro-1,3-dihydro-1,3,3-trimethyl-2H-indol-2-ylidene)-1,3-pentadienyl]-1,3,3-trimethyl-, 1,2,2,3,3,4,5,5,6,6-decafluoro-4-(pentafluoroethyl)-cyclohexanesulfonate salt | |
| 101 | Basic Blue 142 | |
| 102 | Benz[cd]indolium, 2-[2-(9-ethyl-(9H)-carbazol-3-yl)ethenyl]-1-methyl-, 1,2,2,3,3,4,5,5,6,6-decafluoro-4-(pentafluoroethyl)cyclohexanesulfonate salt | |
| 104 | Benz[cd]indolium, 2-[2-[4-(dimethylamino)phenyl]-2-phenylethenyl]-1-methyl-, 1,2,2,3,3,4,5,5,6,6-decafluoro-4-(pentafluoroethyl)cyclohexanesulfonate salt | |
| 105 | Benz[cd]indolium, 2-[2,2-bis[4-(dimethylamino)phenyl]ethenyl]-1-methyl-, chloride salt | |
| 106 | Benz[cd]indolium, 2-[2,2-bis[4-(dimethylamino)phenyl]ethenyl]-1-methyl-, iodide salt | |
| 107 | Benz[cd]indolium, 2-[2-(2,3-dihydro-1-methyl-2-phenyl-1H-indol-3-yl)-2-(2-methylphenyl)ethenyl]-1-methyl-, 1,2,2,3,3,4,5,5,6,6-decafluoro-4-(pentafluoroethyl)cyclohexanesulfonate salt | |
| 108 | Pyrimidinium, 4-[5-(2,3-dihydro-1,3-dimethyl-2-oxo-4(1H)-pyrimidinylidene)-1,3-pentadienyl]-2,3-dihydro-1,3-dimethyl-2-oxo- | |
| 109 | 3H-Indolium, 2-[[3-[(1,3-dihydro-1,3,3-trimethyl-2H-indol-2-ylidene)methyl]-5,5-dimethyl-2-cyclohexen-1-ylidene]methyl]-1,3,3-trimethyl-, 1,2,2,3,3,4,5,5,6, 6-decafluoro-4-(pentafluoroethyl)cyclohexanesulfonate salt | |
| 110 | same as #100 | |
| 111 | Benz[cd]indolium, 2-[2-[4-(diethylamino)-2-methylphenyl]ethenyl]-1-methyl-, 1,2,2,3,3,4,5,5,6,6-decafluoro-4-(pentafluoroethyl)cyclohexanesulfonate salt | |
| 112 | 3H-Indolium, 3-[3-[4-[(dimethylamino)phenyl]-2-propenylidene]-1-methyl-2-(4-methoxyphenyl)-, trifluuoromethanesulfonate salt | |
| 113 | 3H-Indolium, 3-[(2,5-dimethyl-1-phenyl-(1H)-pyrrol-3-yl)methylene]-1,2-dimethyl-, trifluoromethanesulfonate salt | |
| 114 | 3H-Indolium, 3-[(2,5-dimethyl-1-phenyl-(1H)-pyrrol-3-yl)methylene]-1-methyl-2-phenyl-, trifluoromethanesulfonate salt | |
| 115 | 2-[2-[2-chloro-4-(dimethylamino)phenyl]ethenyl]-1-methylbenz[cd]indolium, 1,2,2,3,3,4,5,5,6,6-decafluoro-4-(pentafluoroethyl)-cyclohexanesulfonate salt | |
| 116 | same as #77 | |
| 117 | C.I. Basic Violet 22 (tested as PECH Sulfonate salt) | Basacryl Violet RL |
| 118 | C.I. Basic Red 15 (tested as PECH Sulfonate salt) | Genacryl Brilliant Red B |
| 119 | same as #94 | |
| 120 | same as #111 | |
| 121 | Benz[cd]indolium, 2-[2-[4-(dimethylamino)phenyl]ethenyl]-1-methyl-, 1,2,2,3,3,4,5,5,6,6-decafluoro-4-(pentafluoroethyl)-cyclohexanesulfonate salt | |
| 122 | Benz[cd]indolium,2-[2-[4-(dimethylamino)-2-ethoxyphenyl]ethenyl]-1-methyl, iodide salt | |
| 123 | 3H-Indolium, 2-[1-cyano-4,4-bis[4-(dimethylamino)phenyl]-1,3-butadienyl]-1,3,3-trimethyl-, 1,2,2,3,3,4,5,5,6,6-decafluoro-4-(pentafluoroethyl)-cyclohexanesulfonate salt | |

TABLE 1b

| Dye # | Initial Color | Gel time (seconds) | Color Change at 2 × GT[3] | Color Change at 24 hours | Solubility in silicone[2] | Color Change |
|---|---|---|---|---|---|---|
| 1 | purple | 265 | bleached | bleached | S | + |
| 2 | blue | 290 | bleached (light yellow) | bleached | S | + |
| 3 | blue | 320 | bleached (light yellow) | bleached | S | + |
| 4 | blue | 320 | bleached (light yellow) | bleached | SS | + |
| 5 | blue | 245 | bleached | bleached | S | + |
| 6 | blue | 217 | bleached | bleached | S | + |
| 7 | blue | 250 | bleached | bleached | I | |
| 8 | purple | 267 | bleached | bleached | S | + |
| 9 | purple | 305 | bleached | bleached | S | + |
| 10 | blue | 293 | bleached | bleached | I | |
| 11 | purple | 255 | no change | bleached | | |
| 12 | blue/green | 270 | bleached | bleached | S | + |
| 13 | blue | 230 | bleached | bleached | I | |
| 14 | aqua | 288 | no change | bleached | I | |
| 15 | green | 240 | bleached | bleached | S | + |
| 16 | blue | 505 | bleached before gel | bleached | S | + |
| 17 | green | 282 | partially | bleached | | |

TABLE 1b-continued

| Dye # | Initial Color | Gel time (seconds) | Color Change at 2 × GT[3] | Color Change at 24 hours | Solubility in silicone[2] | Color Change |
|---|---|---|---|---|---|---|
| | | | bleached | | | |
| 18 | purple | 277 | no change | bleached | | |
| 19 | purple | 284 | no change | bleached | | |
| 20 | orange | 257 | partially bleached | bleached | I | |
| 21 | blue | 270 | partially bleached | bleached | S | + |
| 22 | lavender | 240 | bleached | bleached | I | |
| 23 | purple | 261 | bleached | bleached | S | + |
| 24 | purple | 290 | no change | bleached | | |
| 25 | blue | 330 | partially bleached | bleached | | |
| 26 | purple | 335 | no change | bleached | | |
| 27 | purple | 420 | no change | bleached | | |
| 28 | purple | 330 | color changed | bleached | I | |
| 29 | orange | 246 | bleached | bleached | SS | |
| 30 | magenta | 270 | bleached | bleached | S | + |
| 31 | orange | 264 | bleached | bleached | S | + |
| 32 | orange | 333 | bleached | bleached | S | + |
| 33 | orange | 330 | bleached | bleached | S | + |
| 34 | orange | 240 | bleached | bleached | S | + |
| 35 | orange | 240 | bleached | bleached | S | + |
| 36 | magenta | 270 | bleached | bleached | | |
| 37 | magenta | 600 | no change | bleached | | |
| 38 | orange | 240 | no change | bleached | | |
| 39 | red, low intes. | 270 | bleached | bleached | | |
| 40 | blue/green | 290 | slight bleaching | bleached | I | |
| 41 | orange | 250 | slight bleaching | bleached | S | slight bleaching |
| 42 | magenta | 317 | bleached | bleached | S | slight bleaching |
| 43 | orange | 240 | no change | bleached | | |
| 44 | orange | 250 | bleached | bleached | I | |
| 45 | orange | 450 | no change | bleached | S | slight bleaching |
| 46 | orange | 241 | bleached | bleached | S | slight bleaching |
| 47 | orange | 258 | bleached | bleached | SS | |
| 48 | magenta | 260 | no change | bleached | S | no change |
| 49 | orange | 227 | bleached | bleached | S | slight |
| 50 | orange | 240 | bleached | bleached | | |
| 51 | fluor. blue | 246 | bleached | bleached | S | + |
| 52 | purple | 330 | bleached | bleached | S | + |
| 53 | purple/pink | 313 | bleached | bleached | S | + |
| 54 | purple/pink | 310 | bleached | bleached | S | + |
| 55 | purple | 326 | bleached | bleached | SS | + |
| 56 | purple | 332 | bleached | bleached | SS | + |
| 57 | purple | 310 | bleached | bleached | SS | + |
| 58 | blue | 258 | bleached | bleached | S | + |
| 59 | magenta | 306 | bleached | bleached | S | |
| 60 | magenta | 313 | bleached | bleached | SS | |
| 61 | lavender | 315 | not measured | bleached | S (Intense) | + |
| A | yellow | 270 | no change | | | |
| B | orange | 290 | no change | no change | | |
| C | red | 298 | no change | no change | | |
| D | orange | 276 | no change | no change | | |
| E | red | 212 | no change | slight | | |
| F | red | 194 | slight darkening | darker | | |
| G | red | 247 | no change | no change | | |
| H | red | 80 | no change | | | |
| I | blue | 377 | no change | no change | | |
| J | blue | 237 | no change | no change | | |
| K | blue | 103 | no change | | | |
| L | blue | 90 | no change | | | |
| M | blue | 81 | no change | | | |
| N | orange | 300 | no change | slight bleaching | | |
| O | lavender | 235 | no change | no change | | |
| P | yellow | 270 | no change | no change | | |
| Q | purple | 291 | no change | no change | | |
| 77 | blue | 150 | bleached before gel time | bleached | I | |
| 78 | blue | 219 | bleached | bleached | I | |

TABLE 1b-continued

| Dye # | Initial Color | Gel time (seconds) | Color Change at 2 × GT[3] | Color Change at 24 hours | Solubility in silicone[2] | Color Change |
|---|---|---|---|---|---|---|
| 79 | blue | 261 | bleached before gel time | bleached | I | |
| 80 | blue | 259 | bleached | bleached | I | |
| 81 | purple | 256 | bleached | bleached | I | |
| 82 | blue | 236 | bleached | bleached | I | |
| 83 | blue | 266 | bleached | bleached | I | |
| 84 | blue | 290 | bleached | bleached | I | |
| 85 | purple | 182 | bleached | bleached | I | |
| 86 | blue | 270 | bleached before gel time | bleached | I | |
| 87 | blue | 380 | bleached | bleached | I | |
| 88 | blue | 360 | bleached before gel time | bleached | | |
| 89 | blue | 255 | bleached | bleached | I | |
| 90 | blue | 205 | bleached | bleached | I | |
| 91 | blue | 246 | bleached | bleached | I | |
| 92 | blue | 267 | partially bleached | bleached | I | |
| 93 | blue | 232 | bleached | bleached | I | |
| 94 | blue | 240 | bleached | bleached | I | |
| 95 | blue | 220 | bleached | bleached | I | |
| 96 | purple | 164 | bleached | bleached | I | |
| 97 | purple | 193 | bleached | bleached | I | |
| 98 | purple | 196 | bleached | bleached | I | |
| 99 | blue | 278 | bleached | bleached | I | |
| 100 | blue | 258 | bleached | bleached | I | |
| 101 | blue | 287 | bleached | bleached | I | |
| 102 | blue | 320 | bleached | bleached | I | |
| 104 | green | 252 | bleached before gel time | bleached | I | |
| 105 | green | 252 | bleached before gel time | bleached | I | |
| 106 | blue/green | 370 | bleached before gel time | bleached | I | |
| 107 | green | 600 | bleached before gel time | bleached | I | |
| 108 | blue | 290 | belached before gel time | bleached | I | |
| 109 | purple | 166 | bleached | bleached | I | |
| 110 | blue | 582 | bleached | bleached | I | |
| 111 | blue/green | 368 | bleached before gel time | bleached | I | |
| 112 | blue | 278 | bleached | bleached | I | |
| 113 | orange | 371 | bleached | bleached | I | |
| 114 | orange | 260 | bleached | bleached | I | |
| 115 | green/blue | 409 | bleached | bleached | I | |
| 116 | blue | 955 | bleached before gel time | bleached | I | |
| 117 | magenta | 337 | bleached | bleached | I | |
| 118 | magenta | 337 | bleached | bleached | I | |
| 119 | magenta | 283 | bleached | bleached | I | |
| 120 | blue/green | 155 | bleached before gel time | bleached | I | |
| 121 | blue | 222 | bleached before gel time | bleached | I | |
| 122 | purple | 204 | bleached before gel time | bleached | I | |
| 123 | purple | 190 | bleached before gel time | bleached | I | |

Footnotes for Tables 1a and 1b:

[1]The "dye #" and "identification" correspond to the formula depicted in the attached drawings of dye structures. For brevity, the "dye #" listed in Table 1a will be used throughout the examples to refer to specific dyes. Notably, the cationioc dyes may comprise any suitable counter ion and are not limited to the specific counter ion(s) shown or depicted in the table or the attached drawings. Similarly, anionic dyes may comprise any suitable counter ion and are not limited to the specific counter ion(s) shown or depicted in the table or the attached drawings. Cationic dyes #77, 78, 80, 85–88, 90–92, 94–95, 97–98, 100, 102, 104, 107, 109–111, 115–121, and 123 were tested as PECH Sulfonate salts, though the CAS # or C.I.name or number listed in the table may describe the cation paired with a different anion.

[2]"S" = soluble; "I" = insoluble; "SS" = slightly soluble.

[3]"2 × GT" = twice the time elapsed to gel time.

[4]"PECH Sulfonate" = 1,2,2,3,3,4,5,5,6,6-decafluoro-4-(pentafluoroethyl)cyclohexane sulfonate.

The data of Table 1b show that neutral dyes 1 to 50 and 52 to 61, anionic dye 51, and cationic dyes 77 to 123 all exhibit a significant color change within 24 hours. Notably, dye 51 changed from being a fluorescent dye to a colorless nonfluorescent dye. In addition, many of these dyes exhibit a color change at some time less than two times the gel point ("2×GT"). Several dyes (e.g., 16, 77, 79, 86, 88, 104–108, 111, 116, and 120–123) exhibited bleaching prior to gelation and may be suitable as working time indicators. Dyes potentially suitable as set time indicators include: neutral dyes 1–10, 12–13, 15, 17, 22, 23, 29–36, 39, 42, 44, 46, 47, 49–50, 52–60, anionic dye 51, and cationic dyes 78, 80–85, 87, 89–102, 109, 110, 112–115, and 117–119.

In contrast, comparison dyes A to E and G to Q comprising neutral azo and anthraquinone dyes fail to exhibit a significant color change during any stage of the curing process. Comparison dye F exhibited a gradual darkening over 24 hours that did not correlate to any particular curing state.

Example 2

A number of dyes were further examined for solubility in the solventless silicone formulations of Preparatory Example 2. Those dyes that exhibited a noticeable color change within two times the gel point (as observed in Example 1) were evaluated for silicone solubility by the following procedure. Approximately 500 μg of the dye was transferred to a 1.5 dram (6 ml) glass vial. Approximately 1 ml of stock composition B1 was transferred to the vial with a disposable dropper, the solution was mixed with a spatula for approximately 3 minutes, and the mixture was examined visually for coloration of the silicone liquid. Coloration of the resin indicates that the dye was soluble or highly dispersed in the composition. Several dyes required 1 to 2 drops (~150 to 300 mg) of dichloromethane to induce solubility and were classified as "slightly soluble". Those dyes that required additional solvent (i.e., more than 1–2 drops) to color the composition were classified as "insoluble". The data is presented in Table 1b. Neutral dyes 1–6, 8–9, 12, 15, 16, 21, 23, 29–35, 41, 42, 45–49, 52–55, 57–59, and 61, and anionic dye 51 were all at least slightly soluble in stock composition B1. None of the cationic dyes were soluble in stock composition B1, although it is believed presently that such solubility could be achieved by modifying the anion, by modifying the dye cation (e.g., by incorporating a suitable solubilizing group), or perhaps by modifying the dye cation to provide an amphoteric dye.

Example 3

A variety of silicone soluble dyes were evaluated as "cure indicators" in solventless silicone formulations. Neutral dyes 1–6, 8–9, 12, 15, 16, 21, 23, 30–35, 41, 42, 45, 46, 48, 49, 52–58, and 61, and anionic dye 51 were independently evaluated in the following procedure. Approximately 500 μg of a dye was transferred to a 1.5 dram (6 ml) glass vial. To this was added approximately 1 ml of stock composition B1, e.g.. using a disposable dropper, the solution was mixed with a spatula for approximately 3 minutes and the mixture was examined visually for coloration of the resin and general solubility of the dye. Dichloromethane was used sparingly (1–2 drops) to promote solubility of less-soluble dyes. Approximately 1 ml of stock composition C1 was transferred to the colored solution, a timer was started and the composition was mixed thoroughly with a mixing stick for 30 seconds. The composition was placed against a white background and examined for the times at which gelation and visual color change occurred, and specifically if a color change occurred before the gel point, or within two times the gel point at room temperature. The data in Table 1b shows that nearly all of these dyes examined exhibited a partial or total color change within two times the gel point.

Example 4

A simple and effective method of selecting suitable cure-indicating dyes for compositions of this invention was developed and a variety of dyes were evaluated by this method. Dyes were evaluated according to the following "pentamethyldisiloxane test". Approximately 500 μg of dye was transferred to a 1.5 dram (6 ml) clear-glass, screw cap vial. To this was added, in order, 500 μl of dichloromethane, 100 μl of pentamethyldisiloxane, and either: (A) 25 μl of a catalyst solution comprising 25% by weight of a commercially available catalyst (PC075, available from United Chemical Technology, Inc. Bristol, Pa.) in dichloromethane; or (B) 10 μl of a commercially available catalyst solution (PC072, available from United Chemical Technology, Inc. Bristol, Pa.). The vial was capped, agitated for approximately 5 seconds at room temperature and the solution was observed for bleaching. Those dyes that exhibited bleaching within 5 minutes also exhibited a significant color change in the compositions of Example 1 and are believed to be suitable for use in this invention. Set out below in Table 4a are the dye number, dye type, results of the reactivity test and corresponding color change results from Table 1b. The data from Table 4a shows that dyes that fail to exhibit a significant color change in the reactivity test (indicated with a negative sign "–") are unlikely to function as visible cure monitors for the compositions of this invention; whereas, those dyes exhibiting a positive test response (indicated with a positive sign "+") are likely to serve as effective cure monitors. Notably, of the neutral anthraquinone and azo dyes tested, all failed the reactivity test and were ineffective cure monitors in the formulations of Example 1.

TABLE 4a

Comparison of Reactivity Test Results and Example 1 Results

| Dye Number | Dye Type | Reactivity Test Results | Table 1b Color Change Results |
|---|---|---|---|
| 1 | neutral | + | + |
| 2 | neutral | + | + |
| 4 | neutral | + | + |
| 16 | neutral | + | + |
| 52 | neutral | + | + |
| 59 | neutral | + | + |
| 60 | neutral | + | + |
| 77 | cationic | + | + |
| 78 | cationic | + | + |
| 82 | cationic | + | + |
| 91 | cationic | + | + |
| 96 | cationic | + | + |
| 97 | cationic | + | + |
| 99 | cationic | + | + |
| 101 | cationic | + | + |
| B | neutral | – | – |
| C | neutral | – | – |
| D | neutral | – | – |
| E | neutral | – | – |
| F | neutral | – | – |
| G | neutral | – | – |
| H | neutral | – | – |
| I | neutral | – | – |
| J | neutral | – | – |
| K | neutral | – | – |
| L | neutral | – | – |
| M | neutral | – | – |

TABLE 4a-continued

Comparison of Reactivity Test Results and Example 1 Results

| Dye Number | Dye Type | Reactivity Test Results | Table 1b Color Change Results |
|---|---|---|---|
| N | neutral | − | − |
| O | neutral | − | − |
| P | neutral | − | − |
| Q | neutral | − | − |

Example 5

A stock hydride and dye composition (H5) was prepared by combining and mixing in a glass container 0.0035 parts by weight of dye number 2 and 50 parts by weight of the crosslinker compound of Preparatory Example 2 ("XL1").

A stock vinyl and dye composition (V5) was prepared by combining and mixing in a glass container 0.0035 parts by weight of dye number 2 and 50 parts by weight of the vinyl terminated polydimethylsiloxane compound of Preparatory Example 2 ("LMWP").

A stock catalyst composition (C5) was prepared by combining and mixing in a glass container 5 parts by weight of the platinum catalyst solution described in Preparatory Example 2 and 5 parts by weight dichloromethane.

Five compositions comprising varying hydride/vinyl ratios were prepared according to the following procedure and evaluated for gelation and dye color bleaching. Ten grams of V5 was transferred to each of five glass vials along with 0.20, 0.30, 0.40, 0.50, and 0.60 grams respectively of H5. The compositions were mixed thoroughly, 0.10 grams of C5 was added to each vial, and the compositions again mixed until homogeneous. The samples were examined after standing 5 minutes and also after standing approximately 1 hour, and a determination of gelation and bleaching established. Set out below in Table 3 are the run number, proportions of H5, V5, and C5, approximate ratio of hydride to vinyl, and whether gelation and/or bleaching occurred following 5 and 60 minutes. The data shows that gelation occurs for all compositions (indicated as "+" sign) whereas complete bleaching (indicated as "+" sign) only occurs when the ratio of hydride to vinyl exceeds approximately one. Samples having a ratio of hydride to vinyl less than approximately one did not bleach (indicated as "−" sign). This result indicates that under the conditions of this example excess (i.e., unreacted) hydride is required to effect bleaching of the dye and that the reaction between hydride and vinyl occurs preferentially to the reaction between hydride and dye.

Example 6

A filled molding or dental impression material composition was prepared according to the following procedure. A filled base composition (B6) was prepared by transferring 25 parts by weight each of stock composition B1 from Preparatory Example 2 and dichloromethane to a 225 ml Semco mixing tube (available from Technical Resin Packaging Inc., Brooklyn Park, Minn.) and agitated by shaking. 0.0034 grams of dye #77 was dissolved in 1.2 grams of dichloromethane, added to the Semco cartridge and mixed by shaking. Ten grams of Quso WR-55 filler (available from Degussa Corp., Dublin, Ohio) was added to the cartridge and mixed 5 minutes on a Model 388 automatic Semkit Mixer (available from Technical Resin Packaging Inc., Brooklyn Park, Minn.). 50.0 grams of Imsil A-25 filler (available from Micronized Unimen Specialty Minerals, Cairo, Ill. as Imsil A-25 micro crystalline silica) was then added to the cartridge and mixed for 10 minutes. Finally, an additional 5 grams each of B1 and dichloromethane was added to the cartridge and mixed for 5 minutes yielding a light blue paste.

A filled catalyst composition (C6) was prepared by transferring 25 parts by weight each of stock composition C1 from Preparatory Example 2 and dichloromethane to a 225 ml Semco mixing tube and agitated by shaking. 8.3 grams of Quso filler was added to the tube, mixed 5 minutes on a model 388 Semkit Mixer, followed by the addition of 41.7 grams of Imsil A-25 filler and 12 minutes mixing. This procedure yielded a white paste.

Approximately equal volumes of B6 and C6 were transferred to independent chambers of a dual barrel mixing cartridge which were sealed with inserts. The cartridge was inserted into a hand held dispensing apparatus, a Kenics static mixing tip was placed on the cartridge, and the catalyst (C1) and base (B1) mixed by co-extrusion through the mixing tip. A Kenics static mixer consists of a circular pipe within which are fixed a series of short helical elements of alternating left- and right-hand pitch. The helical design of the central element causes a transverse flow to arise in the plane normal to the pipe axis. As a consequence, radial mixing of the two compositions is achieved. A complete description of the fluid mechanics of a Kenics static mixer may be found on pages 327 and 328 of *Fundamentals of Polymer Processing*, by Stanley Middleman. The silicone compound begins to react (i.e., crosslink) upon mixing the two compositions together.

The mixed paste became rigid and exhibited a color change from light blue to pale blue within about 6 minutes.

Example 7

A solventless, filled, molding or dental impression material composition was prepared according to the following procedure. A filled base composition (B7) was prepared by transferring 200 grams of stock composition B1 from Preparatory Example 2, 2.8 grams Silwet L-77 (available from

TABLE 5a

| Run | H5 (gms) | V5 (gms) | C5 (gms) | Hydride: vinyl ratio | Gel | Bleaching at 5 min | Bleaching at 60 min |
|---|---|---|---|---|---|---|---|
| 1 | 0.20 | 10.0 | 0.10 | 0.50 | + | − | − |
| 2 | 0.30 | 10.0 | 0.10 | 0.75 | + | − | − |
| 3 | 0.40 | 10.0 | 0.10 | 1.00 | + | slight bleaching | slight bleaching |
| 4 | 0.50 | 10.0 | 0.10 | 1.25 | + | + | + |
| 5 | 0.60 | 10.0 | 0.10 | 1.50 | + | + | + |

OSi Specialties, Inc., Lisle, Ill.), and 20 grams Quso WR-55 to a Ross double planetary mixer. The materials were mixed for 5 minutes at 40 rpm. 135 grams of Imsil A-25 filler were then added to the mixer pot and mixed for 5 minutes. Finally, 45.0 grams of Imsil A-25 were added to the mixer and mixed under vacuum for 35 minutes yielding a white paste.

A filled catalyst composition (C7) was prepared by dissolving in a Ross mixer approximately 0.0254 grams of dye #2 in 187 grams of stock composition C1 from Preparatory Example 2. 2.62 grams Silwet L-77 and 18.7 grams Quso WR-55 were added to the Ross mixer and mixed for 5 minutes at 40 rpm. A 126 gram aliquot of Imsil A-25 filler was added to the mixer, mixed for 5 minutes followed by the addition of an additional 42 grams of Imsil A-25 and mixing for 35 minutes under vacuum at 40 rpm. This process yielded a blue catalyst paste.

Approximately equal volumes of B7 and C7 were transferred to independent chambers of a dual-barrel mixing cartridge. The cartridge was inserted into a hand-held dispensing apparatus, a static-mixing tip placed on the cartridge and the catalyst (C7) and base (B7) mixed by co-extrusion through the static-mixing tip. The mixed paste stiffened, then became rigid and exhibited a color change from light blue to white at approximately the same time of 3 to 3.5 minutes.

Example 8

The effects of varying levels of hydride/vinyl ratio, vinyl/platinum ratio and dye concentration upon bleaching time and setting time were examined by utilizing a three-variable "central composite" design experiment. Experiments of this type are extremely useful in examining the effects of reactive ingredients and optimizing the composition formula to prepare practical, useful impression materials.

As shown in Table 8a, catalyst impression materials (C8) were individually prepared by adding the indicated parts by weight of platinum catalyst (a solution of 2.55% Pt by weight in vinyl-terminated polydimethylsiloxane as described in Preparatory Example 1), vinyl-terminated polydimethylsiloxane ("LMWP" as described in Preparatory Example 2) and Acrosil R202 (a fumed silica available from Degussa Corp., Dublin, Ohio) to a 225 ml Semco tube and mixing by means of a model 388 Semkit mixer for 7 minutes. Base impression materials (C8) were prepared similarly by adding the indicated parts by weight of crosslinker ("XL1" as described in Preparatory Example 2), vinyl-terminated polydimethylsiloxane "LMWP", dye #2 (added as a 0.05 w/w solution in $CHCl_3$), and Aerosil R202 to a 225 ml Semco tube and mixing by means of a model 388 Semkit mixer for 7 minutes.

Approximately equal volumes of C8 and B8 were added to independent chambers of a dual-barrel mixing cartridge and mixed by extruding through a static-mixing element. Curing parameters were determined on a Monsanto Model R100 oscillating disc rheometer and are presented in Table 8b. The rheometer measures torque as a function of time. "T5" is the amount of time it takes for the torque to reach 5% of maximum value. "T90" is the amount of time it takes for the torque to reach 90% of maximum value. These values approximate the working time and setting time of the composition, respectively.

Table 8b shows cure times (T90 and T5) and bleach time (BT) at 27° C. for each sample. The SiH/Vinyl ratio, Vinyl/Pt ratio, and dye concentration were all found to be significant contributors to the bleach time. It is especially useful to examine the data with reference to the bleach time and BT/T90 ratio. The SiH/Vinyl ratio was the most significant variable (i.e., had the strongest effect on BT). Runs #1, 3, 5, 7, and 13 all have SiH/Vinyl less than 1.0. Notably, bleaching was observed only for run #3 (which had low dye concentration and a high Vinyl/Pt ratio).

By examining selected pairs of runs one can determine the effect of individual variables. For example, comparing run #2 to #4, run #6 to #8, or run #15 to #16 one can isolate the effect of changing the vinyl/Pt ratio. In general, increasing the amount of Pt decreases both BT and the BT/T90 ratio. By comparing run #2 to #6, run #4 to #8, or run #17 to #18 one can isolate the effect of dye concentration. In general, raising the dye concentration increases the BT and BT/T90 ratio.

The BT/T90 ratio is indicative of the relationship between setting time and bleaching time. Setting time indicator compositions may be generalized to those materials having a BT/T90 ratio of approximately 1.0. Compositions with BT/T90 ratios greater than about 1.2 may have less utility in this application. Compositions with a BT/T5 ratio of approximately 1.0 may be viable working time indicators.

TABLE 8a

| | | Catalyst Paste (parts) | | | Base Paste (parts) | | | |
|---|---|---|---|---|---|---|---|---|
| Run | Catalyst | Vinyl terminated polydimethylsiloxane | Aerosil R202 | Crosslinker | Vinyl terminated polydimethylsiloxane | Dye #2 | Aerosil R202 |
| 1 | 0.0148 | 49.985 | 5 | 3.65 | 46.35 | 0.00061 | 5 |
| 2 | 0.013 | 49.987 | 5 | 15.4 | 34.6 | 0.00061 | 5 |
| 3 | 0.0931 | 49.907 | 5 | 3.64 | 46.36 | 0.00061 | 5 |
| 4 | 0.0819 | 49.918 | 5 | 15.39 | 34.61 | 0.00061 | 5 |
| 5 | 0.0148 | 49.985 | 5 | 3.65 | 46.35 | 0.01020 | 5 |
| 6 | 0.013 | 49.987 | 5 | 15.4 | 34.6 | 0.01020 | 5 |
| 7 | 0.0931 | 49.907 | 5 | 3.64 | 46.36 | 0.01020 | 5 |
| 8 | 0.0819 | 49.918 | 5 | 15.39 | 34.61 | 0.01020 | 5 |
| 9 | 0.0357 | 49.964 | 5 | 7.66 | 42.34 | 0.00250 | 5 |
| 10 | 0.0357 | 49.964 | 5 | 7.66 | 42.34 | 0.00250 | 5 |
| 11 | 0.0357 | 49.964 | 5 | 7.66 | 4.234 | 0.00250 | 5 |
| 12 | 0.0357 | 49.964 | 5 | 7.66 | 42.34 | 0.00250 | 5 |
| 13 | 0.0377 | 49.962 | 5 | 2.25 | 47.75 | 0.00250 | 5 |

TABLE 8a-continued

| | Catalyst Paste (parts) | | | Base Paste (parts) | | | |
|---|---|---|---|---|---|---|---|
| Run | Catalyst | Vinyl terminated polydi- methyl- siloxane | Aerosil R202 | Cross- linker | Vinyl terminated polydimethyl- siloxane | Dye #2 | Aerosil R202 |
| 14 | 0.0297 | 49.97 | 5 | 23.03 | 26.97 | 0.00250 | 5 |
| 15 | 0.00795 | 49.99 | 5 | 7.66 | 42.34 | 0.00250 | 5 |
| 16 | 0.1596 | 49.84 | 5 | 7.65 | 42.35 | 0.00250 | 5 |
| 17 | 0.0357 | 49.964 | 5 | 7.66 | 42.34 | 0.00025 | 5 |
| 18 | 0.0357 | 49.964 | 5 | 7.66 | 42.34 | 0.02500 | 5 |
| 19 | 0.0357 | 49.964 | 5 | 7.66 | 42.34 | 0.00250 | 5 |
| 20 | 0.0357 | 49.964 | 5 | 7.66 | 42.34 | 0.00250 | 5 |

TABLE 8b

| Run | SiH/Si-Vi | Si-Vi/Pt | Dye, grams | Bleach Time (sec) | T90 (sec) | T5 (sec) | Bleach Time/T90 | Bleach Time/T5 |
|---|---|---|---|---|---|---|---|---|
| 1 | 0.82 | 112.4 | 0.00061 | >10,000 | 586 | 259 | >20 | >40 |
| 2 | 3.95 | 112.4 | 0.00061 | 82 | 114 | 85 | 0.72 | 0.96 |
| 3 | 0.82 | 17.9 | 0.00061 | 160 | 371 | 164 | 0.43 | 0.98 |
| 4 | 3.95 | 17.9 | 0.00061 | 52 | 82 | 45 | 0.63 | 1.16 |
| 5 | 0.82 | 112.4 | 0.01020 | >10,000 | 552 | 240 | >20 | >40 |
| 6 | 3.95 | 112.4 | 0.01020 | 110 | 94 | 59 | 1.17 | 1.86 |
| 7 | 0.82 | 17.9 | 0.01020 | >10,000 | 354 | 153 | >30 | >60 |
| 8 | 3.95 | 17.9 | 0.01020 | 70 | 82 | 45 | 0.85 | 1.56 |
| 9 | 1.8 | 44.8 | 0.00250 | 174 | 178 | 109 | 0.98 | 1.60 |
| 10 | 1.8 | 44.8 | 0.00250 | 164 | 191 | 114 | 0.86 | 1.44 |
| 11 | 1.8 | 44.8 | 0.00250 | 167 | 178 | 110 | 0.94 | 1.52 |
| 12 | 1.8 | 44.8 | 0.00250 | 170 | 189 | 113 | 0.9 | 1.50 |
| 13 | 0.5 | 44.8 | 0.00250 | >10,000 | 411 | 250 | >25 | >40 |
| 14 | 6.5 | 44.8 | 0.00250 | 39 | 52 | 32 | 0.75 | 1.22 |
| 15 | 1.8 | 201 | 0.00250 | 272 | 273 | 147 | 1 | 1.85 |
| 16 | 1.8 | 10 | 0.00250 | 102 | 162 | 85 | 0.63 | 1.20 |
| 17 | 1.8 | 44.8 | 0.00025 | 136 | 175 | 108 | 0.78 | 1.26 |
| 18 | 1.8 | 44.8 | 0.02500 | 232 | 180 | 111 | 1.29 | 2.09 |
| 19 | 1.8 | 44.8 | 0.00250 | 160 | 182 | 112 | 0.88 | 1.43 |
| 20 | 1.8 | 44.8 | 0.00250 | 187 | 176 | 109 | 1.06 | 1.72 |

EXAMPLE 9

Several other dyes evaluated in Examples 1 and 4 were compounded into filled molding or dental impression material compositions according to the following procedure.

Filled catalyst compositions (C9) were prepared by adding 0.014 parts of dye dissolved in 0.7 ml of $CHCl_3$ to a stock catalyst solution containing 96.73 parts vinyl-terminated polydimethylsiloxane ("LMWP", from Preparatory Example 2), 0.76 parts Silwet L-77, and 2.51 parts platinum catalyst ("Karstedt" type Pt catalyst, 2 to 3% Pt in vinyldimethylsiloxy-terminated polydimethylsiloxane, prepared in a similar manner as described in Preparatory Example 1a and having a viscosity of 2.0 Pa s.) in an 225 ml Semco tube. 10 parts Quso WR-55 were added and mixed by means of a model 388 Semkit mixer for 5 minutes. 60 parts Imsil A-25 were added and mixed for 5 minutes followed by 30 parts Imsil A-25 and mixing for an additional 30 minutes to yield colored pastes.

Filled base compositions (B9a and B9b) were prepared by the following procedure. B9a: 178 parts crosslinker ("XL1"), 620 parts vinyl terminated polydimethylsiloxane ("LMWP"), 11.2 parts Silwet L-77, and 80 parts Quso WR-55 were added to a 1 gallon Ross mixer and mixed for 5 minutes at 30 rpm. 480 parts Imsil A-25 were added and mixed for 5 minutes at 30 rpm. Finally, 240 parts Imsil A-25 were added and mixed under vacuum for 50 minutes at 30 rpm to yield an off-white paste. B9b: 66 parts crosslinker ("XL1"), 231 parts vinyl terminated polydimethylsiloxane ("LMWP"), 4.2 parts Silwet L-77, and 30 parts Quso WR-55 were added to a 1 quart Ross mixer and mixed 5 minutes at 40 rpm. 179 parts Imsil A-25 were added and mixed for 5 minutes at 40 rpm. Finally, 90 parts Imsil A-25 were added and mixed for 50 minutes under vacuum at 40 rpm to yield an off-white paste.

Approximately equal volumes of C9 and B9a (runs 1, 2, and 6–10) or C9 and B9b (runs 3–5) were placed in the chambers of a dual-barrel mixing cartridge and mixed by extruding through a static-mixing element. The mixed pastes cured in approximately 3 to 3.5 minutes (cure time defined as T90 at 27° C.). The bleach times, defined as the amount of time it takes to bleach completely (as compared to a reference prepared without dye) are listed in Table 9a below.

TABLE 9a

| Run | Dye | Initial Color | Bleach Time (80° F.) |
|---|---|---|---|
| 1 | none | off white | NA |
| 2 | #2 | blue | 4 minutes |
| 3 | #53 | pink | 4 minutes |
| 4 | #60 | purple | 6 minutes |
| 5 | #56 | pink | 4 minutes |
| 6 | H | pink | DNBC[1] |
| 7 | E | pink | DNBC[1] |
| 8 | L | purple | DNB[2] |
| 9 | K | blue | DNB[2] |
| 10 | M | blue | DNB[2] |

Footnotes for Table 9a:
[1]Approximately 80–90% bleaching occurred in 90–120 minutes; however, the sample did not bleach completely ("DNBC") even after 72 hours.
[2]"DNB" = did not bleach.

EXAMPLE 10

Several other filled molding or dental impression compositions were prepared utilizing dye #2 and also a non-cure-indicating pigment to impart both a unique initial-mix and final-cure colors.

Cure-indicating base impression material composition (B10) was prepared by adding 22.4 parts Silwet L-77, 356 parts crosslinker ("XL1"), 1239 parts vinyl terminated polydimethylsiloxane ("LMWP"), and 0.23 parts dye #2 (added as a 0.05 w/w solution in $CHCl_3$) to a Ross mixer and mixing 5 minutes at 30 rpm. 160 parts Quso WR-55 were then added and mixed for 5 minutes at 30 rpm. 960 parts Imsil A-25 were added and mixed for 5 minutes at 30 rpm followed by 480 parts Imsil A-25 and an additional 50 minutes mixing at 30 rpm under vacuum to yield a blue base impression paste.

Catalyst impression material compositions (C10) were prepared by adding 11.2 parts Silwet L-77, 783 parts vinyl terminated polydimethylsiloxane ("LMWP"), 16.4 parts Pt catalyst (as described in Preparatory Example 1a but diluted in "LMWP"), and either 8 parts of red pigment (available from Warner-Jenkinson, St. Louis, Mo. as #K7183 D&C Red #7 Calcium Lake) or 16 parts of yellow pigment (available from Reed Spectrum, Inc., Minneapolis, Minn. as Yellow #1604404) to a Ross mixer and mixing for 5 minutes at 30 rpm. 80 parts Quso WR-55 was added and mixed 5 minutes at 30 rpm. 480 parts Imsil A-25 were added and mixed for 5 minutes at 30 rpm followed by 240 parts Imsil A-25 and an additional 50 minutes mixing at 30 rpm under vacuum to yield pinkish-red (C10a) or yellow (C10b) catalyst impression pastes.

Approximately equal volumes of C10 and B10 were placed in the chambers of a dual-barrel mixing cartridge and mixed by extruding through a static mixing-element. The mixed pastes cured in approximately 3 to 3.5 minutes (27° C.). The initial color of the C10a/B10 impression paste is purple and bleaches to a pinkish-red color in approximately 3.5 minutes. The initial color of the C10b/B10 impression paste is green and bleaches to a yellow color in approximately 3.5 minutes.

EXAMPLE 11

The effect of the hydrosilation inhibitor diethyl maleate (DEM) on the gel time and bleaching time of curable compositions at 25° C. and 85° C. was examined. A stock dye catalyst solution (SDC11) was prepared by transferring 0.0034 grams of dye #2 and approximately 0.10 grams of dichloromethane to glass jar. Approximately 50.0 grams of stock composition C1 (from Preparatory Example 2) was transferred to the glass jar and mixed with a wooden tongue blade until homogeneous. Similarly, a stock dye base solution (SDB11) was prepared by transferring 0.0034 grams of dye #2, approximately 0.10 grams of dichloromethane and approximately 50.0 grams of stock composition B1 (from Preparatory Example 2) to another glass jar and the components were mixed with a wooden tongue-depression blade until homogeneous. Three samples containing various amounts of diethyl maleate were prepared by transferring 0, 1, or 5 μl respectively of diethyl maleate to separate 1.5 dram glass vials. Approximately 0.50 grams of the stock solution SDC11 and 0.50 grams of the stock solution SDB11 were transferred to the respective vials, mixed thoroughly for 30 seconds with a mixing stick and examined for gel time and bleaching time at 25° C.

A second set of similar samples was evaluated for gel and bleaching time at 85° C. A glass microscope slide was placed on a hot plate heated to 85° C. Three samples containing various amounts of diethyl maleate were prepared by transferring 0, 1, or 5 μl respectively of diethyl maleate to separate 1.5 dram glass vials. Approximately 0.50 grams of the stock solution SDC11 and 0.50 grams of the stock solution SDB11 were transferred to the respective vials, mixed thoroughly for 30 seconds with a mixing stick and one drop (~0.05 grams) of the mixture applied to the heated glass slide. These samples were probed and visually inspected both for gel time and for bleach time. Set out in Table 11a are the amounts of diethyl maleate added and the gel and bleaching times at 25° and 85° C.

TABLE 11a

| Run # | DEM (ml) | Gel time (25° C.) | Bleach time (25° C.) | Gel time (85° C.) | Bleach time (85° C.) |
|---|---|---|---|---|---|
| 1 | 0 | 135 sec. | 210 sec. | 8 sec. | 12 sec. |
| 2 | 1 | 1.5 hrs. | 8 hrs. | 22 sec. | 20 sec. |
| 3 | 5 | >>48 hrs | Significant bleaching at 48 hrs. | 81 sec. | 15 sec. |

The data show that the addition of DEM to hydrosilation-curable compositions results in room-temperature-stable compositions that can be cured and cure-monitored at elevated temperatures. Increasing levels of DEM result in bleaching times that occur at shorter times relative to gel times at 85° C. thus providing potential indicators for working time, gel time and setting time.

EXAMPLE 12

The effect of two additional active-hydrogen (proton) sources on the gel time and bleaching time of curable compositions at room temperature was evaluated. Four samples containing various amounts of dodecanol ("DDL") were prepared by transferring 0, 5, 10 or 20 μl respectively of DDL to separate 1.5 dram glass vials. Approximately 0.50 grams of the stock solution SDC1 and 0.50 grams of the stock solution SDB1 were transferred to the respective vials, mixed thoroughly for 30 seconds with a mixing stick and examined for gel time and bleach time at 25° C.

A second set of samples containing various amounts of acetic acid ("AA") were evaluated for gel and bleaching time at 25° C. Four samples containing various amounts of acetic acid were prepared by transferring 0, 1, 5 or 10 μl respectively of AA to separate 1.5 dram glass vials. Approximately 0.50 grams of the stock solution SDC1 and 0.50 grams of the stock solution SDB1 were transferred to the respective vials, mixed thoroughly for 30 seconds with a mixing stick and examined for gel time and bleach time at 25° C.

Results for both experiments are shown in Table 12a.

TABLE 12a

| Run # | Indicator adjuvent | (μl) | Gel time (25° C.) | Bleach time (25° C.) |
|---|---|---|---|---|
| 1 | DDL | 0 | 158 sec. | 244 sec. |
| 2 | DDL | 5 | 160 sec. | 244 sec. |
| 3 | DDL | 10 | 167 sec. | 250 sec. |
| 4 | DDL | 20 | 190 sec. | 310 sec. |
| 5 | AA | 0 | 150 sec. | 220 sec. |
| 6 | AA | 1 | 154 sec. | 150 sec. |
| 7 | AA | 5 | 240 sec. | 140 sec. |
| 8 | AA | 10 | 600 sec. | ~150 sec. (slight blue tinge) |

The data show that the addition of DDL to hydrosilation-curable compositions results in minimal change to gel and bleach times. In contrast, the addition of AA results in longer gel times and shorter bleach times, respectively, at room temperature. Thus the addition of adjuvents to compositions of the present invention can be utilized to adjust the relationship between the color change and the cure reaction.

EXAMPLE 13

Indication of cure inhibition is demonstrated in the following examples utilizing the cure-indicating dental impression materials previously exemplified in Examples 9 and 10. A commercially available "acrylate" type adhesive (Scotchbond Multipurpose Dental Adhesive "SBMP" available from 3M, St. Paul, Minn.) was applied to approximately a 5 mm×5 mm section of a glass microscope slide. Acrylate adhesives sometimes are observed to retard or inhibit the setting of dental impression materials that cure via a hydrosilation mechanism. A purple impression paste from Example 10 (C10a/B10) was extruded through a static mixer and applied over much of the slide including the section coated with the SBMP. The bulk of the impression material exhibited a color change from purple to red/pink in approximately 3.5 minutes. Notably, however, the area previously coated with SBMP maintained a purplish coloring (indicating that this area was not fully cured). Similar results were obtained for compositions C10b/B10 (from Example 10) and Run 2 of Example 9.

A two-part (blue catalyst and white base) cure-indicating impression putty similar to that described in Example 17 was evaluated under two sets of mixing conditions. Approximately 5 grams each of catalyst and base putties were mixed by hand, wearing vinyl gloves, until a homogeneous blue paste was obtained. The paste was rolled into a ball and allowed to set. A second comparable mix of the catalyst and base compositions was prepared using latex gloves. Latex gloves sometimes are known to retard or inhibit the setting of dental impression materials that cure via a hydrosilation mechanism. This ball of material also was allowed to set.

Both balls cured in bulk. The sample mixed with vinyl gloves bleached to a white homogeneous sample. However, the sample mixed with latex gloves exhibited blue and white striations. The striations are believed to be indicative of incomplete curing due to contamination by the latex gloves.

EXAMPLE 14

A stock impression base paste (B14) was formulated by mixing together 150 parts vinyl terminated polydimethylsiloxane having a viscosity of 2.0 Pa s ("LMWP"), 4.1 parts organohydrosiloxane crosslinker (PS 122.5, available from United Chemical Technology, Inc., Bristol, Pa.), and 30 parts Imsil A-25 filler.

A stock solution of dye M was prepared by dissolving 0.05 parts dye in 0.87 parts toluene. A stock solution of dye #2 (DS14) was prepared by dissolving 0.05 parts dye #2 in 1.74 parts of toluene. Additionally, a stock paste of dye #2 (DP14) was prepared by dispersing 5 parts dye and 5 parts Aerosil R976 fumed silica (available from Degussa Corp., Dublin, Ohio) in 90 parts vinyldimethyl-terminated polydimethyl siloxane with a viscosity of 1.0 Pa s ("VLMWP" available from OSi Specialties Inc., Danbury, Conn.) using a three-roll mill. A stock solution of chloroplatinic acid ($H_2PtCl_6 \times 6H_2O$, "CPA") catalyst was prepared by dissolving 0.04 parts CPA in 0.79 parts isopropanol.

Cure-indicating formulations were prepared by adding sufficient amounts of dye and catalyst to 30.7 parts of base paste (B14) to give 100 ppm dye (based on LMWP) and 30 ppm Pt (based on LMWP), and mixing by hand. Formulations were monitored for gel point, cure point, and bleach point as shown in Table 14a.

TABLE 14a

| Run | Dye | Gel Point | Cure Point | Bleach Point |
|---|---|---|---|---|
| 1 | M | 70–80 min. | 180–240 min. | DNB[1] |
| 2 | #2[2] | >300 min. | <1200 min. | PB[3] |
| 3 | #2[4] | >300 min. | <1200 min. | PB |

[1] "DNB" = did not bleach after 72 hours.
[2] As a toluene solution (DS14).
[3] "PB" = partial bleaching occurred.
[4] As a dispersed paste (DP14).

Notably, comparison dye M did not exhibit bleaching over the 72 hour period after the curing reaction was begun, while dye #2 exhibited some partial bleaching in this non-preferred composition.

EXAMPLE 15

The above experiment was repeated with the following changes: 1) the dye concentration was increased to 200 ppm based on LMWP; 2) a CPA stock solution was prepared by dissolving 0.10 parts CPA in 0.79 parts isopropanol; and 3) 0.15 parts Silwet L-77 surfactant per 15.3 parts impression paste was added to the indicated run numbers. Formulations were monitored for gel point, cure point, and bleach point as shown in Table 15a.

TABLE 15a

| Run | Silwet | Dye | Gel Point | Cure Point | Bleach Point |
|---|---|---|---|---|---|
| 1 | No | M | 120 min. | <1320 min. | DNB[1] |
| 2 | Yes | M | >420 min. | <1320 min. | DNB |
| 3 | No | #2[2] | >1440 min. | <2880 min. | DNB |
| 4 | Yes | #2[2] | 230 min. | <1320 min. | 230 min. |

[1] DNB - did not bleach after 72 hours.
[2] As a toluene solution (DS14).

The composition containing Silwet and Dye #2 (Run 4) exhibited bleaching, while the composition containing Silwet and comparison dye M (Run 2) did not bleach.

EXAMPLE 16

A stock catalyst solution (C16A) was prepared by combining 400 parts of vinyldimethyl-terminated poly(dimethylsiloxane) with a viscosity of 2.0 Pa s ("LMWP") with 11 parts of Pt catalyst (from Preparatory Example 1a). A stock catalyst solution (C16S) was prepared by combining 400 parts of vinyldimethyl-terminated poly(dimethylsiloxane) with a viscosity of 2.0 Pa s ("LMWP") with 11 parts of Pt catalyst (from Preparatory Example 1a) and 8 parts Silwet L-77 surfactant. A stock base solution (B16) was prepared by combining 12.5 parts organohydropolysiloxane crosslinker ("XL1") with 0.25 parts 1,1,3,3-tetramethyl-1,3-divinyldisiloxane inhibitor ("DVTMDS"). 0.04 parts DP14 was added to 20 parts of catalyst solutions C16A or C16S. Synthetic or mineral fillers were added according to Table 16a to prepare impression material pastes. These pastes were cured by adding 2.55 parts of base stock solution B16 and mixing for 120 seconds. The initial color, gel time, cure time, and bleach time for each run are listed in Table 16a.

TABLE 16a

| Run[1] | Filler[2], parts | Color | Gel Time | Cure Time | Bleach Time |
|---|---|---|---|---|---|
| 1A | none | Blue | 6.5 min. | 9 min. | 9 min. |
| 1S | none | Blue | 6.5 min. | 9 min. | 9 min. |
| 2A | Imsil, 4 | Blue-grey | 6.5 min. | 9 min. | >20 min. |
| 2S | Imsil, 4 | Blue | 6.5 min. | 9 min. | 9 min. |
| 3A | Vicron, 4 | Blue | 6.0 min | 9 min. | 9 min. |
| 3S | Vicron, 4 | Blue | 6.0 min. | 9 min. | 9 min. |
| 4A | Talc, 4 | Blue-grey | 6.0 min. | 9 min. | >15 min. |
| 4S | Talc, 4 | Blue | 6.0 min. | 9 min. | 12 min. |
| 5A | Alumina, 4 | Blue | 5.0 min. | 8 min. | 8 min. |
| 5S | Alumina, 4 | Blue | 6.0 min. | 9 min. | 9 min. |
| 6A | Quso, 2 | Blue | 5.0 min. | 7 min. | 7 min. |
| 6S | Quso, 2 | Blue | 5.0 min. | 7.5 min. | 7.5 min. |
| 7A | Aerosil R976, 1 | Blue-green | 5.0 min. | 7 min. | >20 min. |
| 7S | Aerosil R976, 1 | Blue | 5.0 min. | 7 min. | 7 min. |
| 8A | Cabosil M5, 1 | Green | 4.0 min. | 6 min. | >20 min. |
| 8S | Cabosil M5, 1 | Blue | 4.5 min. | 6.5 min. | 6.5 min. |

Footnotes for Table 16a:
[1]Run numbers with an "A" contain stock catalyst solution C16A while run numbers with an "S" contain stock catalyst solution C16S.
[2]"Quso" = Quso WR-55. "Cabosil M5" = hydrophilic fumed silica available from Cabot Corp., Tuscola, IL. "Imsil" = Imsil A-25. "Vicron" = Vicron 45-3 calcium carbonate available from Pfizer, Inc., New York, N.Y. "Talc" = Beaverwhite 200 hydrous magnesium silicate available from Cyprus Industrial Minerals, Inc., Englewood, CO. "Alumina" = A208 hydrated aluminum oxide available from R. J. Marshall, Inc., Southfield, MI.

Notably, the inclusion of certain fillers appears to affect both the initial paste color and the bleach time. For fillers which affect color and bleach time, the effect can be reversed with Silwet L-77.

EXAMPLE 17

Cure-indicating putty catalyst and base impression materials were prepared by mixing the following ingredients in a 1 gallon Ross mixer:

TABLE 17a

| Ingredient | Catalyst (parts) | Base (parts) |
|---|---|---|
| LMWP | 5.80 | 5.00 |
| HMWP[1] | 13.60 | 11.70 |
| Pt Catalyst[2] | 0.60 | — |
| Crosslinker[3] | — | 3.10 |
| Mineral Oil[4] | 6.50 | 6.50 |
| VIcron 45-3 | 36.75 | 36.75 |
| Imseil A-25 | 36.75 | 36.75 |
| Silwet L-77 | — | 0.35 |
| DVTMDS | — | 0.0067 |
| Dye #2 | — | 0.006 |

Footnotes for Table 17a:
[1]"HMWP" = vinyl-terminated poly(dimethylsiloxane) with a viscosity of 60 PA s and molecular weight approximately 60,000 g/mol.
[2]From Preparatory Example 1a.
[3]"Crosslinker" = A methylhydrosiloxane-dimethylsiloxane copolymer with a viscosity between about 50 and 70 mPa · s and having approximately 0.13% active hydrogen ("XL2").
[4]"Mineral Oil" = Kaydol ™ white mineral oil, USP grade available from Witco Chemical Corp., Conneborn Div., Chicago, IL.

Catalyst and base putty impression material pastes were mixed together to give a cure-indicating formulation with T5=127 sec.; T90=190 sec.; and Bleach time=292 sec. at 27° C.

EXAMPLE 18

Preparation of a Silwet-free impression material. Impression material catalyst and base pastes were prepared by mixing the following ingredients:

TABLE 18a

| Ingredient | Catalyst, Parts | Base, Parts |
|---|---|---|
| VLMWP | 83.1 | 51.2 |
| Pt Catalyst[1] | 3.04 | — |
| Crosslinker[2] | — | 34.12 |
| DVTMDS | — | 0.07 |
| Vicron 45-3 | 107.5 | 108.5 |
| Quso WR-55 | 6.1 | 7.1 |
| Dye #2 | 0.014 | — |

Footnotes for Table 18a:
[1]From Preparatory Example 1a.
[2]"XL2".

Catalyst and base pastes were placed in separate barrels of a dual-barrel syringe and extruded through a static-mixing element. The material had a T5=129 sec.; T90=160 sec.; and Bleach time=240 sec. @27° C.

EXAMPLE 19

Preparation of size-reduced structural abrasive molds. Stock catalyst and base solutions were prepared for use in fabricating size-reduced molds by mixing the following:

TABLE 19a

| Ingredient | Catalyst (parts) | Base (parts) |
|---|---|---|
| LMWP | 1325 | 1010 |
| HMWP | 667 | 667 |
| Pt Catalyst[1] | 8 | — |
| Crosslinker[2] | — | 320 |
| DVTMDS | — | 3 |
| VMP Naphtha | 2000 | 2000 |

Footnotes for Table 19a:
[1]From Preparatory Example 1a
[2]"XL2"

Catalyst and base solutions were mixed and poured against a flat, structured die. The system was closed to prevent solvent evaporation. After three hours the material cured and a color change from blue to clear occurred over a period of about 15 min. At this point the cured sample was removed from the die and solvent was allowed to evaporate to form a size-reduced mold 50% of the original die volume.

EXAMPLE 20

A stock catalyst resin solution (C20) was prepared by mixing 190 parts VLMWP, 4.72 parts platinum catalyst from Preparatory Example 1a, and 3.30 parts Silwet L-77. A stock TABLE 20a

| Run # | Dye | Pigment | Initial Color of Composition | Final Color of Composition after curing |
|---|---|---|---|---|
| 1 | None | None | Off White | Off White |
| 2 | + | None | Blue | Off White |
| 3 | None | Pink | Pink | Pink |
| 4 | + | Pink | Purple | Pink |
| 5 | None | Yellow | Yellow | Yellow |
| 6 | + | Yellow | Green | Yellow |

TABLE 20b

| Run # | Initial L*A*B* Color (immed. after mixing) | Final L*A*B* Color (after curing) | Final Color Difference $(\Delta E^*)$[1] between sample having dye and control sample having no dye | Color difference $(\Delta E^*)$ between initial and final color |
|---|---|---|---|---|
| 1 | 70.00/2.01/6.68 | 70.04/1.91/6.88 | 0.71 | 0.23 |
| 2 | 63.03/−6.52/−4.67 | 69.94/1.36/6.44 | | 15.27 |
| 3 | 63.14/26.50/−0.65 | 63.11/26.31/−0.51 | 2.93 | 0.24 |
| 4 | 57.82/9.93/−9.80 | 62.80/23.63/−1.66 | | 16.70 |
| 5 | 71.66/−3.71/20.73 | 71.70/−3.66/20.68 | 1.97 | 0.08 |
| 6 | 63.02/−13.17/8.13 | 70.17/−4.36/19.65 | | 16.17 |

Footnotes for Tables 20a and 20b:
[1] "$\Delta E^*$" = $[(L_1^* - L_2^*)^2 + (A_1^* - A_2^*)^2 + (B_1^* - B_2^*)^2]^{1/2}$ where $L_1^*A_1^*B_1^*$ and $L_2^*A_2^*B_2^*$ are the colors of the samples being compared. As a general rule, colors which differ by less than about 3 $\Delta E^*$ units cannot be distinguished readily by the human eye.

base resin solution (B20) was prepared by mixing 193 parts VLMWP, 0.21 parts divinyltetramethyl disiloxane, 98.82 parts XL2, and 4.95 parts Silwet L-77. A stock dye paste (DP20) was prepared from 83 parts VLMWP, 12 parts Quso WR-55 and 5 parts dye #2 using a three-roll mill. Impression material catalyst pastes were prepared by mixing 90 parts C20, 10 parts Quso WR-55, 100 parts Imsil A-25 and optionally 0.30 parts DP20. Impression material base pastes were prepared by mixing 90 parts B20, 10 parts Quso WR-55, 100 parts Imsil A-25 and optionally 1.4 parts of pink or yellow fluorescent pigment (Aurora Pink AX-11 or Saturn Yellow AX-17, available from DAY-GLO Color Corp., Cleveland, Ohio). Curing impression pastes were prepared by placing catalyst and base pastes into separate barrels of a dual barrel syringe and extruding through a static mixer.

Initial and final colors were determined using a color computer/spectrophotometer instrument (a Milton Roy Diano Match Scan II double beam spectrophotometer with a diffuse lighting source). Measurements were taken using a sample area view of 25 mm diameter and with specular reflection included. The surface colors of 3 mm thick slabs of impression pastes were measured and reported in the CIE L*A*B* color system (as described in "Principles of Color Technology", Billmeyer & Saltzman, Second Edition, 1981). This system is based on a 3-dimensional color space with the positive X-axis representing red, the negative X-axis representing green, the positive Y-axis representing yellow, the negative Y-axis representing blue, and the Z-axis going from zero (black) to 100 (white) with the origin at 50.

This experiment illustrates that complete bleaching of the dye occurs as the compositions react and cure. This is illustrated by comparison of the final colors of the samples with dye #2 and without dye #2. For example, the difference between the final (i.e., post cure) colors of Run #1 and Run #2 is about 0.71 $\Delta E^*$ units. This minor difference in color would be well below that level which could be detected by the human eye. Similarly, comparing Runs 3 and 4 and Runs 5 and 6 yields $\Delta E^*$ values below the level which is detectable easily by the human eye.

This experiment also illustrates that readily-observable color changes occur in the samples containing cure indicating dye. Runs 1, 3 and 5 do not contain any cure-indicating dye and do not change color as a result of the curing process ($\Delta E^*$ values for these runs are 0.23, 0.24, and 0.08, respectively). Runs 2, 4 and 6 each contain a cure-indicating dye. Notably, these runs also exhibit large color changes (15.27, 16.70, and 16.17, respectively) as the samples are cured. For dental impression materials (and similar compositions which are monitored by the human eye) the amount of color change exhibited by the dye need only be that amount of change that can be observed by the human eye. Preferably, the impression material exhibits a color change upon curing of at least 5 $\Delta E^*$ units when tested as described above. More preferably, the impression material exhibits a color change upon curing of at least 10 $\Delta E^*$ units. Most preferably, the impression material exhibits a color change upon curing of at least 15 $\Delta E^*$ units.

TABLE 20c

Figure 1:
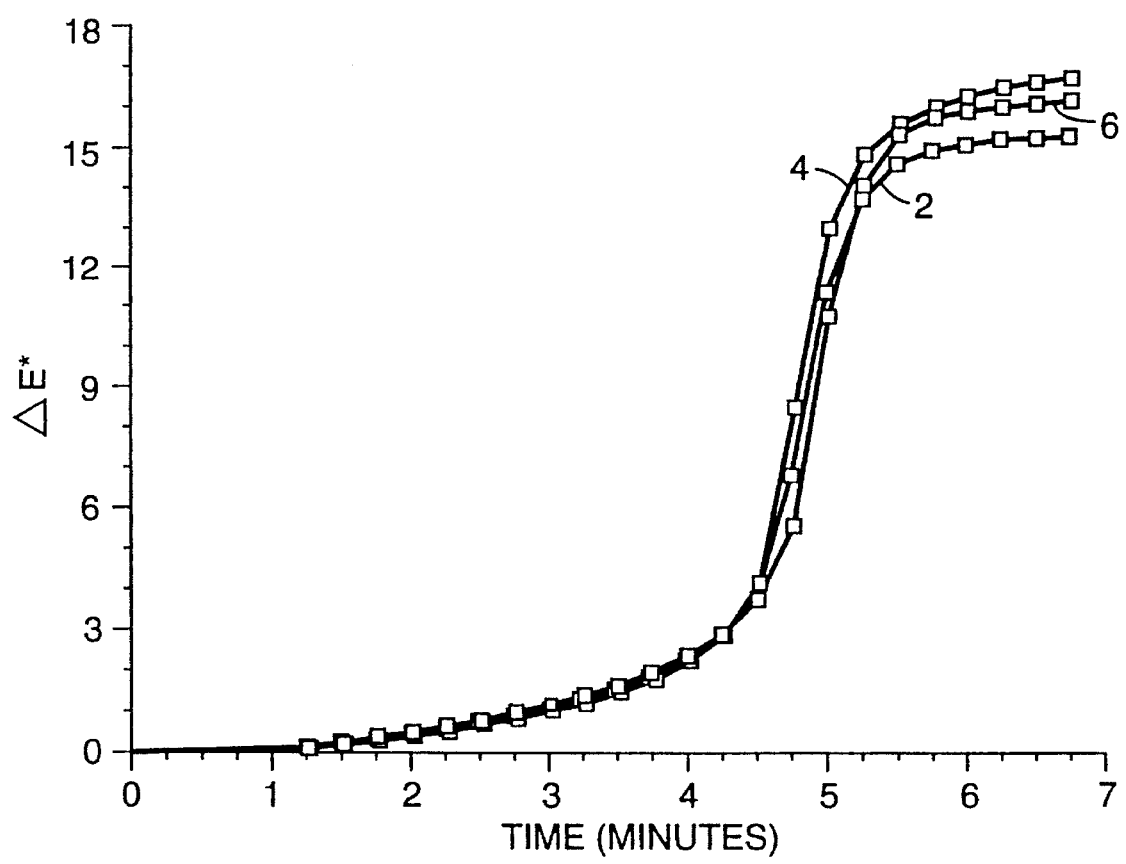
FIG. 1 illustrates $\Delta E^*$ as a function of curing time graphically for runs 2, 4, and 6. To generate these plots the samples were mixed and placed in the spectrophotometer. An initial color scan was obtained (within less than 1.25 minutes) and used as the reference color. Additional scans were taken as the material cured and were compared to the initial scan. The difference in color ($\Delta E^*$) was computed for each additional scan and plotted. Table 20c contains the raw data for these scans. As can be seen in FIG. 1 the color change was very pronounced for these samples (initial color→final color) and occurred over a very short time period. Notably, the color change for each sample coincided with the gel point of the material. Thus, the pronounced, rapid color change was a very good indicator of the set time of the material. T90 for Runs 2, 4, and 6 was 5.28, 5.37 and 5.20 minutes, respectively, the time at which the color has changed to within 3 $\Delta E^*$ units of the final color. Additionally, the time at which the initial color changes 3 $\Delta E^*$ units from the initial color corresponds approximately with the T5 for Runs 2, 4, and 6 of 3.8, 3.9, and 3.9 minutes, respectively. This demonstrates the effectiveness of indicating both the working time and setting time in a single formulation.

| Time (Minutes) | Run 2 ($\Delta E^*$) | Run 4 ($\Delta E^*$) | Run 6 ($\Delta E^*$) |
|---|---|---|---|
| 1.25 | 0.13 | 0.09 | 0.14 |
| 1.50 | 0.24 | 0.19 | 0.27 |
| 1.75 | 0.37 | 0.30 | 0.41 |
| 2.00 | 0.50 | 0.42 | 0.55 |
| 2.25 | 0.64 | 0.55 | 0.71 |
| 2.50 | 0.79 | 0.69 | 0.86 |
| 2.75 | 0.94 | 0.85 | 1.05 |
| 3.00 | 1.12 | 1.03 | 1.23 |
| 3.25 | 1.32 | 1.22 | 1.45 |
| 3.50 | 1.57 | 1.48 | 1.71 |
| 3.75 | 1.86 | 1.79 | 2.02 |
| 4.00 | 2.25 | 2.21 | 2.41 |
| 4.25 | 2.85 | 2.87 | 2.96 |
| 4.50 | 3.83 | 4.12 | 3.79 |
| 4.75 | 6.83 | 8.48 | 5.59 |
| 5.00 | 11.37 | 13.03 | 10.81 |
| 5.25 | 13.76 | 14.86 | 14.15 |
| 5.50 | 14.62 | 15.59 | 15.36 |
| 5.75 | 14.95 | 16.00 | 15.77 |
| 6.00 | 15.12 | 16.25 | 15.95 |
| 6.25 | 15.21 | 16.45 | 16.05 |
| 6.50 | 15.26 | 16.59 | 16.12 |
| 6.75 | 15.32 | 16.70 | 16.18 |

EXAMPLE 21

A stock catalyst resin solution (C21) was prepared by mixing 2928 parts LMWP with 72 parts of the catalyst from Preparatory Example 1a. Cure-indicating catalyst pastes were prepared by mixing 295 parts C21, 4.5 parts of surfactant or wetting agent according to Table 21, 30 parts Quso WR-55, 300 parts Imsil A-25, and 0.96 parts stock solution DP20 in a double planetary Ross mixer. A base impression paste (B21) was prepared by mixing 465 parts VLMWP, 195 parts XL2, 1.0 parts DVTMDS, 60 parts Aerosil R976, and 780 parts Imsil A-25 in a double planetary Ross mixer. The catalyst and base impression pastes were placed in separate barrels of a dual barrel syringe, extruded through a static-mixing tip and checked visually for color change upon curing. Results are given in Table 21.

TABLE 21

| Run | Wetting Agent | Initial Color[1] | Cured Color |
|---|---|---|---|
| 1 | none | Grey | Grey |
| 2 | Neodol ® 1-9[2] | Blue | Off White |

TABLE 21-continued

| Run | Wetting Agent | Initial Color[1] | Cured Color |
|---|---|---|---|
| 3 | Carbowax ®[3] | Blue | Off White |
| 4 | Triton X102[4] | Blue | Off White |
| 5 | Fluorad FC170C[5] | Blue | Off White |
| 6 | Fluorad FC430[5] | Blue | Off White |
| 7 | Dibasic ester[6] | Blue | Off White |

[1]"Initial Color" is the color the catalyst impression paste.
[2]Available from Shell Chemical Co., Houston, TX.
[3]Sentry ® polyethylene glycol 400, available from Union Carbide Chemicals and Plastics Co., Inc., Danbury, CT.
[4]Available from Rohm and Haas Co., Philadelphia, PA.
[5]Available from 3M Co., St. Paul, MN.
[6]A mixture of dimethyl glutarate, dimethyl adipate, and dimethyl succinate and available from E. I. duPont deNemours, Wilmington, DE. This impression material paste was prepared using a Semkit 388 mixer as previously described.

The above example illustrates that a variety of surfactants or wetting agents can be employed in filled compositions of the present invention. The filled composition of Run #1 did not exhibit an initial "blue" color as did Runs 2–7 which contained a wetting agent. The compositions with a wetting agent all exhibited a readily observable color change upon curing.

EXAMPLE 22

Reduction Potential and Spectroscopic Data of Various Dyes

Reduction potentials by Cyclic Voltammetry: For a discussion of the underlying theory of potentiometry in organic solvents, the preferred method of referencing voltage measurements by means of ferricenium and cobalticenium salts, and the use of Cyclic Voltammetry for making such measurements, we incorporate herein by reference "The Chemistry of Nonaqueous Solvents", Volumes I (1966) and IV (1976), edited by J. J. Lagowski, Academic Press, NY, and specifically the chapter in Volume I entitled "Electrode Potentials in Non-Aqueous Solvents" by H. Strehlow, notably page 159, and the chapter in Volume IV entitled "Redox Systems in Nonaqueous Solvents" by M. Rumeau, notably pages 90 and 96.

Based on the foregoing, solutions were made having approximately 0.0100 molar dye in a 0.100 molar solution of tetrabutylammonium tetrafluoroborate in dry 99% acetonitrile—1% trifluoroethanol (by volume). The reduction potentials were measured with respect to the saturated calomel electrode at a scan rate of 20 V per second toward more negative values, and are reported as the peak potential.

Conversion to other electrode/potential scales may be carried out by making use of the values measured for the reduction potentials of cobalticenium and ferricenium salts, as reported in Table 22. This procedure also is applicable when correcting for reasonable modifications in the solvent system necessitated by experimental factors such as solubility. Reduction potentials thus obtained are reported in Table 22. Preferred cure-indicating dyes, for use in the present invention, have a reduction potential greater than −0.80. More preferred cure-indicating dyes have a reduction potential between 0 and −0.80.

Spectroscopic measurements: The dye solutions prepared for Cyclic voltammetry were diluted to 0.000050 molar in dry spectro-grade acetonitrile, and their spectra were measured from 200 to 800 nm in 10 mm silica cells, by means of a Perkin-Elmer No. 330 spectrophotometer. In the event that the maximal absorbance exceeded 3.0, a further fivefold dilution to 0.000010 molar was performed. In Table 22 is listed the wavelengths of maximal absorption ($\lambda_{max}$) in nanometers (nm) and the wavelengths (short and long, respectively) at which the absorbance had fallen to one-half its maximal value. The latter serve to indicate the peak breadth and shape. The "Molar Extinction Coefficient", also termed "Molar Absorbance", ($\epsilon$), is the measured absorbance corrected for concentration of the dye. In cases of commercial dyes for which the structures have not been disclosed, a nominal molecular weight of 475 was used to calculate molarities. In some cases, notably Sample No. 55, lack of purity means that the true molar extinction coefficients will be proportionately larger than the reported values. As is conventional in spectrophotometry, the common logarithms of the molar extinction coefficients is also reported in Table 22.

TABLE 22

| Sample No. | C.V. Reduction Potential | Wavelength of Maximal Visible Adsorption (nm)$\lambda_{max}$ | Molar extinction Coefficient $\epsilon$ | Wavelengths of Half-maximal Visible Absorption, (nm) $\lambda'_{1/2}$ | $\lambda''_{1/2}$ | Log $\epsilon$ |
|---|---|---|---|---|---|---|
| 2 | −0.73 | 645 | 31,300 | 587 | 703 | 4.50 |
| 5 | −1.01 | 607 | 14,700 | 536 | 667 | 4.17 |
| 6 | −0.98 | 602 | 15,200 | 535 | 663 | 4.18 |
| 11 | −0.97 | 532 | 9,200 | 464 | 593 | 3.97 |
| 14 | −0.5 | 675 | 26,600 | 617 | 731 | 4.42 |
| 15 | −0.55 | 687 | 32,000 | 630 | 740 | 4.51 |
| 16 | −0.95 | 612 | 16,800 | 544 | 673 | 4.23 |
| 17 | −0.87 | 660 | 3,800 | 591 | 724 | 3.57 |
| 19 | −0.96 | 476 | 2,400 | — | 580 | 3.37 |
| 21 | −0.29 | 525 | 1,700 | — | 641 | 3.22 |
| 23 | −0.9 | 547 | 1,800 | — | 621 | 3.26 |
| 34 | −0.99 | 374 | 3,600 | 338 | 418 | 3.56 |
| 43 | −0.24 | 488 | 15,200 | 437 | 525 | 4.18 |
| 46 | −0.86 | 479 | 27,000 | 438 | 512 | 4.43 |
| 48 | −0.61 | 498 | 26,700 | 459 | 533 | 4.43 |
| 51 | −1.26 | 588 | 178,200 | 570 | 605 | 5.25 |
| 52 | −0.49 | 638 | 113,900 | 593 | 667 | 5.06 |
| 53 | −0.78 | 532 | 125,800 | 498 | 552 | 5.10 |
| 54 | −0.67 | 560 | 54,800 | 509 | 586 | 4.74 |
| 55 | — | 661 | >5,000 | 600 | 703 | >3.7 |
| 56 | −0.71 | 542 | 114,200 | 508 | 562 | 5.06 |
| 58 | −0.61 | 627 | 73,700 | 583 | 655 | 4.87 |
| 59 | −0.63 | 543 | 68,900 | 509 | 566 | 4.84 |
| 60 | −0.97 | 527 | 1,900 | — | 621 | 3.27 |
| 77 | −0.50 | 639 | 176,000 | 609 | 663 | 5.25 |
| A | −1.20 | 391 | 16,100 | 331 | 443 | 4.21 |
| B | −1.04 | 472 | 13,800 | 375 | 515 | 4.14 |
| D | −1.09 | 483 | 15,600 | 383 | 530 | 4.19 |
| E | −0.93, −1.35 | 514 | 15,300 | 432 | 562 | 4.19 |
| F | −0.89, −1.4 | 501 | 21,100 | 434 | 545 | 4.33 |
| G | −0.88, −1.23 | 508 | 25,300 | 449 | 553 | 4.40 |
| I | −1.15 | 593, 600 | 11,900, 13,900 | 555 | 658 | 4.08, 4.14 |
| K | −1.19 | 590, 636 | 15,800, 18,600 | 555 | 653 | 4.20, 4.27 |
| L | −0.82 | 581 | 7,000 | 509 | 635 | 3.85 |
| Cobalticenium Hexafluorophosphate | −0.939 | | | | | |

TABLE 22-continued

| Sample No. | C.V. Reduction Potential | Wavelength of Maximal Visible Adsorption (nm)$\lambda_{max}$ | Molar extinction Coefficient $\epsilon$ | Wavelengths of Half-maximal Visible Absorption, (nm) $\lambda'_{1/2}$ | $\lambda''_{1/2}$ | Log $\epsilon$ |
|---|---|---|---|---|---|---|
| (Ref) Ferricenium Hexafluorophosphate (Ref) | +0.453 | | | | | |

EXAMPLE 23

A stock catalyst paste was prepared by combining in a Ross mixer 33 parts platinum catalyst (Preparatory Example 1a), 1449 parts vinyl-terminated polydimethylsiloxane having a viscosity of 2.0 Pa-s "LMWP"), and 180 parts Quso WR-55 and mixing 10 minutes at 30 rpm. 1320 parts of Imsil A-25 was added and mixed 70 minutes at 30 rpm under vacuum. 18 parts of Silwet L-77 was added and mixed 35 minutes at 30 rpm under vacuum to make catalyst paste C23.

Base pastes were prepared by adding the indicated number of parts of dye to 3.3 parts Silwet L-77, see Table 23. The Silwet/dye mixture was added to a mixture of 136 parts LMWP, 54 parts of organohydrogenpolysiloxane, XL2, and 0.17 parts 1,3-divinyl-1,1,3,3-tetramethyldisiloxne and shaken vigorously. 180 parts of this mixture and 22.5 parts of Quso WR-55 were added to a Ross mixer and mixed for 10 minutes at 40 rpm. 173 parts of Imsil A-25 was added and mixed 70 minutes at 40 rpm under vacuum to form blue base pastes B23. These catalyst and base pastes were placed in separate barrels of a dual barrel syringe and evaluated for bleaching and curing properties.

TABLE 23

| Run | Dye | Dye, parts | Cure Indicator Result |
|---|---|---|---|
| 1 | CMDI-TMHE | 0.042 | bleaches at cure point |
| 2 | CMDDI | 0.038 | bleaches at cure point |
| 3 | CMDI-CI | 0.090 | bleaches at cure point |
| 4 | CDHI | 0.080 | bleaches at cure point |
| 5 | CMDI-OH | 0.024 | not soluble in formulation |
| 6 | CDI | 0.022 | bleaches at cure point |
| 7 | CMDI-TMSether | 0.043 | bleaches at cure point |
| 8 | TC-Bu2 | 0.040 | bleaches before cure point |
| 9 | TC-Et3 | 0.040 | bleaches before cure point |
| 10 | S,N-compound | 0.040 | not soluble in formulation |
| 11 | CMDI-PIV* | 0.040 | bleaches at cure point |

*Silbond ® 3000MST-M filler (available from Quarzwerke GmbH, Freschen, Germany) was substituted for Imsil in the base paste for run #11.

Compounds 1 and 3–11 were tested according to the procedure of Example 4. They bleached according to the description defined in Example 4.

The chemical structures of these dyes are as follows:

CMDI-TMHE
Example 23 #1
2-Chloro-4-[[2-methyl-4-(N-ethyl-N-(2-(3,5,5-trimethylhexanoxy)ethyl)amino)phenyl]imino]-2,5-cyclohexadien-1-one

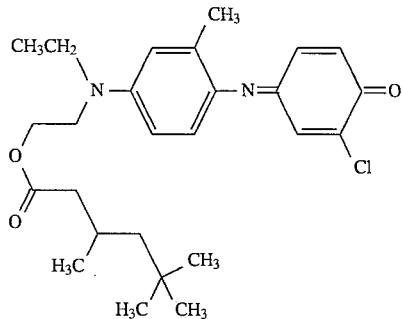

CMDI-TMSether
Example 23 #7
2-Chloro-4-[[2-methyl-4-(N-ethyl-N-(3,5-dioxa-7-(trimethylsilyl)heptyl)amino)phenyl]imino]-2,5-cyclohexandien-1-one

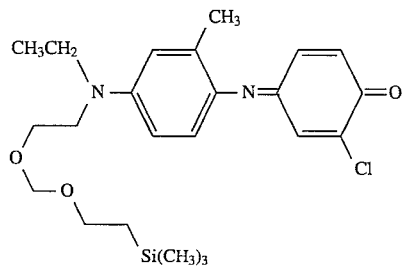

CMDDI
Example 23 #2
2-Chloro-4-[[4-(N-dodecyl-N-methylamino)phenyl]imino]-2,5-cyclohexandien-1-one

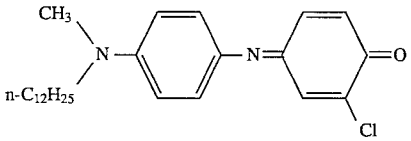

CDHI
Example 23 #4
2-Chloro-4-[[4-(dihexylamino)phenyl]imino]-2,5-cyclohexandien-1-one

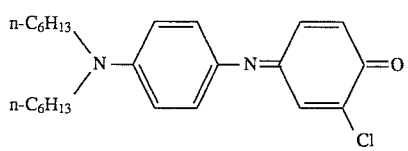

CMDI-PIV
Example 23 #11
2-Chloro-4-[[2-methyl-4-(N-ethyl-N-(2-dimethylproprionoxy)ethyl)amino)phenyl]imino]-2,5-cyclohexadien-1-one

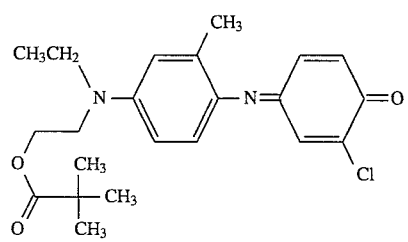

-continued
CMDI-OH
Example 23 #5
2-Chloro-4-[[2-methyl-4-(N-ethyl-N-(2-hydroxyethyl)amino)phenyl]imino]-2,5-cyclohexadien-1-one

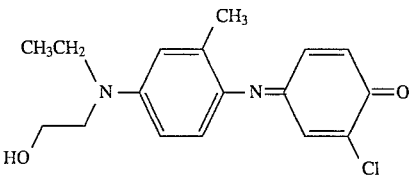

CMDI-Cl
Example 23 #3
2-Chloro-4-[[2-methyl-4-(N-ethyl-N-(2-chloroethyl)amino)phenyl]imino]-2,5-cyclohexadien-1-one

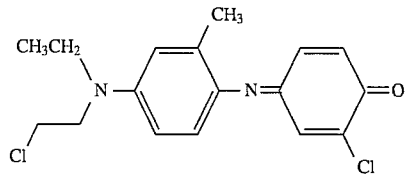

CDI
Example 23 #6
2-Chloro-4-[[4-(diethylamino)phenyl]imino]-2,5-cyclohexadien-1-one

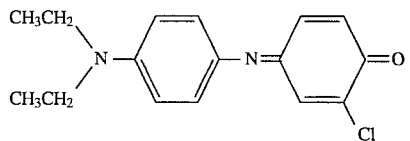

EXAMPLE 24

Preparation of 2-Phenyl-1,1,3-tricyanopropylene

A mixture of 250 grams (1.722 mol, 1 eq) of benzoylacetonitrile, 284 grams (270 mL, 4.306 mol, 2.5 eq) of malononitrile and 138 grams (1.784 mol, 1.04 eq) of ammonium acetate in 2500 mL of ethanol was heated to reflux for 1.5 hours and then cooled to room temperature. To this mixture was added 190 mL of 12M hydrochloric acid dropwise with cooling (ice/water bath). The mixture was placed in a separate flask and a solid formed. To this mixture was added 3300 mL of water with stirring. The solid was collected and washed with 2 liters of water and stirred with 1200 mL of ethanol to give 203.3 grams (61% yield) of product.

EXAMPLE 25

Preparation of 3-[[4-(diethylamino)phenyl]imino]-2-phenyl-1-propene-1,1,3-tricarbonitrile A solution of 15.0 grams (0.0776 mol 1 eq) of 2-Phenyl-1,1,3-tricyanopropylene in 75 mL of ethanol was prepared by heating to approximately 65° C. To this was added, dropwise, a solution of 13.8 grams (0.0776 mol 1 eq) of N,N-diethyl-4-nitrosoaniline in 450 mL of ethanol at such a rate that the temperature did not go below 60° C. and then the mixture was stirred at 60° C. for 30 minutes. After the addition, the reaction was cooled to room temperature overnight and the precipitate was collected, washed with ethanol and air dried to give 5.74 grams (21% yield) of product, mp 212°–215° C. (dec).

The above procedure was used for the preparation of 3-[[4-dibutylamino)phenyl]imino]-2-phenyl-1-propene-1,1,3-tricarbonitrile using N,N-dibutyl-4-nitrosoaniline in place of N,N-diethyl-4-nitrosoaniline.

EXAMPLE 26

4[(3-methyl-2(3H)-benzothiazolyidene)methyl]-1,2-naphthoquinone

A solution of 4.35 grams (0.0776 mol, 4.91 eq) of potassium hydroxide was dissolved in 30 mL of water and added to a solution of 4.35 grams (0.0158 mol, 1 eq) of 2,3-dimethylbenzothiazolium methyl sulfate in 30 mL of water. The reaction mixture was stirred with 50 mL of benzene for 15 minutes. This mixture was added to a mixture of 5.0 grams (0.0316 mol, 2 eq) of 1,2-naphthoquinone in 50 mL of benzene and the resulting mixture was stirred for 1.5 hours at room temperature. The solid was collected by filtration and washed with water, hot ethanol and ether.

The solid was washed with refluxing ethanol and filtered hot to remove a yellow solid. The solid was washed with 50 mL of hot benzene and filtered hot. The residue was collected and air dried to give the product.

Compounds of examples 23, runs 2, 4, 5, and 6 were prepared according to the procedure for Preparatory Example 3, using the appropriately substituted phenylene diamine starting material. Additional compounds may be synthesized using techniques and starting materials that will be readily apparent to the ordinary synthetic chemist. For example, further substituents may be provided by reaction with the hydroxyl functionality of Example 23, run 5.

Various modifications and alterations of this invention will be apparent to those skilled in the art without departing from the scope and spirit of this invention, and it should be understood that this invention is not limited to the illustrative embodiments set forth herein.

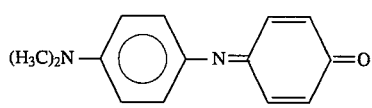 (Dye #1)

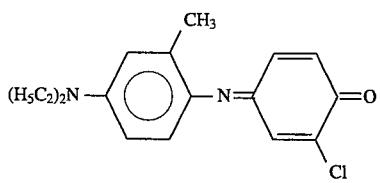 (Dye #2)

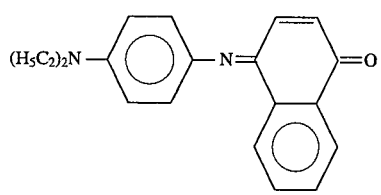 (Dye #3)

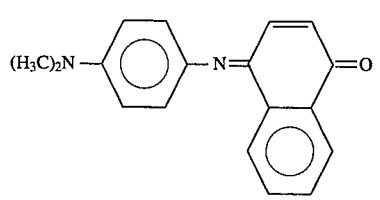 (Dye #4)

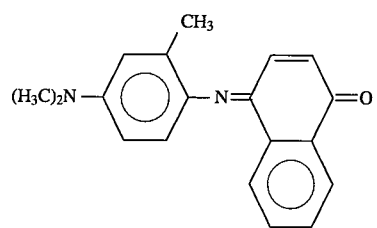 (Dye #5)

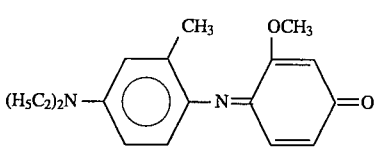 (Dye #6)

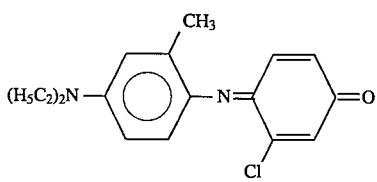 (Dye #7)

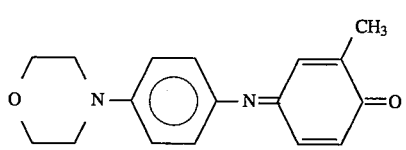 (Dye #8)

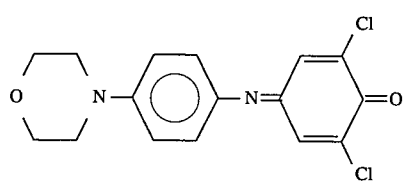 (Dye #10)

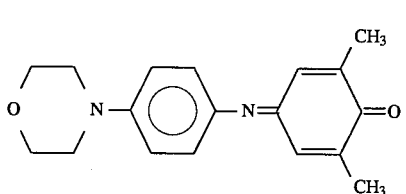 (Dye #11)

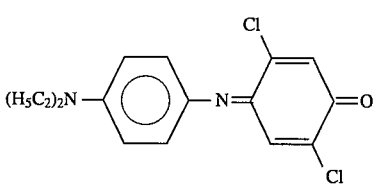 (Dye #12)

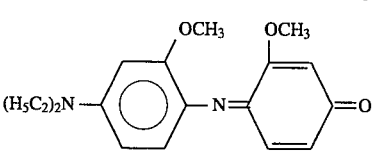 (Dye #13)

-continued
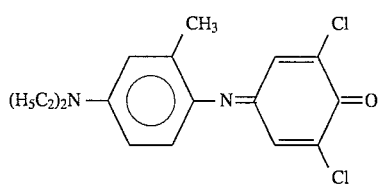
(Dye #14)
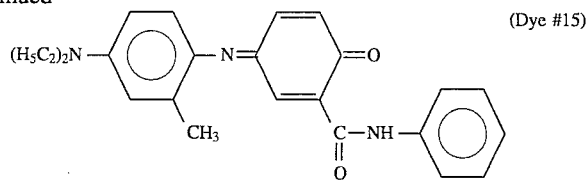
(Dye #15)
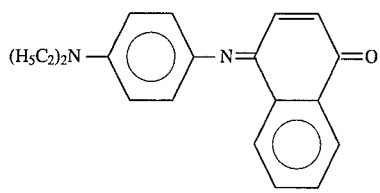
(Dye #16)
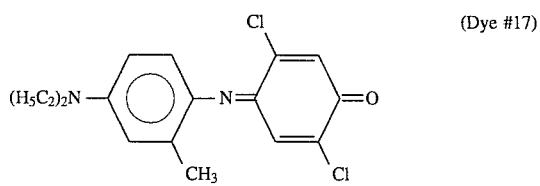
(Dye #17)
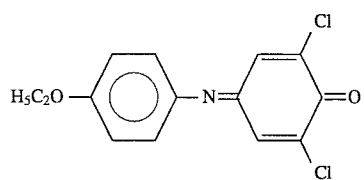
(Dye #18)
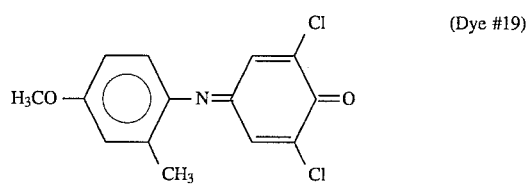
(Dye #19)
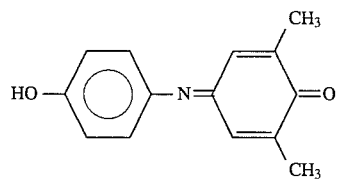
(Dye #20)
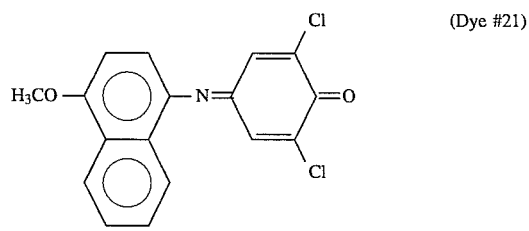
(Dye #21)
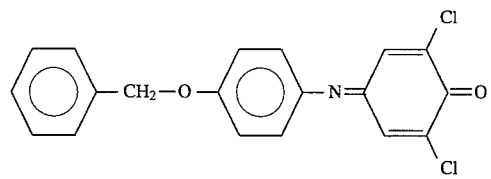
(Dye #22)
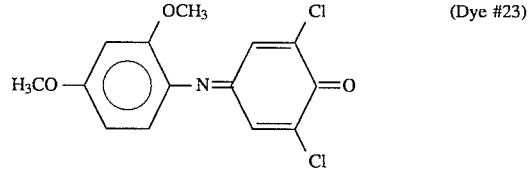
(Dye #23)
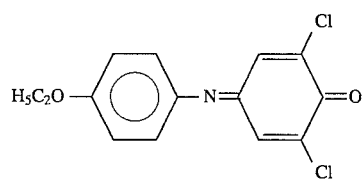
(Dye #24)
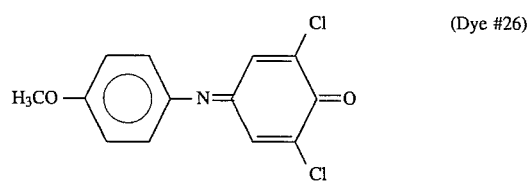
(Dye #26)
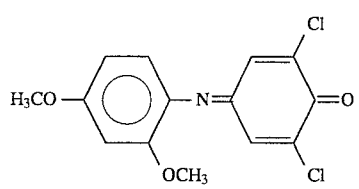
(Dye #27)
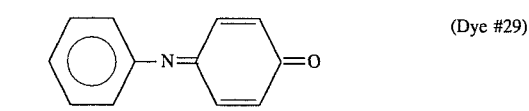
(Dye #29)
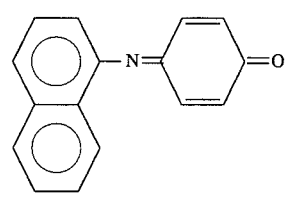
(Dye #30)
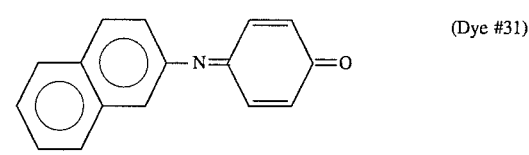
(Dye #31)

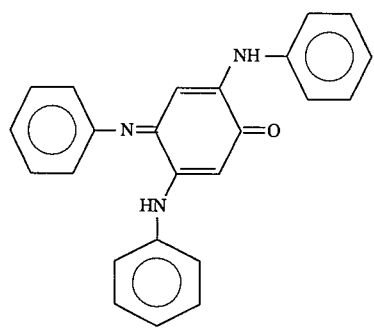
(Dye #34)
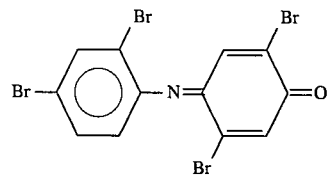
(Dye #37)
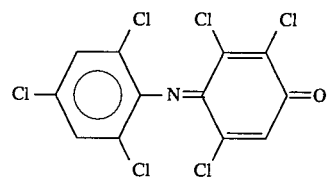
(Dye #39)
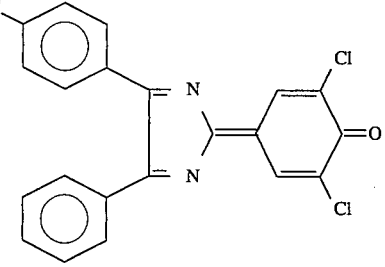
(Dye #40)
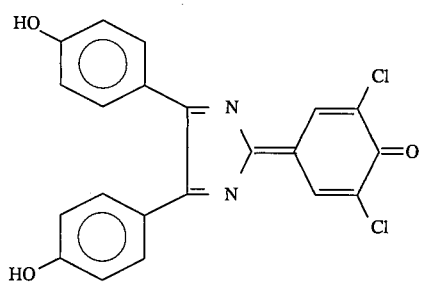
(Dye #41)
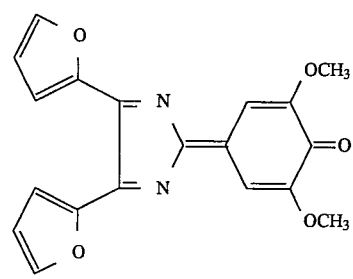
(Dye #42)
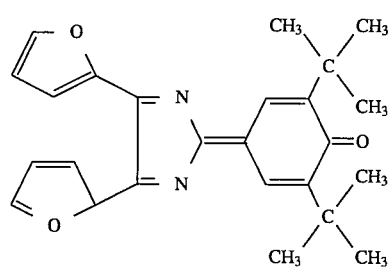
(Dye #43)
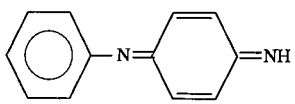
(Dye #44)
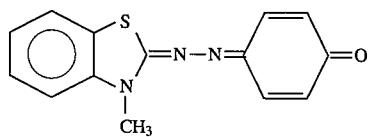
(Dye #46)
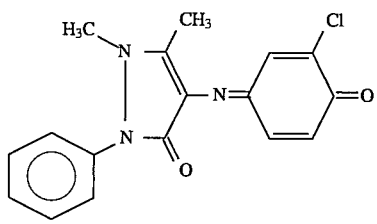
(Dye #47)
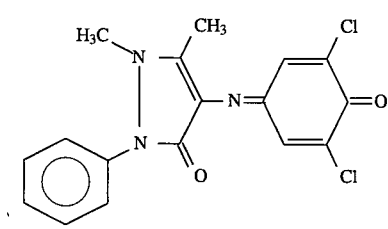
(Dye #48)
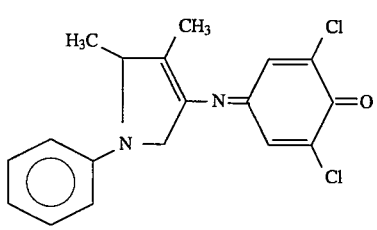
(Dye #49)

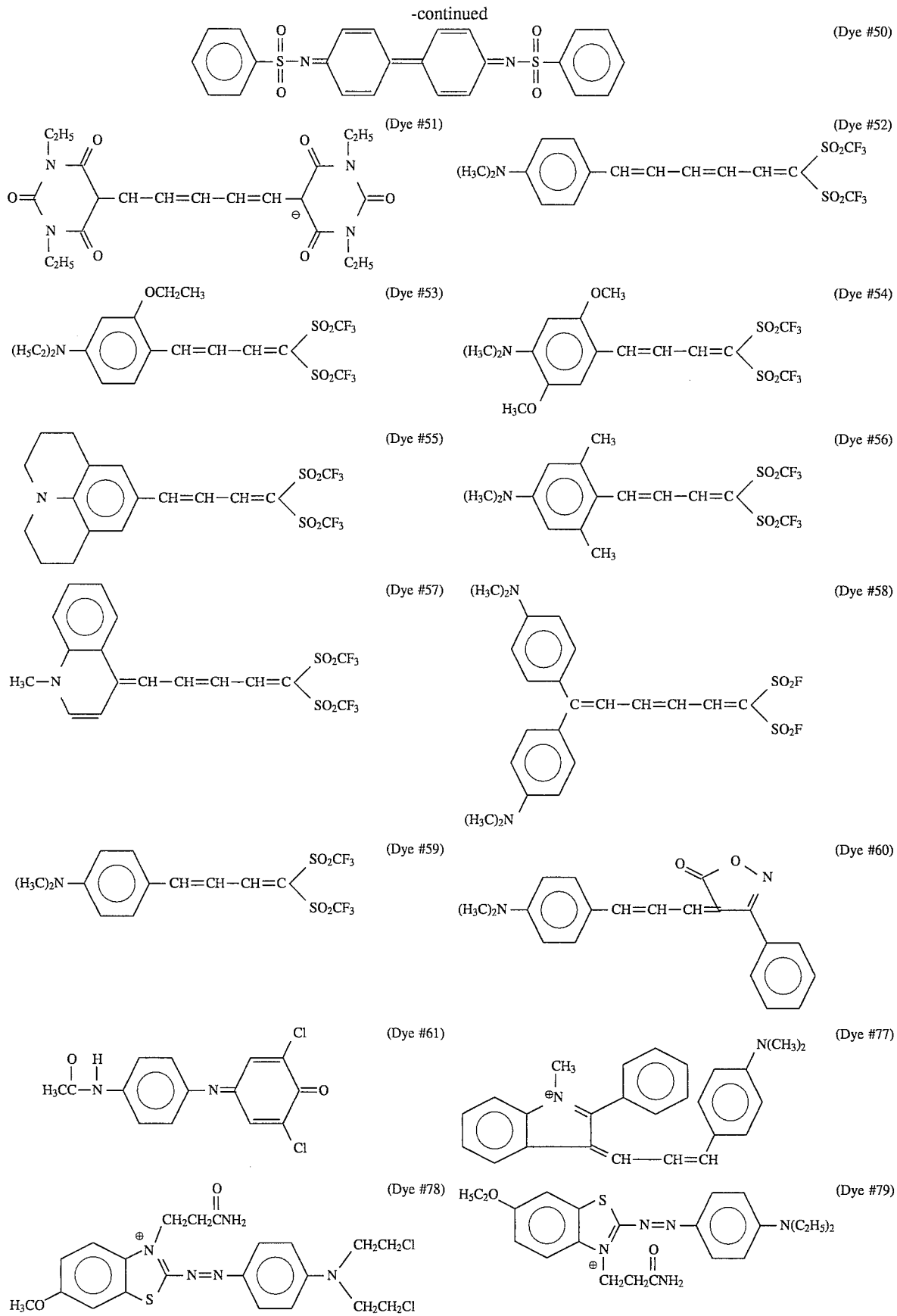

-continued
(Dye #80)
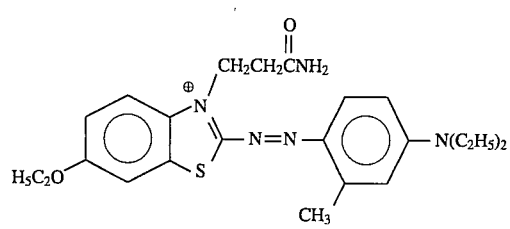
(Dye #85)
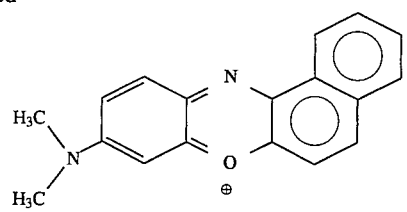
(Dye #86)
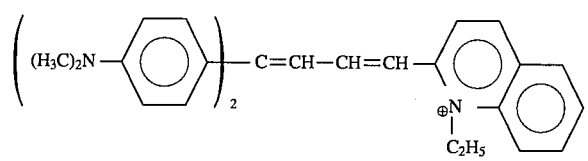
(Dye #87)
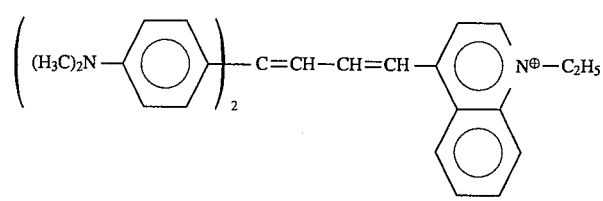
(Dye #88)
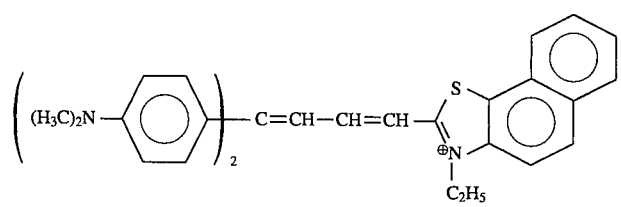
(Dye #89)
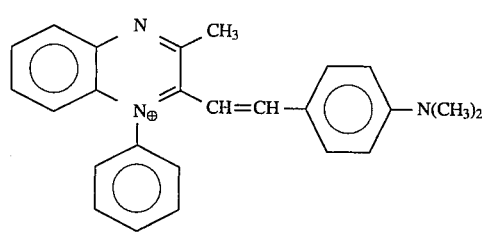
(Dye #90)
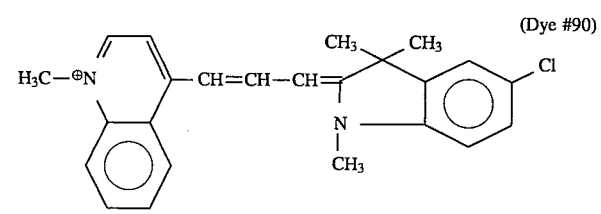
(Dye #91)
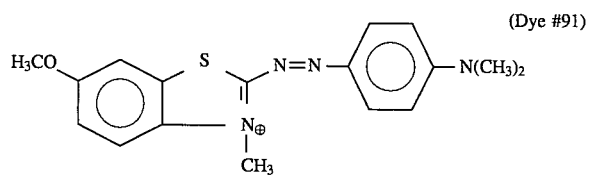
(Dye #92)
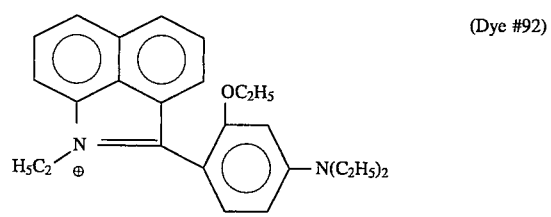
(Dye #93)
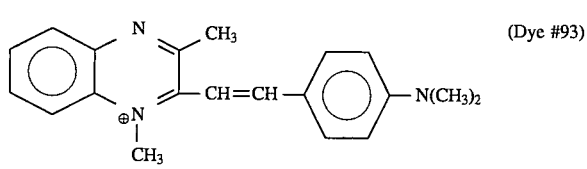
(Dye #94)
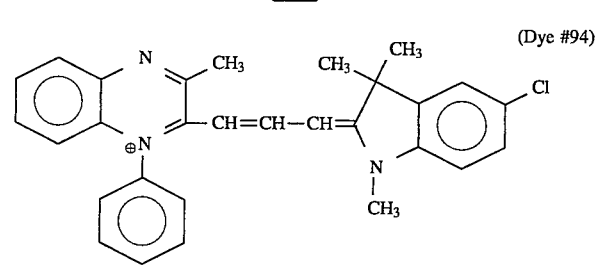
(Dye #96)
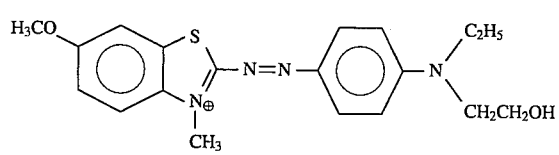

-continued
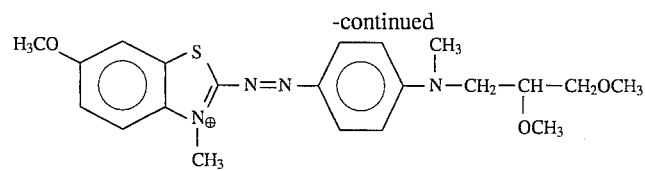
(Dye #97)
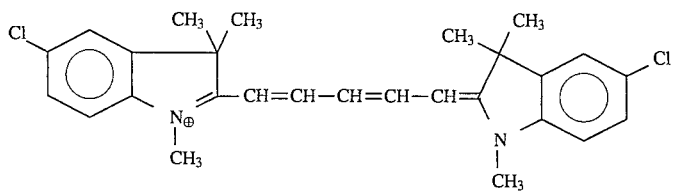
(Dye #100)
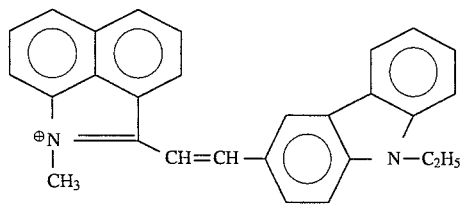
(Dye #102)
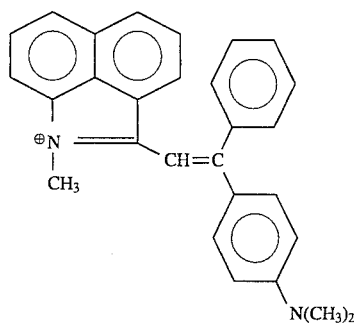
(Dye #104)
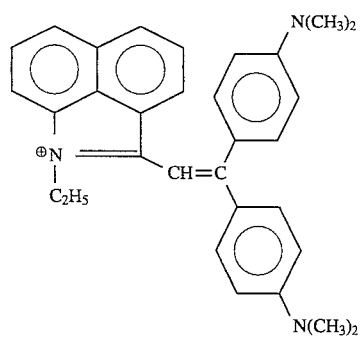
(Dye #105)
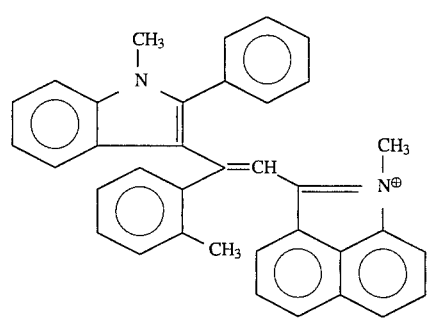
(Dye #107)
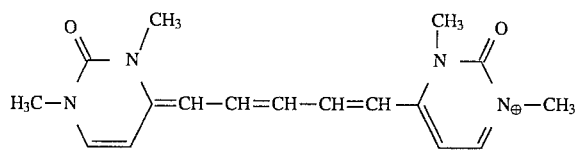
(Dye #108)
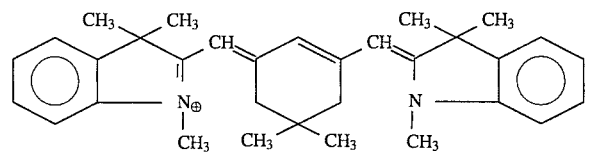
(Dye #109)
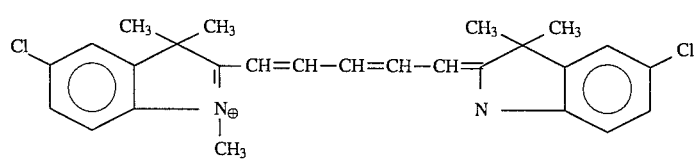
(Dye #110)
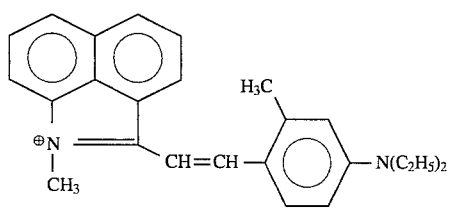
(Dye #111)
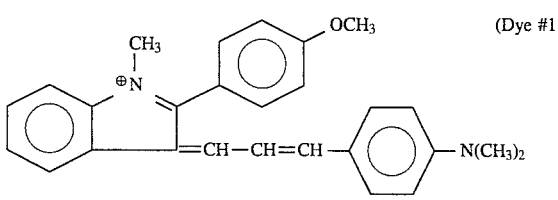
(Dye #112)

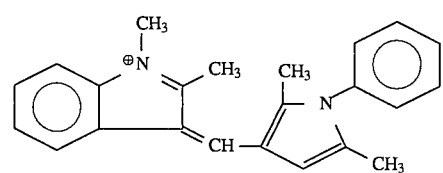 (Dye #113)

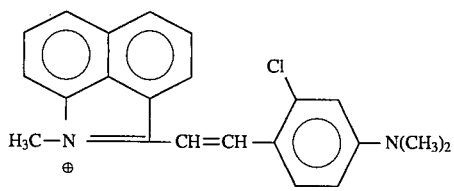 (Dye #115)

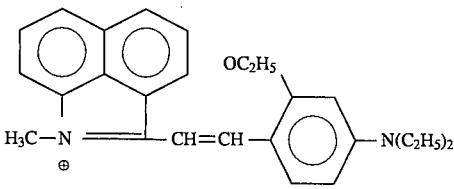 (Dye #122)

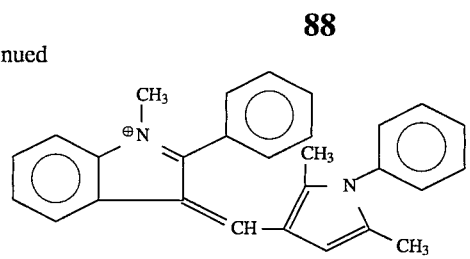 (Dye #114)

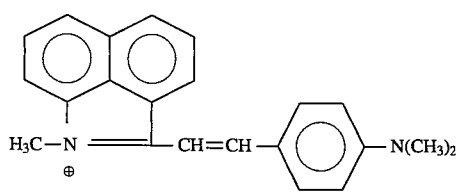 (Dye #121)

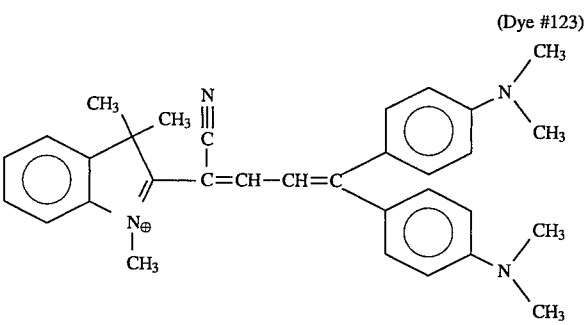 (Dye #123)

What is claimed is:

1. A dental impression material, comprising:

a curable silicone polymer containing at least two functional groups capable of reacting with a SiH group in the presence of a hydrosilation catalyst;

a crosslinker compound containing at least two SiH groups;

a catalyst capable of catalyzing a hydrosilation reaction; and one or more cure-indicating dyes, wherein, in a dye evaluation test, said dye exhibits a color change within about 10 minutes at 25° C. when 500 μg of said dye, 500 μl of dichloromethane, 100 μl of pentamethyldisiloxane and 10 μl of a hydrosilation catalyst solution having between about 2 and 3 weight percent platinum are mixed together, wherein said dye is represented by the formula

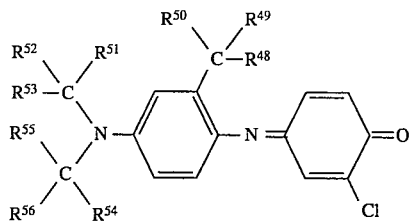

wherein each of $R^{48}$, $R^{49}$, and $R^{50}$, is independently selected from the group consisting of: hydrogen, halogen and an acyclic, alicyclic or aromatic hydrocarbyl group optionally interrupted with one or more heteroatoms, each of $R^{51}$, $R^{52}$, $R^{53}$, $R^{54}$, $R^{55}$, and $R^{56}$ is independently selected from the group consisting of hydrogen and an acyclic, alicyclic or aromatic hydrocarbyl group optionally interrupted with one or more heteroatoms, and optionally, any two of $R^{51}$, $R^{52}$, $R^{53}$, $R^{54}$, $R^{55}$, and $R^{56}$ may together form an alicyclic or aromatic ring.

2. The composition of claim 1, wherein each of $R^{48}$, $R^{49}$, and $R^{50}$ is independently selected from the group consisting of hydrogen, alkyl and halogen; and each of $R^{51}$, $R^{52}$, $R^{53}$, $R^{54}$, $R^{55}$, and $R^{56}$ is independently selected from the group consisting of hydrogen and alkyl that is optionally substituted by one or more cyano, alkoxy, hydroxy, alkylsiloxy, alkylsilyl, acyl, aryl, halo, arylsiloxy, arylsilyl, amino, and mono or dialkyl amino groups.

3. The composition of claim 1, wherein at least one of $R^{51}$, $R^{52}$, $R^{53}$, $R^{54}$, $R^{55}$, and $R^{56}$ is selected from the group consisting of —$CH_2OSi(CH_3)_2 C(CH_3)_3$

—$CH_2OC(O)CH_2CH(CH_3)CH_2C(CH_3)_3$

—$CH_2OC(O)C(CH_3)_3$

—$CH_2OCH_2OCH_2CH_2Si(CH_3)_3$

—$CH_2Cl$

—$CH_2OC(O)NHCH_2CH_2CH_2CH_3$, and

—$CH_2OC(O)NHCH_2CH_2CH_2Si(OCH_2CH_3)_3$.

4. A dental impression material, comprising:

a curable silicone polymer containing at least two functional groups capable of reacting with a SiH group in the presence of a hydrosilation catalyst;

a crosslinker compound containing at least two SiH groups;

a catalyst capable of catalyzing a hydrosilation reaction; and one or more cure-indicating dyes, wherein said dye exhibits a color change within about 10 minutes at 25° C. when 500 μg of said dye, 500 μl of dichloromethane, 100 μl of pentamethyldisiloxane and 10 μl of a hydrosilation catalyst solution having between about 2 and 3 weight percent platinum are mixed together, wherein said dye is represented by the formula

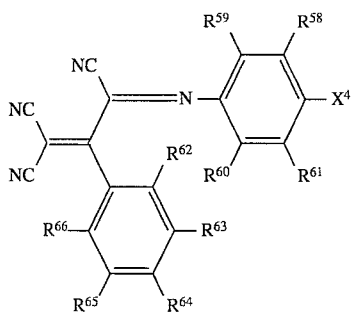

wherein $X^4$ is $N-R^{67}$ $R^{68}$, $O-R^{69}$, $S-R^{70}$ or $CR^{71}$ $R^{72}$ $R^{73}$ and wherein each of $R^{58}$, $R^{59}$, $R^{60}$, $R^{61}$, $R^{62}$, $R^{63}$, $R^{64}$, $R^{65}$, $R^{66}$, is independently selected from the group consisting of hydrogen, halogen, a hydrocarbyl group optionally interrupted with one or more heteroatoms and an acyclic, alicyclic or aromatic heterocyclic group, and each of $R^{67}$, $R^{68}$, $R^{69}$, $R^{70}$, $R^{71}$, $R^{72}$, and $R^{73}$ is independently selected from the group consisting of hydrogen, a hydrocarbyl group optionally interrupted with one or more heteroatoms and an acyclic, alicyclic or aromatic heterocyclic group.

5. The composition of claim 4, wherein each of $R^{67}$, $R^{68}$, $R^{69}$, $R^{70}$, $R^{71}$, $R^{72}$, and $R^{73}$ is independently selected from the group consisting of hydrogen and alkyl that is optionally substituted by one or more cyano, alkoxy, hydroxy, alkylsiloxy, alkylsilyl, acyl, aryl, halo, arylsiloxy, arylsilyl, amino, and mono or dialkyl amino groups.

6. The composition of claim 4, wherein at least one of $R^{67}$, $R^{68}$, $R^{69}$, $R^{70}$, $R^{71}$, $R^{72}$, and $R^{73}$ is selected from the group consisting of —CH$_2$CH$_2$OSi(CH$_3$)$_2$C(CH$_3$)$_3$

—CH$_2$CH$_2$OC(O)CH$_2$CH(CH$_3$)CH$_2$C(CH$_3$)$_3$

—CH$_2$CH$_2$OC(O)C(CH$_3$)$_3$

—CH$_2$CH$_2$OCH$_2$OCH$_2$CH$_2$Si(CH$_3$)$_3$

—CH$_2$CH$_2$Cl

—CH$_2$CH$_2$OC(O)NHCH$_2$CH$_2$CH$_2$CH$_3$, and

—CH$_2$CH$_2$OC(O)NHCH$_2$CH$_2$CH$_2$Si(OCH$_2$CH$_3$)$_3$.

7. A dental impression material, comprising:

a curable silicone polymer containing at least two functional groups capable of reacting with a SiH group in the presence of a hydrosilation catalyst;

a crosslinker compound containing at least two SiH groups;

a catalyst capable of catalyzing a hydrosilation reaction; and one or more cure-indicating dyes, wherein said dye exhibits a color change within about 10 minutes at 25° C. when 500 µg of said dye, 500 µl of dichloromethane, 100 µl of pentamethyldisiloxane and 10 µl of a hydrosilation catalyst solution having between about 2 and 3 weight percent platinum are mixed together, wherein said dye is selected from compounds of the formula

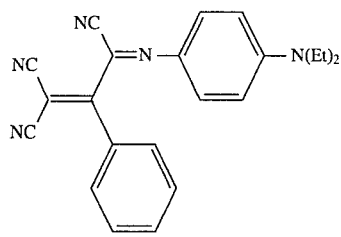

and

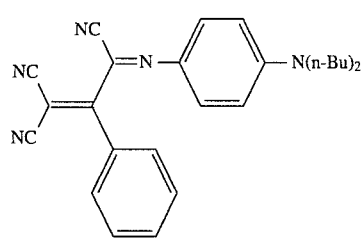

8. A dental impression material of claim 1, wherein said catalyst is a hydrosilation catalyst comprising a complex of platinum and an unsaturated organosilicon material.

9. A dental impression material of claim 7, wherein said catalyst is a hydrosilation catalyst comprising a complex of platinum and an unsaturated organosilicon material.

10. A dental impression material of claim 4, wherein said catalyst is a hydrosilation catalyst comprising a complex of platinum and an unsaturated organosilicon material.

11. A dental impression material, comprising:

a curable silicone polymer containing at least two functional groups capable of reacting with a SiH group in the presence of a hydrosilation catalyst;

a crosslinker compound containing at least two SiH groups;

a hydrosilation catalyst comprising a complex of platinum and an unsaturated organosilicon material; and one or more cure-indicating dyes, wherein, in a dye evaluation test, said dye exhibits a color change within about 10 minutes at 25° C. when 500 µg of said dye, 500 µl of dichloromethane, 100 µl of pentamethyldisiloxane and 10 µl of a hydrosilation catalyst solution having between about 2 and 3 weight percent platinum are mixed together and wherein said impression material exhibits a color change upon curing.

12. A dental impression material according to claim 11, wherein said impression material is provided to the user as two separate mixtures, wherein a first mixture comprises said catalyst and a second mixture comprises said crosslinker compound.

13. A dental impression material according to claim 11, wherein said hydrosilation catalyst comprises a complex of platinum, and a complexing material in the form of an unsaturated organosilicon material selected from the group consisting of:

unsaturated silanes having the empirical formula, $$R_a R'_b Si_c X_z$$

where R is free of aliphatic unsaturation and selected from monovalent hydrocarbon radicals, R' is selected from monovalent aliphatically unsaturated hydrocarbon radicals, X is a hydrolyzable radical, c is an integer having a value of at least 1, b is an integer having a value greater than or equal to 2 and the sum of a, b and z equals the sum of 2 and two times c for a linear or branched silane and wherein c is an integer having a value from 4 to 18 and the sum of a, b and z equals two times c for a cyclic silane;

unsaturated linear or branched siloxanes of the empirical formula, $R_d R'_e Si_f O_{(f-1)}$ where R and R' are as defined above, f is an integer having a value of between 2 and 10,000, e is an integer having a value greater than or equal to 2 and the sum of d and e equals the sum of 2 and two times f; and unsaturated cyclic siloxanes of the empirical formula, $R_d R'_e Si_f O_f$ where R and R' are as defined above, e is an integer having a value greater than or equal to 2, f is an integer having a value from 3 to 18, and the sum of d and e equals two times f.

14. A dental impression material according to claim 13, wherein said catalyst complex is formed using a platinum halide selected from the group consisting of $H_2PtCl_6.nH_2O$, $NaHPtCl_6.nH_2O$, $KHPtCl_6.nH_2O$, $Na_2PtCl_6.nH_2O$, $K_2PtCl_6.nH_2O$, $PtCl_4.nH_2O$, $PtCl_2$, $Na_2PtCl_4.nH_2O$, $H_2PtCl_4.nH_2O$, $NaHPtCl_4.nH_2O$, $KHPtCl_4.nH_2O$, $K_2PtBr_4$, $((CH_2=CH_2).PtCl_2)_2$, $(PtCl_2.C_3H_6)_2$, and the reaction product of chloroplatinic acid hexahydrate and octyl alcohol.

15. A dental impression material according to claim 12, wherein said catalyst is a Karstedt catalyst and has available inorganic halogen of less than 0.1 gram atoms of halogen per gram atom of platinum.

16. A dental impression material according to claim 13, wherein R' is selected from the group consisting of ethynyl, 1-propynyl, vinyl, allyl, cyclopentenyl, cyclohexenyl, cycloheptenyl, and cyclooctenyl.

17. A dental impression material according to claim 16, wherein R is selected from the group consisting of methyl, ethyl, propyl, butyl, hexyl, heptyl, octyl, cyclohexyl, cycloheptyl, phenyl, naphthyl, tolyl, xylyl, benzyl, phenylethyl, and phenylpropyl.

18. A dental impression material according to claim 13, wherein said unsaturated organosilicon material is an unsaturated silane selected from the group consisting of tetravinylsilane, triallylmethylsilane, divinyldimethylsilane, trivinylphenylsilane, divinylmethylphenylsilane, divinylmethylethoxysilane, divinylmethylacetoxysilane.

19. A dental impression material according to claim 17, wherein said unsaturated organosilicon material is an unsaturated linear or branched siloxane selected from the group consisting of disiloxanes of the formula, $R_g R'_h SiOSiR'_{h'} R_{g'}$ where h and h' are integers with a value of at least one, the sum of g and h is equal to 3, and the sum of g' and h' is equal to 3.

20. A dental impression material according to claim 17, wherein said unsaturated organosilicon material is selected from the group consisting of 1,1-divinyltetramethyldisiloxane, 1,3-divinyltetramethyldisiloxane, hexavinyldisiloxane, 1,1,3-trivinyltriethyldisiloxane, 1,1,3,3-tetravinyldimethyldisiloxane, 1,3,5-trivinyl-1,1,3,5,5-pentamethyltrisiloxane, and 1,3-divinyl,-1,3-dimethyl,-1,3-diphenyldisiloxane.

21. A dental impression material according to claim 12, wherein said unsaturated organosilicon material is an unsaturated siloxane selected from the group consisting of 1,3,5-trivinyl-1,3,5-trimethylcyclotrisiloxane, 1,3,5,7-tetraallyl, 1,3,5,7-tetraphenylcyclotetrasiloxane, 1,3-divinyloctamethylcyclopentasiloxane, and 1,3,5,7-tetravinyl-1,3,5,7-tetramethylcyclotetrasiloxane.

22. A dental impression material according to claim 12, wherein said cure-indicating dye changes color to indicate the gel point of said impression material.

23. A curable composition according to claim 12, wherein said cure-indicating dye changes color to indicate the set time of said impression material.

24. A dental impression material according to claim 11, wherein said cure-indicating dye is present in an amount between 0.0003 and 0.03 weight percent.

25. A dental impression material according to claim 11, wherein said cure-indicating dye has a molar extinction coefficient of at least 10,000 $M^{-1}cm^{-1}$.

26. A dental impression material according to claim 13, wherein said cure-indicating dye exhibits a loss of 90% in absorbance within about 10 minutes at 25° C. when 500 µg of said dye, 500 µl of dichloromethane, 100 µl of pentamethyldisiloxane and 10 µl of a hydrosilation catalyst solution having between about 2 and 3 weight percent platinum are mixed together, as compared to an identical solution that does not contain a hydrosilation catalyst.

27. A dental impression material according to claim 11, wherein said cure-indicating dye exhibits a loss of 99% in absorbance within about 10 minutes at 25° C. when 500 µg of said dye, 500 µl of dichloromethane, 100 µl of pentamethyldisiloxane and 10 µl of a hydrosilation catalyst solution having between about 2 and 3 weight percent platinum are mixed together, as compared to an identical solution that does not contain a hydrosilation catalyst.

28. A dental impression material according to claim 11, wherein said impression material exhibits a transition time between the onset of color change and the effective completion of the color change of less than three minutes at 32° C.

29. A dental impression material according to claim 11, wherein said cure-indicating dye is selected from the group consisting of indoaniline dyes, indophenol dyes, quinone monoimine dyes, quinone diimine dyes, cyanine dyes, merocyanine dyes, cyclohexadienone dyes, iminocyclohexadienone dyes, imidazolylidinecyclohexadienone dyes, dihydronaphthalenone dyes, iminodihydronaphthalenone dyes, imidazolylidinedihydronaphthalenone dyes, cyclohexadienimine dyes, aryl substituted bis (trifluoromethylsulfonyl)hexatrienyl dyes, aryl substituted bis (trifluoromethylsulfonyl)butadienyl dyes, aryl substituted bis (fluorosulfonyl)hexatrienyl dyes, aryl substituted bis (fluorosulfonyl)butadienyl dyes, oxazolone dyes, cationic dyes, anionic dyes and amphoteric dyes.

30. A dental impression material according to claim 11, wherein said cure-indicating dye is selected from the group consisting of neutral dyes represented by the following general formula:

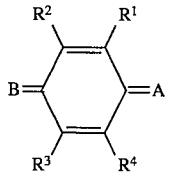

wherein:
each $R^1$, $R^2$, $R^3$, and $R^4$ group is independently hydrogen, halogen, a hydrocarbyl-containing group, or a heterocyclic group, and wherein $R^1$ and $R^2$ or $R^3$ and $R^4$ may be connected to form a saturated or unsaturated ring;

A is O, S, or $NR^{22}$, wherein $R^{22}$ is hydrogen, halogen, a hydrocarbyl-containing group, or a heterocyclic group; and B is any group capable of providing extended conjugation thereby rendering the dye capable of absorbing visible, near-UV, or near-infrared radiation including groups of formula D, E, F, H, or J, wherein D is represented by formula:

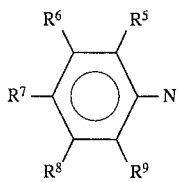

wherein:
each $R^5$, $R^6$, $R^7$, $R^8$, and $R^9$ group is independently hydrogen, halogen, a hydrocarbyl-containing group, or a heterocyclic group and wherein any two adjacent $R^5$, $R^6$, $R^7$, $R^8$, and $R^9$ groups may be connected to form a ring;

E is represented by formula:

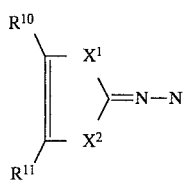

wherein:
$X^1$ is $C(R^{12})_2$, S, $NR^{12}$, or O;
$X^2$ is $C(R^{12})_2$, S, $NR^{12}$, or O; and
each $R^{10}$, $R^{11}$ and $R^{12}$ group is independently hydrogen, a hydrocarbyl-containing group, or a heterocyclic group and wherein $R^{10}$ and $R^{11}$ may be connected to form a ring;

F is represented by formula:

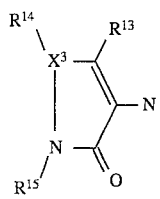

wherein:
$X^3$ is N or $CR^{16}$; and
each $R^{13}$, $R^{14}$, $R^{15}$, and $R^{16}$ group is independently hydrogen, halogen, a hydrocarbyl-containing group, or a heterocyclic group and wherein any two adjacent $R^{13}$, $R^{14}$, $R^{15}$, and $R^{16}$ groups may be connected to form a ring;

H is represented by formula:

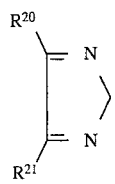

wherein:
each $R^{20}$ and $R^{21}$ group is independently hydrogen, halogen, a hydrocarbyl-containing group, or a hetero-cyclic group and wherein $R^{20}$ and $R^{21}$ may be connected to form a ring; and J is represented by formula:

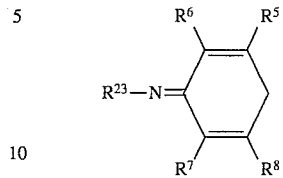

wherein:
each $R^5$, $R^6$, $R^7$ and $R^8$ group is independently hydrogen, halogen, a hydrocarbyl-containing group, or a heterocyclic group and wherein any two $R^5$, $R^6$, $R^7$ and $R^8$ groups may be connected to form a ring; and
$R^{23}$ is hydrogen, halogen, a hydrocarbyl-containing group, or a heterocyclic group;

sulfonyl dyes represented by the following general formula:

wherein:
each $R^{24}$ and $R^{25}$ group is independently hydrogen, a hydrocarbyl-containing group, or a heterocyclic group with the proviso that at least one of $R^{24}$ and $R^{25}$ is or contains a substituted aryl, aminoaryl or heterocyclic group;
each $R^{26}$ and $R^{27}$ group is independently a —$(CF_2)_mF$ group wherein m is a number between 0 and 20; and
n is an integer less than 5;

neutral dyes represented by the following general formula:

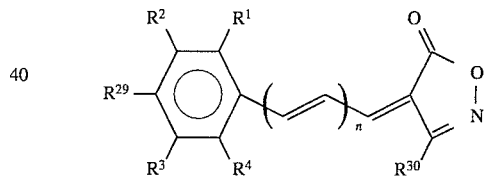

wherein:
each $R^1$, $R^2$, $R^3$, $R^4$, and $R^{29}$ group is independently hydrogen, halogen, a hydrocarbyl-containing group, or a heterocyclic group, and wherein any two adjacent $R^1$, $R^2$, $R^3$, $R^4$, or $R^{29}$ groups may be connected to form a ring; and
$R^{30}$ is hydrogen, halogen, a hydrocarbyl-containing group, or a heterocyclic group and n is an integer less than 5;

anionic dyes having the following general formula:

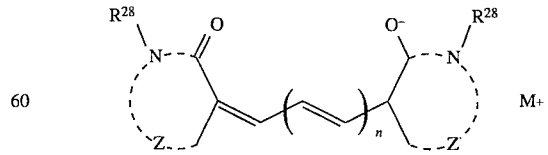

wherein:
Z represents the non-metallic atoms necessary to complete a substituted or unsubstituted nitrogen-containing heterocyclic ring;

each $R^{28}$ is independently hydrogen, a hydrocarbyl-containing group, or a heterocyclic group;

n is an integer less than 5; and wherein

M+ is selected from any suitable cation;

cationic dyes having the following general formula:

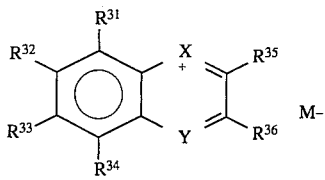

wherein:

each $R^{31}$, $R^{32}$, $R^{33}$, and $R^{34}$ group is independently hydrogen, halogen, a hydrocarbyl-containing group, or a heterocyclic group, and wherein any two adjacent $R^{31}$, $R^{32}$, $R^{33}$, or $R^{34}$ groups may be connected to form a ring;

$R^{35}$ and $R^{36}$ are as defined above for $R^{33}$ and $R^{34}$;

X is O, S, or $NR^{37}$;

Y is N or $CR^{38}$;

$R^{37}$ and $R^{38}$ are as defined above for $R^{33}$; and wherein

M− is any suitable anion;

cationic dyes having the following general formula:

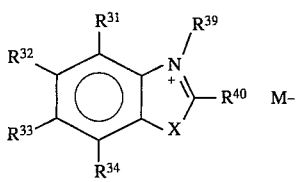

wherein:

each $R^{31}$, $R^{32}$, $R^{33}$, $R^{34}$ and $R^{40}$ group is independently hydrogen, halogen, a hydrocarbyl-containing group, or a heterocyclic group, and wherein any two adjacent $R^{31}$, $R^{32}$, $R^{33}$, or $R^{34}$ groups may be connected to form a ring;

$R^{39}$ is independently hydrogen, a hydrocarbyl-containing group, or a heterocyclic group;

X is $C=R^{48}$, $C(R^{38})_2$, O, S, or $NR^{37}$, wherein $R^{37}$ is as defined above for $R^{39}$, $R^{38}$ is as defined above for $R^{40}$, $R^{48}$ is an oxo group, a divalent hydrocarbyl-containing group or a divalent heterocyclic group, and wherein $R^{48}$ and $R^{34}$ may be connected to form an unsaturated ring, and $R^{37}$ and $R^{34}$ may be connected to form a ring; and wherein M− is any suitable anion; and cationic dyes having the following general formula:

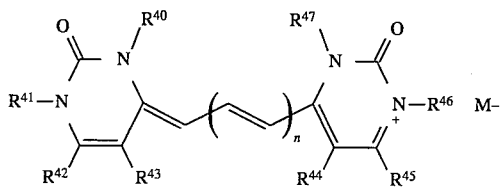

wherein:

each $R^{42}$ to $R^{47}$ group is independently hydrogen, halogen, a hydrocarbyl-containing group, or a heterocyclic group;

each $R^{40}$, $R^{41}$, $R^{46}$, and $R^{47}$ group is indepedently hydrogen, a hydrocarbyl-containing group, or a heterocyclic group and wherein any two adjacent $R^{41}$ to $R^{43}$ groups may be connected to form a ring and wherein $R^{44}$ and $R^{45}$ may be connected to form a ring;

n is an integer less than 5; and wherein

M− is any suitable anion.

31. A dental impression material according to claim 12, wherein said cure-indicating dye is a neutral dye.

32. A dental impression material according to claim 11, wherein said cure-indicating dye is selected from the group consisting of 4-[[4-(Dimethylamino)phenyl]imino]-2,5-cyclohexadien-1-one;

2-Chloro-4-[[2-methyl-4-(diethylamino)phenyl]imino]-2,5-cyclohexadien-1-one;

4-[[4-(Diethylamino)phenyl]imino]-1,4-dihydronaphthalen-1-one;

4-[[4-(Dimethylamino)phenyl]imino]-1,4-dihydronaphthalen-1-one;

4-[[2-methyl-4-(diethylamino)phenyl]imino]-1,4-dihydronaphthalen-1-one;

3-Methoxy-4-[[2-methyl-4-(diethylamino)phenyl]imino]-2,5-cyclohexadien-1-one;

3-Chloro-4-[[2-methyl-4-(diethylamino)phenyl]imino]-2,5-cyclohexadien-1-one;

2-Methyl-4-[[4-(4-morpholinyl)phenyl]-imino]-2,5-cyclohexadien-1-one;

2,6-Dichloro-4-[[4-(4-morpholinyl)-phenyl]imino]-2,5-cyclohexadien-1-one;

2,6-Dimethyl-4-[[4-(4-morpholinyl)-phenyl]imino]-2,5-cyclohexadien-1-one;

2,5-Dichloro-4-[[4-(diethylamino)-phenyl]imino]-2,5-cyclohexadien-1-one;

3-Methoxy-4-[[3-methoxy-4-(diethyl-amino)phenyl]imino]-2,5-cyclohexadien-1-one;

2,6-Dichloro-4-[[2-methyl-4-(diethylamino)phenyl]imino]-2,5-cyclohexadien-1-one;

3-[[4-(Diethylamino)-2-methylphenyl]imino]-6-oxo-N-phenyl-1,4-cyclohexadiene-1-carboxamide;

5-[[4-(Diethylamino)-2-methylphenyl]imino]-8-(5H)-quinolinone;

2,5-Dichloro-4-[[2-methyl-4-(diethylamino)-phenyl]imino]-2,5-cyclohexadien-1-one; 2,6-Dichloro-4-[[4-(acetamido)phenyl]imino]-2,5-cyclohexadien-1-one; 2,6-Dichloro-4-[4-ethoxy phenyl)imino]-2,5-cyclohexadien-1-one;

2,6-Dichloro-4-[(2-methyl-4-ethoxy phenyl)imino]-2,5-cyclohexadien-1-one;

2,6-Dimethyl-4-[4-hydroxy phenyl)imino]-2,5-cyclohexadien-1-one;

2,6-Dichloro-4-[(4-methoxy-1-naphthyl)imino]-2,5-cyclohexadien-1-one;

2,6-Dichloro-4-[[4-(benzyloxy)phenyl]imino]-2,5-cyclohexadien-1-one;

2,6-Dichloro-4-[(2,4-dimethoxyphenyl)imino]-2,5-cyclohexadien-1-one;

2,6-Dichloro-4-[(4-methoxyphenyl)imino]-2,5-cyclohexadien-1-one;

4-(phenylimino)-2,5-cyclohexadien-1-one; 4-(1-naphthylimino)-2,5-cyclohexadien-1-one; 4-(2-naphthylimino)-2,5-cyclohexadien-1-one;

2,5-Bis(phenylamino)-4(phenylimino)-2,5-cyclohexadien-1-one;

2,5-Dibromo-4-[(2,4-dibromophenyl)imino]-2,5-cyclohexadien-1-one;

2,3,5-Trichloro-4-[(2,4,6-trichlorophenyl)imino]-2,5-cyclohexadien-1-one;

2,6-Dichloro-4-[4-[4-(dimethylamino)phenyl]-5-phenyl-(2H)-imidazol-2-ylidine]-2,5-cyclohexadien-1-one; 2,6-Dichloro-4-[4,5-bis(4-hydroxyphenyl)-(2H)-imidazol-2-ylidine]-2,5-cyclohexadien-1-one; 2,6-Dimethoxy-4-[4,5-bis(2-furyl)-(2H)-imidazol-2-ylidine]-2,5-cyclohexadien-1-one;

2,6-Bis[1,1-(dimethyl)ethyl]-4-[4,5-bis(2-furyl)-(2H)-imidazol-2-ylidene]-2,5-cyclohexadien-1-one; 4-(phenylimino)-2,5-cyclohexadien-1-imine;

Mono[(3-methyl-2-(3H)-benzothiazolylidene)hydrazono] 2,5-cyclohexadiene-1,4-dione; 4-[(3-Chloro-4-oxo-2,5-cyclohexadien-1-ylidine)amino]-1,2-dihydro-1,5-dimethyl-2-phenyl-(3H)-pyrazol-3-one;

4-[(3,5-Dichloro-4-oxo-2,5-cyclohexadien-1-ylidine)amino]-1,2-dihydro-1,5-dimethyl-2-phenyl-(3H)-pyrazol-3-one;

3-[(3,5-Dichloro-4-oxo-2,5-cyclohexadien-1-ylidine)amino]-2,5-dihydro-4,5-dimethyl-1-phenylpyrrol-2-one; 4-(Phenylsulfonyl)imino-1-[4-[(phenylsulfonyl)imino]-2,5-cyclohexadien-1-ylidenyl]-2,5-cyclohexadiene;

4-[6,6-Bis[(trifluoromethyl)sulfonyl]-1,3,5-hexatrienyl]-N,N-dimethylbenzenamine;

4-[4,4-Bis[(trifluoromethyl)sulfonyl]-1,3-butadienyl]-2-ethoxy-N,N-dimethylbenzenamine; 4-[4,4-Bis[(trifluoromethyl)sulfonyl]-1,3-butadienyl]-2,5-dimethoxy-N,N-dimethyl benzenamine;

9-[4,4-Bis[(trifluoromethyl)sulfonyl]-1,3-butadienyl]-2,3,6,7-tetrahydro-(1H,5H)-benzo[ij]quinolizine; 4-[4,4-Bis[(trifluoromethyl)sulfonyl]-1,3-butadienyl]-2,6-N,N-tetramethyl-benzenamine; 4-[5,5-Bis[(trifluoromethyl)sulfonyl]-2,4-pentadienylidene]-1,4-dihydro-1-methylquinoline; 6,6-Bis[4-(dimethylamino)phenyl]1,3,5-hexatriene-1,1-bis(sulfonylfluoride); 4-[4,4-Bis[(trifluoromethyl)sulfonyl]-1,3-butadienyl]-N,N-dimethylbenzenamine; and 4-[3-[4-(Dimethylamino)phenyl]-2-propenylidene]-2-phenyl-5(4H)-oxazolone; anionic dyes having the following anions: 5-[5-(1,3-Diethylhexahydro-2,4,6-trioxo-5-pyrimidinyl)-2,4-pentadienylidene]-1,3-diethyl-2,4,6(1H,3H,5H)-pyrimidenetrione; and cationic dyes having the following cations or having the cations of the following cationic dyes: 3H-Indolium, 3-[3-[4-(dimethylamino)phenyl]-2-propenylidene]-1-methyl-2-phenyl; Benzothiazolium, 3-(3-amino-3-oxopropyl)-2-[[4-[bis(2-chloroethyl)amino]phenyl]azo]-6-methoxy-; Benzothiazolium, 3-(3-amino-3-oxopropyl)-2-[[4-(diethylamino)phenyl]azo]-6-ethoxy-; Benzothiazolium, 3-(3-amino-3-oxopropyl)-2-[[4-(diethylamino)-2-methylphenyl]azo]-6-ethoxy-; C. I. Basic Blue 68; C. I. Basic Blue 76; C. I. Basic Blue 57; C. I. Basic Blue 60; Benzo[a]phenoxazin-7-ium, 9-(dimethylamino)-; 2-[4,4,-bis[4-dimethylamino)phenyl]-1,3-butadienyl]-1-ethyl quinolinium; 4-[4,4,-bis[4-(dimethylamino)phenyl]-1,3-butadienyl]1-ethyl quinolinium; Naphtho[2,1-d]thiazolium, 2-[4,4-bis[4-(dimethylamino)phenyl]-1,3-butadienyl]-3-ethyl-; 2-[2-[4-(dimethylamino)phenyl]ethenyl]-1-phenyl-3-methyl quinoxalinium; Quinolinium, 2-[3-(5-chloro-1,3-dihydro-1,3,3-trimethyl-(2H)-indol-2-ylidene)-1-propenyl]-1-methyl-; Benzothiazolium, 2-[[4-(dimethylamino)phenyl]azo]-6-methoxy-3-methyl-; Benz[cd]indolium, 2-[4-(diethylamino)-2-ethoxyphenyl]-1-ethyl-; 2-[p-(Dimethylamino)styryl]-1,3-dimethylquinoxalinium; 2-[3-(5-chloro-1,3-dihydro-1,3,3-trimethyl-(2H)-indol-2-ylidene)-1-propenyl]-1-methylquinoxalinium; C. I. Basic Blue 40; Benzothiazolium, 2-[[4-[ethyl(2-hydroxyethyl)amino]phenyl]azo]-6-methoxy-3-methyl-; Benzothiazolium, 2-[[4-[ethyl(2-hydroxyethyl)amino]phenyl]azo]-6-methoxy-3-methyl-; C. I. Basic Blue 42; C. I. Basic Blue 53; 3H-Indolium, 5-chloro-2-[5-(5-chloro-1,3-dihydro-1,3,3-trimethyl-2H-indol-2-ylidene)-1,3-pentadienyl]-1,3,3-trimethyl-; C. I. Basic Blue 142; Benz[cd]indolium, 2-[2-(9-ethyl-(9H)-carbazol-3-yl)ethenyl]-1-methyl-; Benz[cd]indolium, 2-[2-[4-(dimethylamino)phenyl]-2-phenylethenyl]-1-methyl-; Benz[cd]indolium, 2-[2,2-bis[4-(dimethylamino)phenyl]ethenyl]-1-methyl-; Benz[cd]indolium, 2-[2-(2,3-dihydro-1-methyl-2-phenyl-1H-indol-3-yl)-2-(2-methylphenyl)ethenyl]-1-methyl-; Pyrimidinium, 4-[5-(2,3-dihydro-1,3-dimethyl-2-oxo-; 4(1H)-pyrimidinylidene)-1,3-pentadienyl]-2,3-dihydro-1,3-dimethyl-2-oxo-; 3H-Indolium, 2-[[3-[(1,3-dihydro-1,3,3-trimethyl-2H-indol-2-ylidene)methyl]-5,5-dimethyl-2-cyclohexen-1-ylidene]methyl]-1,3,3-trimethyl-; Benz[cd]indolium, 2-[2-[4-(diethylamino)-2-methylphenyl]ethenyl]-1-methyl-; 3H-Indolium, 3-[3-[4-[(dimethylamino)phenyl]-2-propenylidene]-1-methyl-2-(4-methoxyphenyl)-; 3H-Indolium, 3-[(2,5-dimethyl-1-phenyl-(1H)-pyrrol-3-yl)methylene]-1,2-dimethyl-; 3H-Indolium, 3-[2,5-dimethyl-1-phenyl-(1H)-pyrrol-3-yl)methylene]-1-methyl-2-phenyl-; 2-[2-[2-chloro-4-(dimethylamino)phenyl]ethenyl]-1-methylbenz[cd]indolium; C. I. Basic Violet 22; C. I. Basic Red 15; Benz[cd]indolium, 2-[2-[4-(dimethylamino)phenyl]ethenyl]-1-methyl-; Benz[cd]indolium, 2-[2-[4-(dimethylamino)-2-ethoxyphenyl]ethenyl]-1-methyl-; and 3H-Indolium, 2-[1-cyano-4,4-bis[4-(dimethylamino)phenyl]-1,3-butadienyl]-1,3,3-trimethyl-.

33. A dental impression material according to claim 11, wherein said cure-indicating dye is selected from the group consisting of 4-[[4-(Dimethylamino)phenyl]imino]-2,5-cyclohexadien-1-one; 2-Chloro-4-[[2-methyl-4-(diethylamino)phenyl]imino]-2,5-cyclohexadien-1-one; 4-[[4-(Diethylamino)phenyl]imino]-1,4-dihydronaphthalen-1-one; 4-[[4-(Dimethylamino)phenyl]imino]-1,4-dihydronaphthalen-1-one; 4-[[2-methyl-4-(diethylamino)phenyl]imino]-1,4-dihydronaphthalen-1-one; 3-Methoxy-4-[[2-methyl-4-(diethylamino)phenyl]imino]-2,5-cyclohexadien-1-one; 2-Methyl-4-[[4-(4-morpholinyl)phenyl]imino]-2,5-cyclohexadien-1-one; 2,5-Dichloro-4-[[4-(diethylamino)phenyl]imino]-2,5-cyclohexadien-1-one; 3-[[4-(Diethylamino)-2-methylphenyl]imino]-6-oxo-N-phenyl-1,4-cyclohexadiene-1-carboxamide; 5-[[4-(Diethylamino)-2-methylphenyl]imino]-8-(5H)-quinolinone; 2,6-Dichloro-4-[[4-(acetamido)phenyl]imino]-2,5-cyclohexadien-1-one; 4-(1-naphthylimino)-2,5-cyclohexadien-1-one; 4-(2-naphthylimino)-2,5-cyclohexadien-1-one; 2,5-Bis(phenylamino)-4(phenylimino)-2,5-cyclohexadien-1-one; 4-[5,5-Bis[(trifluoromethyl)sulfonyl]-2,4-pentadienylidene]-1,4-dihydro-1-methylquinoline; 6,6-Bis[4-(dimethylamino)phenyl]1,3,5-hexatriene-1,1-bis(sulfonylfluoride); 4-[4,4-Bis[(trifluoromethyl)sulfonyl]-

1,3-butadienyl]-N,N-dimethylbenzenamine; and 4-[3-[4-(Dimethylamino)phenyl]-2-propenylidene]-2-phenyl-5(4H)-oxazolone.

34. A dental impression material according to claim 12, wherein said impression material comprises between 20 and 90 weight percent filler.

35. A dental impression material according to claim 29, wherein said impression material further comprises an indicator adjuvent comprising an active proton.

36. A dental impression material according to claim 15, further comprising a non-cure-indicating dye or pigment.

37. A dental impression material, comprising:
  a curable silicone polymer containing at least two functional groups capable of reacting with a SiH group in the presence of a hydrosilation catalyst;
  a crosslinker compound containing at least two SiH groups;
  a hydrosilation catalyst comprising a complex of platinum and a complexing material in the form of an unsaturated organosilicon material selected from the group consisting of:
    unsaturated silanes having the empirical formula,

where R is free of aliphatic unsaturation and selected from monovalent hydrocarbon radicals, R' is selected from monovalent aliphatically unsaturated hydrocarbon radicals, X is a hydrolyzable radical, c is an integer having a value of at least 1, b is an integer having a value greater than or equal to 2 and the sum of a, b and z equals the sum of 2 and two times c for a linear or branched silane and wherein c is an integer having a value from 4 to 18 and the sum of a, b and z equals two times c for a cyclic silane;
    unsaturated linear or branched siloxanes of the empirical formula,

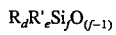

where R and R' are as defined above, f is an integer having a value of between 2 and 10,000, e is an integer having a value greater than or equal to 2 and the sum of d and e equals the sum of 2 and two times f; and
    unsaturated cyclic siloxanes of the empirical formula,

where R and R' are as defined above, e is an integer having a value greater than or equal to 2, f is an integer having a value from 3 to 18, and the sum of d and e equals two times f, and wherein said catalyst complex is formed using a platinum halide selected from the group consisting of $H_2PtCl_6 \cdot nH_2O$, $NaHPtCl_6 \cdot nH_2O$, $KHPtCl_6 \cdot nH_2O$, $Na_2PtCl_6 \cdot nH_2O$, $K_2PtCl_6 \cdot nH_2O$, $PtCl_4 \cdot nH_2O$, $PtCl_2$, $Na_2PtCl_4 \cdot nH_2O$, $H_2PtCl_4 \cdot nH_2O$, $NaHPtCl_4 \cdot nH_2O$, $KHPtCl_4 \cdot nH_2O$, $K_2PtBr_4$, $((CH_2=CH_2) \cdot PtCl_2)_2$, $(PtCl_2 \cdot C_3H_6)_2$, and the reaction product of chloroplatinic acid hexahydrate and octyl alcohol; and
  one or more cure-indicating dyes, wherein said impression material exhibits a color change upon curing, wherein said dye exhibits a color change within about 10 minutes at 25° C. when 500 μg of said dye, 500 μl of dichloromethane, 100 μl of pentamethyldisiloxane and 10 μl of a hydrosilation catalyst solution having between about 2 and 3 weight percent platinum are mixed together, and wherein said cure-indicating dye is present in an amount between 0.0003 and 0.03 weight percent.

38. A dental impression material, comprising:
  a curable silicone polymer containing at least two functional groups capable of reacting with a SiH group in the presence of a hydrosilation catalyst;
  a crosslinker compound containing at least two SiH groups;
  a hydrosilation catalyst comprising a complex of platinum and a complexing material in the form of an unsaturated organosilicon material selected from the group consisting of:
    unsaturated silanes having the empirical formula,

where R is free of aliphatic unsaturation and selected from monovalent hydrocarbon radicals, R' is selected from monovalent aliphatically unsaturated hydrocarbon radicals, X is a hydrolyzable radical, c is an integer having a value of at least 1, b is an integer having a value greater than or equal to 2 and the sum of a, b and z equals the sum of 2 and two times c for a linear or branched silane and wherein c is an integer having a value from 4 to 18 and the sum of a, b and z equals two times c for a cyclic silane;
    unsaturated linear or branched siloxanes of the empirical formula,

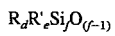

where R and R' are as defined above, f is an integer having a value of between 2 and 10,000, e is an integer having a value greater than or equal to 2 and the sum of d and e equals the sum of 2 and two times f; and
    unsaturated cyclic siloxanes of the empirical formula,

where R and R' are as defined above, e is an integer having a value greater than or equal to 2, f is an integer having a value from 3 to 18, and the sum of d and e equals two times f, and wherein said catalyst complex is formed using a platinum halide selected from the group consisting of $H_2PtCl_6 \cdot nH_2O$, $NaHPtCl_6 \cdot nH_2O$, $KHPtCl_6 \cdot nH_2O$, $Na_2PtCl_6 \cdot nH_2O$, $K_2PtCl_6 \cdot nH_2O$, $PtCl_4 \cdot nH_2O$, $PtCl_2$, $Na_2PtCl_4 \cdot nH_2O$, $H_2PtCl_4 \cdot nH_2O$, $NaHPtCl_4 \cdot nH_2O$, $KHPtCl_4 \cdot nH_2O$, $K_2PtBr_4$, $((CH_2=CH_2) \cdot PtCl_2)_2$, $(PtCl_2 \cdot C_3H_6)_2$, and the reaction product of chloroplatinic acid hexahydrate and octyl alcohol, and wherein said catalyst is a Karstedt catalyst and has available inorganic halogen of less than about 0.1 gram atoms of halogen per gram atom of platinum; and
  one or more cure-indicating dyes having a molar extinction coefficient of at least 10,000 $M^{-1}cm^{-1}$, wherein said impression material exhibits a color change upon curing of at least 10 $\Delta E^*$ units.

39. A dental impression material comprising:
  a curable silicone polymer containing at least two functional groups capable of reacting with a SiH group in the presence of a catalyst;
  a crosslinker compound containing at least two SiH groups;
  a hydrosilation catalyst; and
  one or more cure-indicating dyes selected from the group consisting of neutral dyes represented by the following general formula:

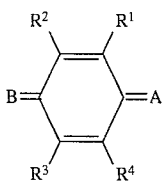

wherein:
  each $R^1$, $R^2$, $R^3$, and $R^4$ group is independently hydrogen, halogen, a hydrocarbyl-containing group, or a heterocyclic group, and wherein $R^1$ and $R^2$ or $R^3$ and $R^4$ may be connected to form a saturated or unsaturated ring;
  A is O, S, or $NR^{22}$, wherein
  $R^{22}$ is hydrogen, halogen, a hydrocarbyl-containing group, or a heterocyclic group; and
  B is any group capable of providing extended conjugation thereby rendering the dye capable of absorbing visible, near-UV, or near-infrared radiation including groups of formula D, E, F, H, or J, wherein
  D is represented by formula:

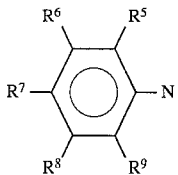

each $R^5$, $R^6$, $R^7$, $R^8$, and $R^9$ group is independently hydrogen, halogen, a hydrocarbyl-containing group, or a heterocyclic group and wherein any two adjacent $R^5$, $R^6$, $R^7$, $R^8$, and $R^9$ groups may be connected to form a ring;
E is represented by formula:

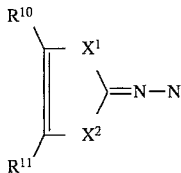

wherein:
  $X^1$ is $C(R^{12})_2$, S, $NR^{12}$, or O;
  $X^2$ is $C(R^{12})_2$, S, $NR^{12}$, or O; and
  each $R^{10}$, $R^{11}$ and $R^{12}$ group is independently hydrogen, a hydrocarbyl-containing group, or a heterocyclic group and wherein $R^{10}$ and $R^{11}$ may be connected to form a ring;
F is represented by the formula:

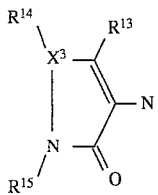

wherein:
  $X^3$ is N or $CR^{16}$; and
  each $R^{13}$, $R^{14}$, $R^{15}$, and $R^{16}$ group is independently hydrogen, halogen, a hydrocarbyl-containing group, or a heterocyclic group and wherein any two adjacent $R^{13}$, $R^{14}$, $R^{15}$, and $R^{16}$ groups may be connected to form a ring;
H is represented by formula:

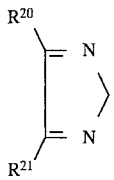

wherein:
  each $R^{20}$ and $R^{21}$ group is independently hydrogen, halogen, a hydrocarbyl-containing group, or a heterocyclic group and wherein $R^{15}$, and $R^{16}$ may be connected to form a ring; and
J is represented by formula:

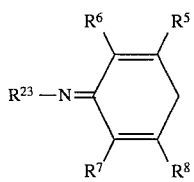

wherein:
  each $R^5$, $R^6$, $R^7$ and $R^8$ group is independently hydrogen, halogen, a hydrocarbyl-containing group, or a heterocyclic group and wherein any two $R^5$, $R^6$, $R^7$ and $R^8$ groups may be connected to form a ring; and
  $R^{23}$ is hydrogen, halogen, a hydrocarbyl-containing group, or a heterocyclic group;
sulfonyl dyes represented by the following general formula:

wherein:
  each $R^{24}$ and $R^{25}$ group is independently hydrogen, a hydrocarbyl-containing group, or a heterocyclic group with the proviso that at least one of $R^{24}$ and $R^{25}$ is or contains a substituted aryl, aminoaryl or heterocyclic group;
  each $R^{26}$ and $R^{27}$ group is independently a $-(CF_2)_mF$ group wherein m is a number between 0 and 20; and
  n is an integer less than 5;
neutral dyes represented by the following general formula:

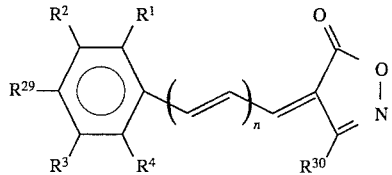

wherein:
  each $R^1$, $R^2$, $R^3$, $R^4$, and $R^{29}$ group is independently hydrogen, halogen, a hydrocarbyl-containing group, or a heterocyclic group, and wherein any two adjacent $R^1$, $R^2$, $R^3$, $R^4$, or $R^{29}$ groups may be connected to form a ring; and $R^{30}$ is hydrogen, halogen, a hydrocarbyl-containing group, or a heterocyclic group and n is an integer less than 5;

anionic dyes having the following general formula:

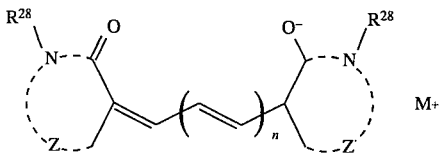

wherein:

Z represents the non-metallic atoms necessary to complete a substituted or unsubstituted nitrogen-containing heterocyclic ring;

each $R^{28}$ is independently hydrogen, a hydrocarbyl-containing group, or a heterocyclic group;

n is an integer less than 5; and wherein

M+ is selected from any suitable cation;

cationic dyes having the following general formula:

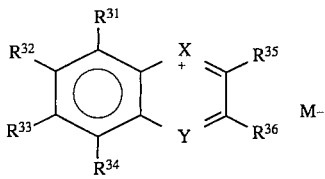

wherein:

each $R^{31}$, $R^{32}$, $R^{33}$, and $R^{34}$ group is independently hydrogen, halogen, a hydrocarbyl-containing group, or a heterocyclic group, and wherein any two adjacent $R^{31}$, $R^{32}$, $R^{33}$, or $R^{34}$ groups may be connected to form a ring;

$R^{35}$ and $R^{36}$ are as defined above for $R^{33}$ and $R^{34}$;

X is O, S, or $NR^{37}$;

Y is N or $CR^{38}$;

$R^{37}$ and $R^{38}$ are as defined above for $R^{33}$; and wherein

M– is any suitable anion;

cationic dyes having the following general formula:

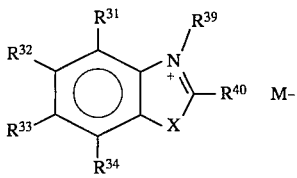

wherein:

each $R^{31}$, $R^{32}$, $R^{33}$, $R^{34}$ and $R^{40}$ group is independently hydrogen, halogen, a hydrocarbyl-containing group, or a heterocyclic group, and wherein any two adjacent $R^{31}$, $R^{32}$, $R^{33}$, or $R^{34}$ groups may be connected to form a ring;

$R^{39}$ is independently hydrogen, a hydrocarbyl-containing group, or a heterocyclic group;

X is C=$R^{48}$, C($R^{38}$)$_2$, O, S, or $NR^{37}$, wherein $R^{37}$ is as defined above for $R^{39}$, $R^{38}$ is as defined above for $R^{40}$, $R^{48}$ is an oxo group, a divalent hydrocarbyl-containing group or a divalent heterocyclic group, and wherein $R^{48}$ and $R^{34}$ may be connected to form an unsaturated ring, and $R^{37}$ and $R^{34}$ may be connected to form a ring; and wherein M– is any suitable anion; and cationic dyes having the following general formula:
cationic dyes having the following general formula:

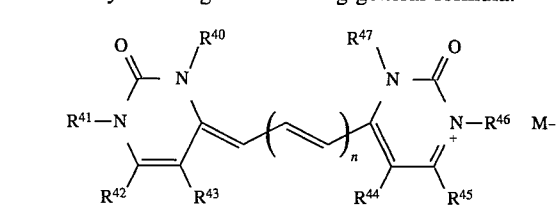

wherein:

each $R^{42}$ to $R^{47}$ group is independently hydrogen, halogen, a hydrocarbyl-containing group, or a heterocyclic group;

each $R^{40}$, $R^{41}$, $R^{46}$, and $R^{47}$ group is indepedently hydrogen, a hydrocarbyl-containing group, or a heterocyclic group and wherein any two adjacent $R^{41}$ to $R^{43}$ groups may be connected to form a ring and wherein $R^{44}$ and $R^{45}$ may be connected to form a ring;

n is an integer less than 5; and wherein

M– is any suitable anion, and wherein said dental impression material exhibits a color change upon curing of at least 10 ΔE* units.

40. A method of monitoring the curing of a dental impression material, comprising the steps of:

placing against the teeth of a patient an impression material comprising a curable silicone polymer containing at least two functional groups capable of reacting with a SiH group in the presence of a hydrosilation catalyst, a crosslinker compound containing at least two SiH groups, a hydrosilation catalyst comprising a complex of platinum and an unsaturated organosilicon material, and one or more cure-indicating dyes; and visually observing said impression material, wherein said impression material has a first color before the cure reaction is effected and a second color after the cure reaction has been effected to an indication point, and wherein said first and second colors differ by at least 5 ΔE* units.

41. A method of monitoring the curing of a dental impression material according to claim 40, wherein the second color of said dental impression material is compared to a reference color standard and wherein the color difference between the reference color standard and the second color of said dental impression material is less than 3 ΔE* units.

42. A method of monitoring the curing of a curable composition according to claim 40, wherein the first color of said dental impression material is compared to a reference color standard and wherein the color difference between the reference color standard and the first color of said dental impression material is less than 3 ΔE* units.

43. A method of monitoring the curing of a dental impression material according to claim 41, wherein said reference color standard is selected from the group consisting of printed cards, printed labels, colored plastic parts, painted parts, colored ceramic parts, and colored dental impression materials.

44. A method of monitoring the curing of a dental impression material according to claim 40, wherein said first and second colors differ by at least 10 ΔE* units.

45. A method of monitoring the curing of a dental impression material according to claim 40, wherein said first and second colors differ by at least 15 ΔE* units.

46. A method of monitoring the curing of a dental impression material according to claim 40, wherein said dye exhibits a color change within about 10 minutes at 25° C. when 500 µg of said dye, 500 µl of dichloromethane, 100 µl of pentamethyldisiloxane and 10 µl of a hydrosilation catalyst solution having between about 2 and 3 weight percent platinum are mixed together.

47. A method of monitoring the curing of a dental impression material according to claim 46, wherein said cure indicating dye provides an indication of the set time of said impression material, and wherein the color of said impression material is compared to a reference color standard selected from the group consisting of printed cards, printed labels, colored plastic parts, painted parts, colored ceramic parts, and colored curable compositions and wherein the color difference between the reference color standard and the second color of said impression material is less than 3 ΔE* units.

48. A method of monitoring the curing of a curable composition according to claim 46, further comprising the step of:

placing said dental impression material against the teeth of a patient and allowing said impression material to cure.

49. A method of monitoring the curing of a curable composition according to claim 48, further comprising the step of:

removing said impression material from the mouth of said patient, and then visually observing the surface of said impression material for the presence of any regions which exhibit less color change than the bulk of the impression.

50. A method of monitoring the curing of a curable composition according to claim 48, further comprising the step of:

removing said impression material from the mouth of said patient, and then visually observing the surface of said impression material for the presence of any regions which after 30 seconds exhibit less color change than the bulk of the impression.

51. A method of monitoring the curing of a curable composition according to claim 42, wherein the time at which the color difference between said impression material and said reference color standard is greater than 3 ΔE* units corresponds to just before the gel point of the impression material.

52. A method of monitoring the curing of a curable composition according to claim 42, wherein the time at which the color difference between said impression material and said reference color standard is greater than 3 ΔE* units corresponds to just after the gel point of the impression material.

53. A dental impression material comprising:

a curable silicone polymer containing at least two functional groups capable of reacting with a SiH group in the presence of a catalyst;

a crosslinker compound containing at least two SiH groups;

a hydrosilation catalyst;

between 20 and 90 weight percent filler;

a surfactant; and one or more cure-indicating dyes selected from the group consisting of indoaniline dyes, indophenol dyes, quinone monoimine dyes, quinone diimine dyes, cyanine dyes, merocyanine dyes, cyclohexadienone dyes, iminocyclohexadienone dyes, imidazolylidinecyclohexadienone dyes, dihydronaphthalenone dyes, iminodihydronaphthalenone dyes, imidazolylidinedihydronaphthalenone dyes, cyclohexadienimine dyes, aryl substituted bis (trifluoromethylsulfonyl)hexatrienyl dyes, aryl substituted bis (trifluoromethylsulfonyl)butadienyl dyes, aryl substituted bis (fluorosulfonyl)hexatrienyl dyes, aryl substituted bis (fluorosulfonyl)butadienyl dyes, oxazolone dyes, cationic dyes, anionic dyes and amphoteric dyes, wherein said impression material exhibits a color change upon curing of at least 10 ΔE* units.

\* \* \* \* \*